US 8,153,737 B2

(12) United States Patent
Yiannikouris et al.

(10) Patent No.: US 8,153,737 B2
(45) Date of Patent: Apr. 10, 2012

(54) SYNTHETIC MYCOTOXIN ADSORBENTS AND METHODS OF MAKING AND UTILIZING THE SAME

(75) Inventors: Alexandros Yiannikouris, Lexington, KY (US); Stefan Kwiatkowski, Lexington, KY (US); Manoj Bojappa Kudupoje, Lexington, KY (US); Clayton Matney, Greensburg, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

(21) Appl. No.: 12/870,664

(22) Filed: Aug. 27, 2010

(65) Prior Publication Data
US 2011/0054132 A1    Mar. 3, 2011

Related U.S. Application Data

(60) Provisional application No. 61/237,549, filed on Aug. 27, 2009.

(51) Int. Cl.
*C08F 20/18* (2006.01)
*C07D 209/38* (2006.01)

(52) U.S. Cl. ......... 526/215; 548/485; 562/445; 436/178
(58) Field of Classification Search .................. 526/215; 548/485; 562/445; 436/178
See application file for complete search history.

(56) References Cited

FOREIGN PATENT DOCUMENTS
WO    WO 03/101580 A1  *  12/2003
* cited by examiner

*Primary Examiner* — Robert D. Harlan
(74) *Attorney, Agent, or Firm* — Casimir Jones S.C.

(57) ABSTRACT

The present invention relates generally to molecularly imprinted polymers (MIPs). In particular, the present invention relates to reusable, ecologically friendly MIPs that can be produced in relatively large quantities, methods of producing the same, and methods of utilizing the same (e.g., to sequester and/or adsorb target compounds (e.g., mycotoxins)). Compositions and methods of the invention find use in a variety of applications including dietary therapeutic, prophylactic, food and beverage processing and manufacture, as well as research, quality control and traceability applications.

9 Claims, 16 Drawing Sheets

Template

Ochratoxin A

Mycotoxin - Spirodesmin A

5-Chloro-6,7-dimethoxy-1-methylisatine
Spirodesmin A template under the form of
metabolites of the parent toxin ingested. Temperature treatments such as cooking and freezing are not adequate methods of decreasing the prevalence of mycotoxins. Thus, there exists a need for compositions and/or methods for reducing the detrimental effects and/or eliminating mycotoxin occurrence in feed and/or food chains.

SYNTHETIC MYCOTOXIN ADSORBENTS AND METHODS OF MAKING AND UTILIZING THE SAME

CROSS-REFERENCE TO RELATED APPLICATION

The present Application claims priority to U.S. Provisional Application Ser. No. 61/237,549 filed Aug. 27, 2009, the entirety of which is herein incorporated by reference.

FIELD OF THE INVENTION

The present invention relates generally to molecularly imprinted polymers (MIPs). In particular, the present invention relates to reusable, ecologically friendly MIPs, methods of producing the same, and methods of utilizing the same (e.g., to sequester and/or adsorb targets (e.g., mycotoxins)). Compositions and methods of the invention find use in a variety of applications including dietary, therapeutic, prophylactic, food and beverage processing and manufacture, as well as research and quality control applications.

BACKGROUND OF THE INVENTION

Mycotoxins are secondary metabolites secreted by a variety of fungi, often produced in cereal grains as well as forages before, during and after harvest. Forages and cereals naturally come into contact with fungal spores. The fungal contamination of plants and the bio-synthesis of toxins depend on the state of health of the plant before harvest, meteorological conditions, harvesting techniques, delays and hydrothermal conditions before stabilization for conservation and feed processing. Depending on the fungus, fungal growth is controlled by a number of physico-chemical parameters including the amount of free water ($a_w$), temperature, presence of oxygen, nature of the substrate, and pH conditions. Mycotoxins proliferate pre-harvest as well as post-harvest in storage.

Some fungi produce toxins only at specific levels of moisture, temperature or oxygen. The effects of mycotoxins vary greatly in their severity. Some mycotoxins are lethal, some cause identifiable diseases or health problems, some weaken the immune system without producing symptoms specific to that mycotoxin, some act as allergens or irritants, and some have no known effect on animals or humans. During World War II Russian soldiers suffered severe dermal necrosis, hemorrhage and destruction of bone marrow after eating moldy grains that were contaminated with *Fusarium*. However, it was not until the 1960's, when more than 100,000 turkeys of Britain were decimated by a fatal liver disease (Turkey X Disease) that the scientific community recognized the negative effects associated with mycotoxins (See, e.g., Trenholm H. L., Charmley L. L., and Prelusky D. B., 1996. *Mycotoxin binding agents: An update on what we know*. In: Biotechnology in the Feed Industry (Lyons T. P and Jacques K. A eds.) Nottingham University Press, Loughborough, Leics, UK, pp. 327-349.). According to recent United Nation's Food and Agriculture Organization (FAO) reports, approximately 25% of the world's grain supply is contaminated with mycotoxins. Mycotoxin contamination has a negative economic impact on food and feed producers, particularly grain and poultry producers.

Mycotoxins can appear in the food chain as a result of fungal infection of plant products (e.g., forage, grain, plant protein, processed grain by-products, roughage and molasses products), and can either be eaten directly by humans, or introduced by contaminated grains, livestock or other animal feedstuff(s). Mycotoxins greatly resist decomposition during digestion so they remain in the food chain in edible products (e.g., meat, fish, eggs and dairy products) or under the form of metabolites of the parent toxin ingested. Temperature treatments such as cooking and freezing are not adequate methods of decreasing the prevalence of mycotoxins. Thus, there exists a need for compositions and/or methods for reducing the detrimental effects and/or eliminating mycotoxin occurrence in feed and/or food chains.

SUMMARY OF THE INVENTION

The present invention relates to molecularly imprinted polymers (MIPs). In particular, the present invention relates to reusable, ecologically friendly MIPs, methods of producing the same, and methods of utilizing the same (e.g., to sequester and/or adsorb targets (e.g., mycotoxins)). Compositions and methods of the invention find use in a variety of applications including dietary, therapeutic, prophylactic, food and beverage processing and manufacture, as well as research and quality control applications.

Accordingly, in some embodiments, the invention provides a composition comprising a molecularly imprinted polymer synthesized using a mycotoxin template. The present invention is not limited to the mycoxin template utilized to generate a molecularly imprinted polymer. Indeed, a variety of mycotoxin templates may be utilized including, but not limited to, acetoxyscirpenediol, acetyldeoxynivalenol, acetylnivalenol, acetylneosolaniol, acetyl T-2 toxin, aflatoxin, aflatoxin B1, B2, G1 and G2, aflatrem, altenuic acid, alternariol, austdiol, austamide, austocystin, avenacein +1, beauvericin +2, bentenolide, brevianamide, butenolide, calonectrin, chaetoglobosin, chaetocin, chaetomin, citrinin, citreoviridin, cochliodinol, cytochalasins, cyclopiazonic acid, deacetylcalonectrin, deactylneosolaniol, deoxynivalenol diacetate, deoxynivalenol monoacetate, diacetoxyscirpenol, destruxin B, emestrin, enniatins, ergot alkaloids toxins and endophytes such as ergine, ergocornine, ergocristine, ergocryptine, ergometrine, ergonine, ergosine, ergotamine, ergovaline, lysergol, lysergic acid, and related epimers, fructigenin +1, fumagilin, fumonisins, fumonisins A1, A2, B1 and B2 and B3, fusarenon-X, fusarochromanone, fusaric acid, fusarin, gliotoxin, HT-2 toxin, hyalodendrin, ipomeanine, islanditoxin, isofumigaclavines A and B, lateritin +1, leptosin, lycomarasmin+1, malformin, maltoryzine, moniliformin, monoacetoxyscirpenol, mycophenolic acid, neosolaniol, nivalenol, NT-1 toxin, NT-2 toxin, ochratoxin, oosporein, oxalic acid, paspalitrem A and B, patulin, penicillic acid, penitrem, phomopsins, PR-toxin, roridin E, roquefortine A and B, rubratoxin, rubroskyrin, rubrosulphin, rugulosin, sambucynin +1, satratoxins, F,G,H, scirpentriol, sirodesmin, slaframine, sporidesmin, sterigmatocystin, swainsonine, T-1 toxin, T-2 toxin, tenuazoic acid, triacetoxyscirpendiol, trichothecenes, trichodermin, trichothecin, trichoverrins, trichoverrols, tryptoquivalene, verrucarin, verruculogen, verticillins, viopurpurin, viomellein, viriditoxin, wortmannin, xanthocillin, yavanicin+1, zearalenols, zearalanones, zearalenone, α, β, zearalanone, α, β, zeranol and subfamilies and/or derivatives of the same, and/or conjugates. In some preferred embodiments, the mycotoxin template is OTA. In other preferred embodiments, the mycotoxin template is sporidesmin or an ergot alkaloid. In some embodiments, the ochratoxin template is N-(2-hydroxy-3,5-dichlorobenzoyl)-L-phenylalanine. In some embodiments, the sporidesmin template is 5-chloro-6,7-dimethoxy-1-methylisatine. However, the present invention is not limited to these ochratoxin or sporidesmin templates. Indeed, a variety of different templates may be utilized including N-tert-butoxycarbonyl-2,3-dimethoxyaniline, 2,3-dimethoxyaniline, ethyl 3-hydroxy-6,7-dimethoxy-2-indolone-3-carboxylate, 6,7-dimethoxyisatine, or 6,7-dimethoxy-1-methylisatine.

In some embodiments, the invention provides a method of making a molecularly imprinted polymer comprising: providing: a mycotoxin template; and one or more monomers and one or more crosslinkers; and contacting the mycotoxin template with the one or more monomers and the one or more crosslinkers under conditions that permit polymerization of the one or more monomers and the one or more crosslinkers in the presence of the mycotoxin template. In some embodiments, the mycotoxin template is N-(2-hydroxy-3,5-dichlorobenzoyl)-L-phenylalanine. In some embodiments, the mycotoxin template is 5-chloro-6,7-dimethoxy-1-methylisatine. The present invention is not limited to the mycotoxin template utilized. Indeed, a variety of synthetic molecules can be utilized as mycotoxin templates wherein the synthetic molecules mimic one or more of the structures, shapes and/or other chemical characteristics of natural mycotoxins. The present invention is likewise not limited to the types of monomers utilized. For example, a variety of monomers are known to those of ordinary skill in the art and include, but are not limited to, 2-vinylpyridine, 2-hydroxyethylmethacrylate and methacrylic acid. The present invention is likewise not limited to the type of crosslinker utilized. For example, a variety of crosslinkers are known to those of ordinary skill in the art and include, but are not limited to, ethylene glycol dimethacrylate. In some embodiments, the polymerization is initiated by forming free radicals in an organic solvent at a temperature between 55 and 110 degrees Celsius, although lower (e.g., 50, 45, 40, 35, 30 degrees Celsius or lower) and higher (e.g., 115, 120, 125, 130 degrees Celsius or higher) may be utilized. In some embodiments, the free radicals are formed by thermally initiated decomposition of azoisobutyronitrile (AIBN). The present invention is not limited by the type of organic solvent utilized. In some embodiments, the organic solvent is toluene, cyclohexane, acetonitrile, a polyvinyl alcohol (PVA)/water solution, and a mixture of two or more of toluene, cyclohexane, acetonitrile, and a PVA/water solution. In some embodiments, the temperature is between 55 and 75 degrees Celsius. In some embodiments, the mycotoxin template is removed from the molecularly imprinted polymer after polymerization of the one or more monomers and the one or more crosslinkers. In some embodiments, one or more washes with a solution is utilized to remove the mycotoxin template from the molecularly imprinted polymer. The present invention is not limited by the type of solution utilized for washing. In some embodiments, the solution is an organic solvent, a buffer, water or a combination thereof. The present invention is not limited by the type of organic solvent utilized. In some embodiments, the organic solvent is ethyl alcohol, methyl alcohol, acetonitrile, toluene, and/or a mixture thereof. In some embodiments, the buffer is a buffer prepared by reacting sodium hydroxide, citric acid, succinic acid and acetic acid. In some embodiments, the water is deionized water. In some embodiments, the molecularly imprinted polymer is dried after the one or more washes. In some embodiments, exposure of the molecularly imprinted polymer to a temperature between 20 and 90 degrees Celsius (e.g., between 60 and 80 degrees Celsius; between 75 and 80 degrees Celsius) is utilized to dry the molecularly imprinted polymer, although lower or higher temperatures may be utilized.

In some embodiments, the invention provides a method of sequestering a mycotoxin from a material, comprising: providing a material comprising mycotoxins; and a molecularly imprinted polymer generated via polymerization of one or more monomers and one or more crosslinkers in the presence of a mycotoxin template; and contacting the molecularly imprinted polymer with the material comprising mycotoxins under conditions that permit the molecularly imprinted polymer to bind the myotoxin. The present invention is not limited by the type of mycotoxins sequestered (e.g., targeted for sequestration) from the material. Indeed, a variety of mycotoxins may be sequestered including, but not limited to, acetoxyscirpenediol, acetyldeoxynivalenol, acetylnivalenol, acetylneosolaniol, acetyl T-2 toxin, aflatoxin, aflatoxin B1, B2, G1 and G2, aflatrem, altenuic acid, alternariol, austdiol, austamide, austocystin, avenacein +1, beauvericin +2, bentenolide, brevianamide, butenolide, calonectrin, chaetoglobosin, chaetocin, chaetomin, citrinin, citreoviridin, cochliodinol, cytochalasins, cyclopiazonic acid, deacetylcalonectrin, deactylneosolaniol, deoxynivalenol diacetate, deoxynivalenol monoacetate, diacetoxyscirpenol, destruxin B, emestrin, enniatins, ergot alkaloids toxins and endophytes such as ergine, ergocornine, ergocristine, ergocryptine, ergometrine, ergonine, ergosine, ergotamine, ergovaline, lysergol, lysergic acid, and related epimers, fructigenin +1, fumagilin, fumonisins, fumonisins A1, A2, B1 and B2 and B3, fusarenon-X, fusarochromanone, fusaric acid, fusarin, gliotoxin, HT-2 toxin, hyalodendrin, ipomeanine, islanditoxin, isofumigaclavines A and B, lateritin +1, leptosin, lycomarasmin +1, malformin, maltoryzine, moniliformin, monoacetoxyscirpenol, mycophenolic acid, neosolaniol, nivalenol, NT-1 toxin, NT-2 toxin, ochratoxin, oosporein, oxalic acid, paspalitrem A and B, patulin, penicillic acid, penitrem, phomopsins, PR-toxin, roridin E, roquefortine A and B, rubratoxin, rubroskyrin, rubrosulphin, rugulosin, sambucynin +1, satratoxins, F,G,H, scirpentriol, sirodesmin, slaframine, sporidesmin, sterigmatocystin, swainsonine, T-1 toxin, T-2 toxin, tenuazoic acid, triacetoxyscirpendiol, trichothecenes, trichodermin, trichothecin, trichoverrins, trichoverrols, tryptoquivalene, verrucarin, verruculogen, verticillins, viopurpurin, viomellein, viriditoxin, wortmannin, xanthocillin, yavanicin+1, zearalenols, zearalanones, zearalenone, α, β, zearalanone, α, β, zeranol and subfamilies and/or derivatives of the same. In some preferred embodiments, the mycotoxin sequestered form the material is ochratoxin A. In some preferred embodiments, the mycotoxin is sporidesmin. In some embodiments, the material comprising mycotoxins is a beverage, a foodstuff, an animal feed, a pharmaceutical composition, a nutraceutical composition, a cosmetic composition, a substance necessary to sustain life, or other material. In some embodiments, the substance necessary to sustain life is a medium for use in aquaculture and a gaseous sample comprising oxygen. In some embodiments, a molecularly imprinted polymer bound to a mycotoxin is not separated from the material comprising mycotoxins. In some embodiments, the method of sequestering a mycotoxin from a material, further comprises separating molecularly imprinted polymers bound to mycotoxin from the material comprising mycotoxins. In some embodiments, separating comprises extracting, concentrating and isolating the molecularly imprinted polymers bound to mycotoxin from the material comprising mycotoxins. In some embodiments, the separating occurs in a chromatographic or separative column or cartridge. In some embodiments, after separating, mycotoxin bound to the molecularly imprinted polymers are removed from the molecularly imprinted polymers by washing. In some embodiments, the mycotoxins are qualitatively and quantitatively analyzed after removal from the molecularly imprinted polymers. In some embodiments, the quantitative and qualitative analysis is utilized for traceability (e.g., to identify and/or interrelate the chronology, location, and/or application of an item (e.g., the location, type and amount of mycotoxins found) by means of documented recorded identification). In some embodiments, the molecularly imprinted polymer from which mycotoxins has been removed is reused to sequester a mycotoxin from a material comprising mycotoxins. In some embodiments, the molecularly imprinted polymer adsorbs 1 to 10 times more (e.g., 1 to 5 times more, 1 to 2 times more) water than its weight. In some embodiments, two or more different molecularly imprinted polymers are contacted with the material comprising mycotoxins in order to sequester two or more specific mycotoxins from the material.

The invention also provides a method for synthesizing N-(2-hydroxy-3,5-dichlorobenzoyl)-L-phenylalanine, comprising: converting 3-5 dichlorosalicylic acid into 2-acetoxyacetoxy-3,5-dichlorobenzoic acid; converting 2-acetoxyacetoxy-3,5-dichlorobenzoic acid into 2-acetoxyacetoxy-3,5-dichlorobenzoic acid chloride; reacting 2-acetoxyacetoxy-3,5-dichlorobenzoic acid chloride with L-phenylalanine ethyl ester to form N-(2-acetoxy-3,5-dichlorobenzoyl)-L-phenylalanine; and converting N-(2-acetoxy-3,5-dichlorobenzoyl)-L-phenylalanine into N-(2-hydroxy-3,5-dichlorobenzoyl)-L-phenylalanine. In some embodiments, the converting comprises hydrolyzing of ester functions in N-(2-acetoxy-3, 5-dichlorobenzoyl)-L-phenylalanine.

The invention also provides a method for synthesizing 5-chloro-6,7-dimethoxy-1-methylisatine, comprising: converting 2,3-dimethoxybenzoic acid into 2,3-dimethoxy-N-tertbutoxycarbonylaniline; converting 2,3-dimethoxy-N-tertbutoxycarbonylaniline into 2,3-dimethoxyaniline; reacting 2,3-dimethoxyaniline with diethylketomalonate to form ethyl 6,7-dimethoxy-3-hydroxy-3-(2-indolone)-carboxylate; converting ethyl 6,7-dimethoxy-3-hydroxy-3-(2-indolone)-carboxylate into 6,7-dimethoxyisatine; converting 6,7-dimethoxyisatine into 6,7-dimethoxy-1-methylisatine; and converting 6,7-dimethoxy-1-methylisatine into 5-chloro-6,7-dimethoxy-1-methylisatine.

The invention also provides a method of synthesizing a molecularly imprinted polymer specific for a mycotoxin, comprising: generating a template compound capable of facilitating MIP binding to the mycotoxin; combining the template compound in a reaction comprising a MIP monomer and a cross-linking reagent in a solvent system comprising an apolar, non-protic solvent; and promoting polymerization by an action selected from the group consisting of exposing the reactant vessel to an elevated temperature or exposing the reactant vessel to UV irradiation. In some embodiments, the mycotoxin comprises ochratoxin A, however, the invention is not so limited. Indeed, a variety of molecularly imprinted polymers specific for a mycotoxin can be synthesized as described herein including, but not limited to, MIPs specific for acetoxyscirpenediol, acetyldeoxynivalenol, acetylnivalenol, acetylneosolaniol, acetyl T-2 toxin, aflatoxin, aflatoxin B1, B2, G1 and G2, aflatrem, altenuic acid, alternariol, austdiol, austamide, austocystin, avenacein +1, beauvericin +2, bentenolide, brevianamide, butenolide, calonectrin, chaetoglobosin, chaetocin, chaetomin, citrinin, citreoviridin, cochliodinol, cytochalasins, cyclopiazonic acid, deacetylcalonectrin, deactylneosolaniol, deoxynivalenol diacetate, deoxynivalenol monoacetate, diacetoxyscirpenol, destruxin B, emestrin, enniatins, ergot alkaloids toxins and endophytes such as ergine, ergocornine, ergocristine, ergocryptine, ergometrine, ergonine, ergosine, ergotamine, ergovaline, lysergol, lysergic acid, and related epimers, fructigenin +1, fumagilin, fumonisins, fumonisins A1, A2, B1 and B2 and B3, fusarenon-X, fusarochromanone, fusaric acid, fusarin, gliotoxin, HT-2 toxin, hyalodendrin, ipomeanine, islanditoxin, isofumigaclavines A and B, lateritin +1, leptosin, lycomarasmin +1, malformin, maltoryzine, moniliformin, monoacetoxyscirpenol, mycophenolic acid, neosolaniol, nivalenol, NT-1 toxin, NT-2 toxin, ochratoxin, oosporein, oxalic acid, paspalitrem A and B, patulin, penicillic acid, penitrem, phomopsins, PR-toxin, roridin E, roquefortine A and B, rubratoxin, rubroskyrin, rubrosulphin, rugulosin, sambucynin +1, satratoxins, F,G,H, scirpentriol, sirodesmin, slaframine, sporidesmin, sterigmatocystin, swainsonine, T-1 toxin, T-2 toxin, tenuazoic acid, triacetoxyscirpendiol, trichothecenes, trichodermin, trichothecin, trichoverrins, trichoverrols, tryptoquivalene, verrucarin, verruculogen, verticillins, viopurpurin, viomellein, viriditoxin, wortmannin, xanthocillin, yavanicin+1, zearalenols, zearalanones, zearalenone, α, β, zearalanone, α, β, zeranol and subfamilies and/or derivatives of the same. In some embodiments, the template comprises N-(2-hydroxy-3,5-dichlorobenzoyl)-L-phenylalanine. In some embodiments, the template comprises 5-chloro-6,7-dimethoxy-1-methylisatine. The present invention is not limited to any particular monomer or crosslinker. Indeed, a variety of monomers and crosslinkers may be utilized including those described herein. In some embodiments, the method further comprises washing the molecularly imprinted polymer to remove the template. In some embodiments, washing comprises 1, 2, 3, 4 or more washes with a solution (e.g., a dilute alkali solution, a dilute acid solution, or water) to remove the template.

DESCRIPTION OF THE DRAWINGS

FIG. 2 shows N-(3,5-dichloro-2-hydroxybenzoyl)-L-phenylalanine (OTA template) synthetic pathway.

FIG. 12 shows the sporidesmin and sporidesmin template (5-chloro-6,7-dimethoxy-1-methylisatine) molecular structure.

DEFINITIONS

Figure 1:
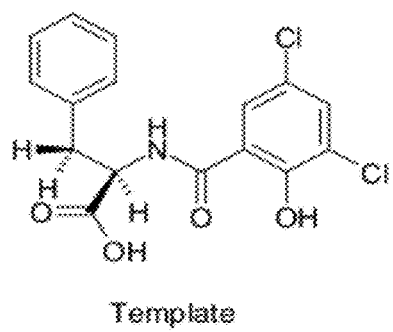
FIG. 1 shows ochratoxin A and N-(3,5-dichloro-2-hydroxybenzoyl)-L-phenylalanine (OTA template).
Figure 1:
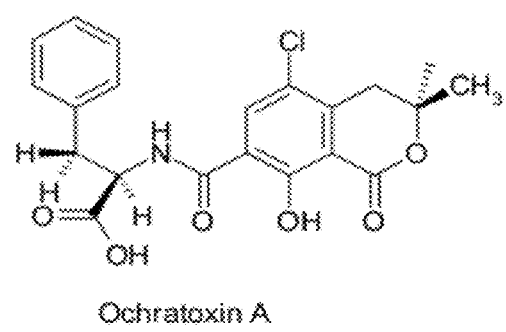

As used herein, the term "molecularly imprinted polymer" or "MIP" refers to synthetic polymers that selectively bind a particular compound. In a preferred embodiments, molecularly imprinted polymers are synthesized in the presence of target compounds, also referred to as template compounds, creating a MIP with a high degree of affinity for the specific target compound (e.g., mycotoxins). In general, the polymers are constructed with templates (e.g., synthetically constructed molecule/ligand/template (e.g., synthetic mycotoxins template)) that mimic the structure, shape and/or other chemical characteristics of a natural target (e.g., natural mycotoxins) and other components such as monomers and/or cross linking reagents. For example, the template compounds are incorporated into a pre-polymeric mixture and allowed to form associates with the monomers. The mixture is then polymerized with the template compounds in place. Once the polymer has formed, the template compounds are removed, leaving behind complementary cavities with affinity for the template (or other compositions resembling the template (e.g., natural occurring mycotoxins). Such regions (e.g., cavities or other regions) are tailored for binding future target compounds giving rise to a high affinity for such compounds.

It is worthy to note, that while specific target compounds are used to form molecularly imprinted polymers, the polymers may have a high affinity for a class of compounds that is distinct from but similar to the target compound. For example, a molecularly imprinted polymer may bind a number of compounds that are similar in shape, charge density, geometry or other physical or chemical properties to the template compound (e.g., synthetic mycotoxin template).

As used herein, the term "polymer", refers to a molecule (macromolecule) composed of repeating structural units typically connected by covalent chemical bonds forming a network.

As used herein, the term "template compound" or "target compound" refers to a compound that is complexed by ligands (e.g., monomers) that are subsequently polymerized, forming a molecularly imprinted polymer. Template compounds include organic compounds (e.g., mycotoxins, peptides, and proteins) as well as inorganic compounds (e.g., minerals, and heavy metals). As used herein, the term "mycotoxin template" refers to a synthetically constructed molecule that mimics the structure, shape and/or other chemical characteristic of a natural mycotoxin (e.g., ochrotoxin, sporidesmin, etc.). The present invention is not limited by the type of mycotoxin template utilized. Indeed a variety of mycotoxins may be utilized including, but not limited to, Aflatoxins: aflatoxin B1, B2, G1, G2, M1, P1, Q1, sterigmatocystin and subfamilies, aflatoxicol; Trichothecenes: deoxynivalenol, diacetoxyscirpenol, monoacetoxyscirpenol, scirpentriol, T-2 toxin, HT-2 toxins, T-2 tetraol, fusarenon X, fusarin C, fusaric acid, fusarochromanone, aurofusarin, fusaproliferin, neosolaniol, nivalenol along with metabolites and subfamilies; Fumonisins: fumonisin A1, A2, B1, B2, B3 and subfamilies; Ochratoxins: ochratoxin A, B, $\alpha$, $\beta$ and metabolites; Zearalenone, zearalenol $\alpha$, $\beta$, zearalanone, zearalanol $\alpha$, $\beta$, zeranol and metabolites; Patulin, gliotoxin, mycophenolic acid, moniliformin cyclopiazonic acid, citrinin, beauvericin, citreoviridin, citochalasin H; Penicillic acid, PR-toxin, roquefortine A, B, rubratoxin and subfamilies; Ergot alkaloids: ergotamine, clavine alkaloids; Isofumigaclavines A, B; paspalitrem A, B, aflatrem, penitrems and subfamilies; Phomopsins: Phomopsin A and subfamilies; Verrucarin A, verruculogen and subfamilies; Sporidesmin and subfamilies; slaframine, swainsonine, tenuazoic acid, alternariol, wortmannin, and other mycotoxins described herein.

As used herein, the term "monomer", refers to a molecule that may become chemically bonded to other monomers to form a polymer.

As used herein, the terms "crosslink" and "crosslinker", refer to molecules that contain two, three or four double-bonds that are capable of attaching to two or more monomers to form a polymer network.

As used herein, the term "structural unit", refers to a building block of a polymer chain, and related to the repeat unit.

As used herein, the term "anionic" or "anion" refers to an ion that has a negative charge.

As used herein, the term "cationic" or "cation" refers to an ion that has a positive charge.

This term can refer to polymeric compounds, such as molecularly imprinted polymers, that contain a positive charge.

As used herein, the term "acid" as used herein refers to any chemical compound that can donate proton(s) and/or accept electron(s). As used herein, the term "base" refers to any chemical compound that can accept proton(s) and/or donate electron(s) or hydroxide ions. As used herein, the term "salt" refers to compounds that may be derived from inorganic or organic acids and bases.

As used herein, the term "bleeding", refers to a remaining fraction of the template still in association with the MIP after several washing stages of the MIP, and that continues to dissociate from the MIP and interfere with its sorption activity.

As used herein, the term "porogenic/porogen", refers to a substance, molecule, buffer, solvent, (e.g., toluene, xylene, ethylbenzene) used to change the size of the cavities on a polymer (e.g., cavities of a MIP), while the polymer to porogen ratio is directly correlated to the amount of porosity of the final structure.

As used herein, the term "porosity", refers to a measure of the void spaces in a material (e.g., a MIP cavity) that can hold a gas or liquid or allow it to pass through.

As used herein, the term "polymerization", refers to a process of reacting monomer molecules together in a chemical reaction to form three-dimensional networks or polymer chains.

As used herein, the term "precipitation", refers to the formation of a solid in a solution during a chemical reaction. When the reaction occurs, the solid formed is called the precipitate, and the liquid remaining above the solid is called the supernatant.

As used herein, the term "centrifugation" refers to the process of separating molecules by size or density using centrifugal forces generated by a spinning rotor that puts an object in rotation around a fixed axis, applying a force perpendicular to the axis. The centrifuge works using the sedimentation principle, where the centripetal acceleration is used to evenly distribute substances of greater and lesser density into different layers of density.

As used herein, the term "concentration" refers to the amount of a substance per defined space. Concentration usually is expressed in terms of mass per unit of volume. To dilute a solution, one must add more solvent, or reduce the amount of solute (e.g., by selective separation, evaporation, spray drying, freeze drying). By contrast, to concentrate a solution, one must reduce the amount of solvent.

As used herein, the term "layer" refers to a usually horizontal deposit organized in stratum of a material forming an overlying part or segment obtained after separation by centrifugation or sedimentation in relation with the density properties of the material.

As used herein, the term "purified" or "to purify" refers to the removal of foreign components from a sample. When used in a chemical context "purified" or "to purify" refers to the physical separation of a chemical substance of interest from foreign, undesired or contaminating substances. Commonly used methods for purification of organic molecules, include, but are not limited to the following: affinity purification, mechanical filtration, centrifugation, evaporation, extraction of impurity, dissolving in a solvent in which other components are insoluble, crystallization, adsorption, distillation, fractionation, sublimation, smelting, refining, electrolysis and dialysis.

As used herein, the term "drying" refers to any kind of process that reduces or eliminates liquid in a substance.

As used herein, the term "spray drying" refers to a method of drying a substance containing liquid using hot gas to evaporate the liquid to reduce or eliminate liquid in the substance. In other words the material is dried byway of spraying or atomizing into a draft of heated dry air.

As used herein, the term "dry free flowing powder" refers to a free flowing dry powder.

As used herein, the term "grinding" refers to reducing particle size by impact, shearing, or attrition.

As used herein, the term "washing" refers to the removal or cleansing (e.g., using any type of solute (e.g., distilled water, buffer, or solvent, or mixture) of impurities or soluble unwanted component of a preparation (e.g., a MIP may be washed to remove the template components from the sample).

As used herein, the term "analyte" refers to an atom, a molecule, a substance, or a chemical constituent. In general, an analyte, in and of itself is not measured, rather, aspects or properties (physical, chemical, biological, etc.) of the analyte are determined using an analytical procedure, such as High Performance Liquid Chromatography (abbreviated as HPLC). For example, in general one does not measure a "chair" (analyte-component) in and of itself, but, the height, width, etc. of a chair are measured. Likewise, in general one does not measure a mycotoxin but rather measures one or more properties of the mycotoxin (e.g., mycotoxins fluorescence, related for example, to its stability, concentration, or biological activity).

As used herein, the term "sample" is used in a broad sense including a specimen from any source (e.g., synthetic, biological and environmental samples). Synthetic samples include any material that is artificially produced (e.g., MIP). Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples.

As used herein, the term "high-performance liquid chromatography" and the term "HPLC" refer to a form of liquid chromatography to separate compounds. The compounds are dissolved in a solution. Compounds are separated by injecting the sample mixture onto a column, through which a solvent or solvent mixture has been flowing, to elute components of the mixture, from the column. HPLC instruments comprise a reservoir of mobile phase, a pump, an injector, a separation column, and a detector. The presence of analytes in the column effluent is recorded by quantitatively detecting a change in refractive index, UV-VIS absorption at a set wavelength, fluorescence after excitation with a suitable wavelength, or electrochemical response.

As used herein, the term "signal" is used generally in reference to any detectable process that indicates that a reaction has occurred (for example, binding of antibody to antigen). Signals can be assessed qualitatively as well as quantitatively. Examples of types of "signals" include, but are not limited to, radioactive signals, fluorometric signals or colorimetric product/reagent signals.

As used herein, the term "scanning electron microscopy" and the term "SEM" refer to a type of electron microscope that images the sample surface by scanning it with a high-energy beam of electrons in a raster scan pattern. The electrons interact with the atoms that make up the sample, producing signals that contain information about the sample's surface topography, composition and other properties such as electrical conductivity.

As used herein, the term "fixation agent" refers to a chemical that is capable of fixing one substance to another in order to "fix", stabilize, or otherwise preserve the substance in its current form to prevent the substance from degrading or otherwise changing. Often, fixation agents are used in scanning electron microscopy (SEM) to prepare the sample.

As used herein, the term "in vivo" refers to studies and/or experiments conducted within a living organism, occurring within a biological organism.

As used herein, the term "in vitro" refers to an artificial environment outside the living organism and to biological processes or reactions that would normally occur within an organism but are made to occur in an artificial environment. Examples of in vitro environments include test tubes and cell culture.

As used herein, the term "in situ" means in the condition of the reaction mixture.

As used herein, the term "ex vivo" refers to studies and/or experiments and/or application done in or on living tissue in an artificial environment outside the organism with the minimum alteration of the natural conditions.

As used herein, the term "absorb" refers to the process by which a material "takes in" or "sucks up" another substance. For example, "absorption" may refer to the process of absorbing or assimilating substances into cells or across the tissues and organs through diffusion or osmosis (e.g., absorption of nutrients by the digestive system or absorption of drugs into the blood stream).

As used herein, the terms "adsorb" and "adsorption" refer to a process that occurs when a material is sequestered by, and/or accumulated by (e.g., on the surface of) a composition (sequestrant and/or adsorbent), or to a process in which a composition (e.g., MIP) binds to a target molecule (e.g., a mycotoxins) in a sample (e.g., for removing the target molecule from a sample).

As used herein, the term "sorption" refers to both adsorption and absorption.

As used herein, the term "sequester" and/or the term "sequestration" refers to physical association (e.g., via bonding (e.g., hydrogen boding, ionic bonding, covalent bonding or other type of bonding) of two or more entities that come into contact with one another (e.g., thereby forming a complex). Exemplary forms of associations include, but are not limited to, hydrogen bonding, coordination, and ion pair formation. Sequestration interactions may involve a variable number of chemical interactions (e.g., chemical bonds) depending on the stereochemistry and geometry of each entity (e.g., further defining the specificity of the sequestration). When two or more entities are sequestered they may be sequestered by way of chemical bonds, but may also be associated via charge, dipole-dipole or other type of interactions.

As used herein, the terms "sequestration agent" and/or "sequestering agent", refer to an entity that is capable of forming a complex with a second entity.

As used herein, the term "complex" refers to an entity formed by association between two or more separate entities (e.g., association between two or more entities wherein the entities are the same or different (e.g., same or different chemical species). The association may be via a covalent bond or a non-covalent bond (e.g., via van der Waals, electrostatic, charge interaction, hydrophobic interaction, dipole interaction, and/or hydrogen bonding forces (e.g., urethane linkages, amide linkages, ester linkages, and combination thereof)).

As used herein, the term "effective amount" refers to the amount of a composition (e.g., MIP) sufficient to accomplish beneficial or desired results. An effective amount can be administered and/or combined with another material in one or more administrations, applications or dosages and is not intended to be limited to a particular formulation or administration route.

As used herein, the term "animal" refers to those of animal kingdom. This includes, but is not limited to livestock, farm animals, domestic animals, pet animals, marine and freshwater animals, and wild animals.

As used herein, the term "feedstuffs" refers to material(s) that are consumed by a subject (e.g., a human and/or animal subject (e.g., that contribute energy and/or nutrients to the subject's diet)). Examples of feedstuffs include, but are not limited to, dairy, juice, grains, fruit, vegetables, meat, Total Mixed Ration (TMR), forage(s), pellet(s), concentrate(s), premix(es) coproduct(s), grain(s), distiller grain(s), molasses, fiber(s), fodder(s), grass(es), hay, kernel(s), leaves, meal, soluble(s), and supplement(s).

As used herein, "digestive system" refers to a system (including gastrointestinal system) in which digestion can or does occur.

As used herein, the term "digest" or "digestion" refers to the conversion of food, feedstuffs, or other organic compounds into absorbable form; to soften, decompose, or break down by heat and moisture or chemical action.

As used herein, the term "bioavailability" refers to the fraction of a molecule or component that is available to an organism or reaches the systemic circulation. When a molecule or component is administered intravenously, its bioavailability is 100%. However, when a molecule or component is administered via other routes (such as orally), its bioavailability decreases (due to incomplete absorption and first-pass metabolism).

As used herein, the terms "administration" and the term "administering" refer to the act of giving a substance, including a drug, prodrug, or other agent, or therapeutic treatment to a subject (e.g., a subject or in vivo, in vitro, or ex vivo cells, tissues, and organs). Exemplary routes of administration can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the term "co-administration" and the term "co-administering" refer to the administration of at least two agent(s) or therapies to a subject and/or material (e.g., feedstuff). Co-administration of two or more agents or therapies can be concurrent, or a first agent/therapy can be administered prior to a second agent/therapy.

As used herein, the term "treatment" refers to the improvement and/or reversal of a sign or symptom of disease (e.g., mycotoxicosis). The term "treatment" refers to both therapeutic treatment and prophylactic or preventative measures. For example, subjects that may benefit from treatment with compositions and methods of the invention include those already with a disease and/or disorder (e.g., mycotoxicosis) as well as those in which a disease and/or disorder is to be prevented (e.g., using a prophylactic treatment of the present invention).

As used herein, the term "mycotoxin" refers to toxic and/or carcinogenic compound(s) produced by various fungal species.

As used herein, the term "mycotoxicosis" refers to a condition in which mycotoxins pass the resistance barriers of a human or animal body. Mycotoxicosis can be considered either an infection or a disease and may have a deleterious effect on those afflicted.

As used herein, the terms "disease", "infection" and "pathological condition or response" refer to a state, signs, and/or symptoms that are associated with an impairment of the normal state of a living subject (e.g., human and/or animal) or of any of its organs or tissues that interrupts or modifies the performance of normal functions, and may be a response to environmental factors (such as malnutrition, industrial hazards, or climate, including mycotoxicosis), specific infective agents (such as worms, amoeba, bacteria, viruses, prions, etc.), to inherent defect of the organism (such as various genetic anomalies), or combinations of these and other factors.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds (e.g., present in the environment, etc.)).

As used herein, the term "suffering from disease" refers to a subject (e.g., an animal or human subject) that is experiencing a particular disease and is not limited to any particular signs or symptoms, or disease.

As used herein, the term "toxic" refers to any detrimental, deleterious, harmful, or otherwise negative effect(s) on a subject, a cell, or a tissue as compared to the same cell or tissue prior to the contact or administration of the toxin/toxicant.

As used herein, the term "pharmaceutical composition" refers to the combination of an active agent (e.g., a composition comprising a MIP) with a carrier, inert or active, making the composition especially suitable for diagnostic or therapeutic use in vitro, in vivo or ex vivo.

As used herein, the term "pharmaceutically acceptable" and the term "pharmacologically acceptable" refer to compositions that do not substantially produce more known adverse reactions than known beneficial reactions.

As used herein, the term "traceability" refers to the property of the result of a measurement or the value of a standard whereby it can be related to stated references, usually national or international standards, through an unbroken chain of comparisons, all having stated uncertainties. It is the practical application of general metrology concepts to chemical measurements and provides the terminology, concepts and strategy for ensuring also that analytical chemical measurements are comparable. It measures the uniquely identifiable entities in a way that is verifiable. Traceability measures are utilized, among other things, to interrelate the chronology, location, and/or application of an item by means of documented recorded identification.

DETAILED DESCRIPTION OF THE INVENTION

Various fungal groups produce mycotoxins that have deleterious effects on animal health. These toxins are mainly produced by the fungal genera of *Aspergillus, Fusarium* and *Penicillium* when favorable conditions for their formation prevail. No region of the world escapes mycotoxins and their negative impact on animal and human health. The negative effect of mycotoxin contamination upon grain supplies and animal productivity are enormous and the risk to human health is ever-present. Warmer climates tend to succumb to aflatoxins and fumonisins while cooler areas with higher moisture are subject to ochratoxin, sporidesmin, zearalenone, deoxynivalenol, T-2 toxin, and diacetoxyscirpenol.

Mycotoxins are secondary metabolites produced by molds and fungi contaminating cereal grains as well as forages, fruits, feed and food products as well as the environment (e.g., soil, water and air through aerosol acquired mycotoxicosis, etc.). Mycotoxins have dangerous effects on human and animal health. Because mycotoxins are present throughout the food chain, mycotoxins are subject to regulation that limits excessive contamination of feed/food material and the environment based on the toxicological properties of the different groups of toxins (See e.g., Commission Recommendation of 17 Aug. 2006 on the presence of deoxynivalenol, zearalenone, ochratoxin A, T-2 and HT-2 and fumonisins in products intended for animal feeding. Official Journal of the European Union (2006/576/EC)). In this respect, different safety agencies around the globe have established limit values and control procedures to test for the level of contamination. These regulations are not yet harmonized between countries and/or continents and are also prone to the political and economical status of the geographical area that is considered. The regulations, where available, are founded on a non-exhaustive number of reports related to acute intoxication cases produced with crystalline forms of mycotoxins on model situations. As an understanding of mycotoxins progresses, the impact of chronic exposure level, the duration of the exposure and the co-occurrence of different mycotoxins naturally contaminated feed/food materials and the environment that can exert synergic toxic effects, might play an important role in the health status of animals and humans and their susceptibility to various other infections and thus immune status. In this perspective, solutions have to be considered to handle the non-regulated levels of toxic compounds that enter the food chain and are present in the environment. Accordingly, in some embodiments of the invention, an economical, large scale method for the preparation of high affinity, synthetic sorbent for the removal of mycotoxins (e.g., including, but not limited to, the entire family of major or minor classes of mycotoxin molecules including: Aflatoxins: aflatoxin B1, B2, G1, G2, M1, P1, Q1, sterigmatocystin and subfamilies, aflatoxicol; Trichothecenes: deoxynivalenol, diacetoxyscirpenol, monoacetoxyscirpenol, scirpenetriol, T-2 toxin, HT-2 toxins, T-2 tetraol, fusarenon X, fusarin C, fusaric acid, fusarochromanone, aurofusarin, fusaproliferin, neosolaniol, nivalenol along with metabolites and sub-families; Fumonisins: fumonisin A1, A2, B1, B2, B3 and subfamilies; Ochratoxins: ochratoxin A, B, α, β and metabolites; Zearalenone, zearalenol α, β, zearalanone, zearalanol α, β, zeranol and metabolites; Patulin, gliotoxin, mycophenolic acid, moniliformin cyclopiazonic acid, citrinin, beauvericin, citreoviridin, citochalasin H; Penicillic acid, PR-toxin, roquefortine A, B, rubratoxin and subfamilies; Ergot alkaloids: ergotamine, clavine alkaloids; Isofumigaclavines A, B; paspalitrem A, B, aflatrem, penitrems and subfamilies; Phomopsins: Phomopsin A and subfamilies; Verrucarin A, verruculogen and subfamilies; Sporidesmin and subfamilies; slaframine, swainsonine, tenuazoic acid, alternariol, and wortmannin).

Ochratoxin A (abbreviated as OTA) is the mycotoxin metabolite principally produced by *Aspergillus ochraceus* and *Penicillium verrucosum* among other mold species which can grow on improperly stored food products (See e.g., Pfohl-Leszkowicz A., and Manderville R. A., 2007. Molecular Nutrition and Food Research, 51: 61-99), contaminated grain, coffee beans (See e.g., O'Brien E., and Dietrich D. R. 2005. Critical Reviews in Toxicology, 35: 33-60), wine grapes (See e.g., Blesa J., Soriano J. M., Moltó J. C., Mañes J., 2006. Critical Review in Food Science and Nutrition, 46: 473-478), and might be transferred and contaminate liquids and solids consumed by humans (e.g., grape juice, wine, beer, coffee, cocoa extracts, as well as foods and feeds which utilize contaminated grains and meat and other byproducts from animals (e.g., milk, eggs, etc.) that consume contaminated grains or are otherwise exposed to mycotoxins) which can be detrimental to humans OTA is a carcinogenic (Group 2B; See e.g., Clark H. A., and Snedeker S. M, 2006. Journal of Toxicology and Environmental Health, Part B: Critical Reviews, 9: 265-96), nephrotoxic compound and can cause immunosuppression (See e.g., Al-Anati L., and Petzinger E., 2006. Journal of Veterinary Pharmocology and Therapeutics, 29: 79-90; Pfohl-Leszkowicz and Manderville, 2007 as cited previously; O'Brien and Dietrich, 2005 as cited previously). OTA can induce changes in the renal function of pigs including alteration of urine excretion, and increases of the excretion of glucose into urine, which has been characterized as the porcine nephropathy. Chicken, turkeys and ducklings fed with grains containing OTA have poor feed conversion and reduced egg production. In humans, OTA pathology has been clinically described as the Balkan endemic nephropathy (See e.g., Vrabcheva T., Petkova-Bocharova T., Grosso F., Nikolov I., Chemozemsky I. N., Castegnaro M., and Dragacci S., 2004. Journal of Agricultural and Food Chemistry, 52:2404-2410). Animal studies indicate that due to its similarity to phenylalanine, after its absorption at the level of the gastrointestinal tract, OTA can enter the enterohepatic circulation and bind the albumin fraction in blood and thus persist in animal tissues for extended period of times (See e.g., Creppy E. E., kane A., Dirheimer G., Lafarge-Frayssinet C., Mousset S., and Frayssinet C., 1985. Toxicology Letters, 28: 29-35.).

Another class of fungal toxins, the epipolythiodioxopiperazines including gliotoxin, hyalodendrin, sirodesmin, chaetomin, chaetocin, verticillins, leptosin, emestrin, and sporidesmin is of particular interest. The latter, generally of high economical impact on animal production, was found in specific areas of the world, primarily in New Zealand pastoral agriculture (See e.g., Hohenboken W. D., Morris C. A., Munday R., De Nicolo G., Amyes N. C., Towers N. R. and Phua S. H., 2004. New Zealand journal of Agricultural Research, 47: 119-127) but has also been reported in the Azores Islands of Portugal. Sporidesmin is a hydrophobic molecule synthesized by *Pithomyces chartarum* that is infesting certain grasses. The toxicity is induced by the presence of a disulphide bridge, which can inactivate proteins via the reaction with thiol groups and the generation of reactive oxygen species (superoxide radical, hydrogen peroxide, hydroxyl radical). This pathology is better known as facial eczema, a hepatogenous photosensitization resulting from the destruction of bile duct epithelial cells which causes phylloerythin (a metabolite of chlorophyll) to accumulate in the circulating blood and absorbing energy from sunlight, and particularly affecting sheep, cattle, horses, and deer. The clinical signs include decreases in milk production, weight loss, photosensitization, and death (See e.g., Munday R., 1982. Chemico-Biological Interactions, 41: 361-374). In addition to exposure to mycotoxins in feed, food, pastures and liquids, animals and humans come into contact with, and can become affected by mycotoxins in other ways. For example, animals can come into contact with mycotoxins in their bedding, fish can come into contact with mycotoxins in their water environment, and other organic materials can be affected by mycotoxins.

Mycotoxin contamination is unavoidable, and in order to reduce the negative effects of mycotoxins, inorganic materials such as clays, bentonites and aluminosilicates, or activated charcoal, known for their adsorptive properties, were historically used in agriculture (e.g., admixed with animal feed and/or ingredients, encapsulated forms or as filter devices). Clays used in large quantities sequester some mycotoxins in fluids (e.g., in the gastrointestinal tract of the animal and/or humans) and minimize their toxic effects (See e.g., Ramos A. J., and Hernandez E., 1997. Animal Feed Science and Technology, 65: 197-206; Grant P. G., and Phillips T. D., 1998. Journal of Agricultural and Food Chemistry, 46: 599-605). However, clays hinder the absorption of many beneficial nutrients that are important to animals and humans such as vitamins, minerals and amino acids thereby decreasing the nutrient density of the diet. Moreover, clays are an inert material that must be used (e.g., fed to animals) in large quantities to have a beneficial effect (e.g., reduction of mycotoxin contamination). However, clays fed to animals in large quantities can have a negative effect on the environment when the clays are excreted from the animal. Other broad spectrum mycotoxin adsorbents, which lack specificity for specific mycotoxins, including the invention described in U.S. Pat. No. 6,045,834, have also been used.

In general, molecular imprinted polymers (abbreviated as MIP's), are polymers that are formed in the presence of a molecule, the template, that is extracted afterwards, thus leaving complementary cavities behind. These polymers show a certain chemical affinity for the original molecule and can be used to fabricate sensors, catalysis or for separation methods. The first imprinted material was sodium silicate based. The first experimental use of these materials was for separation of dyes in 1949 (See e.g., Andersson H. S., and Nicholls I. A., 2001. In: Molecularly Imprinted Polymers: Man-made mimics of antibodies and their application in analytical chemistry, (Sellergen B., ed.), Techniques and Instrumentation in Analytical Chemistry, Vol. 23 Elsevier, Amsterdam, the Netherlands, pp. 1-19).

The present invention relates generally to molecularly imprinted polymers (MIPs). In particular, the present invention relates to reusable, ecologically friendly MIPs, methods of producing the same, methods of utilizing the same (e.g., to sequester and/or adsorb target compounds (e.g., mycotoxins)), and methods for applying the use in different ways (e.g., to detect presence of mycotoxins for traceability purposes and to remove mycotoxins from a contaminated source). Compositions and methods of the invention find use in a variety of applications including dietary, therapeutic, prophylactic, food and beverage processing and manufacture, liquid filtering as well as research and quality control applications.

Accordingly, in some embodiments, the present invention provides template compounds (e.g., upon which MIP are synthesized) that impact high sorption capacity and selectivity of MIPs for targeted compounds (e.g., mycotoxins). Template compounds are removable from the MIP post MIP synthesis (e.g., thereby "activating" the MIP and enabling it to bind to and adsorb target compounds (e.g., mycotoxins)). Thus, the present invention provides processes (e.g., a synthetic process) and materials that allow large scale production of template and MIP, that is not only economical (e.g., that enables realizable, large scale production in an economically achievable manner), but that also uses reagents that are more readily available than MIP templates historically used. The present invention also provides, in some embodiments, compositions (e.g., template compounds, monomers, cross-linkers as well as MIPs) that are bio-neutral (e.g., are not environmentally harmful). For example, in some embodiments, monomers and cross linkers of the invention are able to form high affinity, reversible complexes with template (e.g., with functional groups of the template), thereby producing MIPs with high affinity for target compounds (e.g., mycotoxins) and that provide positive effects on the environment (e.g., high water sorption properties whereby the MIP's adsorb up to 10 times more water than their weight thereby benefiting soil hydration by retaining water). Similarly, in some embodiments, the present invention provides MIPs with high affinity toward target compounds (e.g., mycotoxins) that are reusable (e.g., that can be separated from target compounds and reused).

I. Templates Used for Synthesis of Molecularly Imprinted Polymers (MIPs)

General schemes for MIP synthesis include steps for polymerization and cross-linking of monomers in the presence of template molecules that direct the formation of binding sites within the MIP network. Geometric specificity is imparted to MIP binding sites in steps analogous to the use of wax sculpture copies for the preparation of molds during the artistic technique of lost-wax casting. After the MIP network is formed, the template is removed so that the template-free MIP is available for sequestration of target compound. In some embodiments, removal of template is achieved through a series of washing steps (e.g., using those described in Section IV below).

In some embodiments, a target compound is used as a template. However, this raises the potential problem of template bleeding, or a gradual leaching of residual template into a sample. In analytical applications, template bleeding causes erroneously high background, while in non-analytical (e.g., sequestration) applications, template bleeding can confound sequestration efforts by actually introducing target molecules into the sample. Furthermore, for example when synthesizing MIPs that are directed towards targets with toxic and/or carcinogenic properties (e.g., mycotoxins), utilizing less hazardous template molecules during the MIP synthesis process may be desired from the standpoint of personal safety as well as to minimize hazardous waste. In preferred embodiments, the template molecule is non-hazardous and/or easily degraded, and therefore does not represent a health or environmental risk. In preferred embodiments, the template is reusable upon release from the MIP. In preferred embodiments, the template can be produced in larger quantities and in a safer manner than mycotoxins can be produced.

Therefore, in some embodiments, a template used for MIP synthesis may be the same compound as the desired target compound. In some embodiments, a template used for MIP synthesis may be different from the desired target compound. In preferred embodiments of the present invention, the desired target compound is a mycotoxin. Examples of mycotoxins include but are not limited to Aflatoxins: aflatoxin B1, B2, G1, G2, M1, P1, Q1, sterigmatocystin and subfamilies, aflatoxicol; Trichothecenes: deoxynivalenol, diacetoxyscirpenol, monoacetoxyscirpenol, scirpenetriol, T-2 toxin, HT-2 toxins, T-2 tetraol, fusarenon X, fusarin C, fusaric acid, fusarochromanone, aurofusarin, fusaproliferin, neosoloniol, nivalenol and metabolites and sub-families as well as conjugates; Fumonisins: fumonisin A1, A2, B1, B2, B3 and sub-families as well as conjugates; Ochratoxins: ochratoxin A, B, α, β and metabolites; Zearalenone, zearalenol, α- and β-zearalanone, zearalanol, α- and β-zeranol and metabolites as well as conjugates; Patulin, mycophenolic acid, moniliformin, cyclopiazonic acid, citrinin, beauvericin, citreoviridin, citochalasin H; gliotoxin, sporidesmin, hyalodendrin, sirodesmin, chaetomin, chaetocin, verticillins, leptosin, emestrin, and subfamilies; Penicillic acid, PR-toxin, roquefortine A, B, rubratoxin and subfamilies; Ergot alkaloids: ergotamine, ergocryptine, ergovaline, ergocristine, ergometrine, ergosine, ergonine, ergocornine, ergine, lysergol, lysergic acid, and epimers clavine alkaloids; Isofumigaclavines A, B; paspalitrem A, B, aflatrem, penitrems and subfamilies; Phomopsins: Phomopsin A and subfamilies; Verrucarin A, verruculogen and subfamilies; slaframine, swainsonine, tenuazoic acid, alternariol, and wortmannin. In certain embodiments, the target compound is OTA, sporidesmin, ergot alkaloids.

In some embodiments, the design and/or determination of a non-target template compound is performed by careful structural analysis of the target molecule, structural minimization, and determination of structural features and functional groups critical for effective MIP binding site formation. Methods for structural minimization are known in the art (See e.g., Baggiani C., Giraudi G., and Vanni A., 2002. Bioconjugation, 10: 389-394; herein incorporated by reference in its entirety). While the present invention is not limited to any particular mechanism, and an understanding of the mechanism is not necessary to practice the present invention, structural considerations that are taken into account during template design include but are not limited to chirality, planarity, the elimination of structures responsible for undesired properties of the molecule (e.g., elimination of molecular determinants of toxicity), and/or the existence of an appropriate solvent-accessible surface, electrostatic potential surface, and/or lypophilic-hydrophilic surface of the template molecule and its potential interactions with monomers and crosslinker as well as simplicity of the template synthesis. In some embodiments, ultrafast shape recognition techniques are applied to enable the routine screening for compounds that most closely resemble a molecule according not only to an outperforming two-dimensional structure recognition but preferentially one of the most discriminating pattern, that is to say, the tri-dimensional molecular shape (See, e.g., Balletser P., and Richards W. G., 2007. Proceedings of the Royal Society A: Mathematical, Physical and Engineering Sciences, 463: 1307-1321.

In one non-limiting example, a template for Ochratoxin A is N-(2-hydroxy-3,5-dichlorobenzoyl)-L-phenylalanine, as shown in FIG. 1.

Figure 2:
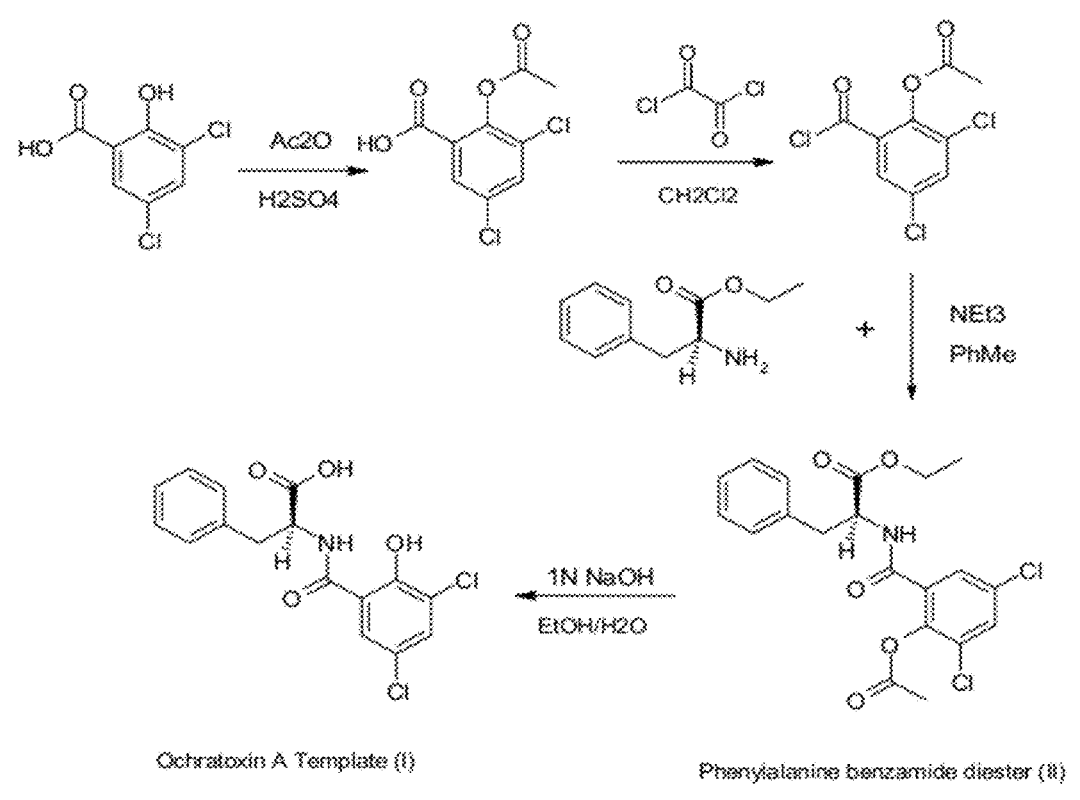

In one non-limiting example of a synthesis method for N-(2-hydroxy-3,5-dichlorobenzoyl)-L-phenylalanine, synthesis begins with reaction of 3,5-dichlorosalicylic acid with acetic anhydride to obtain 2-acetoxy-3,5-dichlorobenzoic acid which in turn is converted into the acid chloride by the action of oxalyl chloride. The 2-acetoxy-3,5-dichlorobenzoic acid chloride is then reacted in situ with phenylalanine ethyl ester hydrochloride, in the presence of triethylamine, to yield ethyl ester of N-(2-acetoxy-3,5-dichlorobenzoyl)-L-phenylalanine. The last step of the synthesis method introduces novel and highly specific hydrolysis of both ester functions of N-(2-acetoxy-3,5-dichloro benzoyl)-L-phenylalanine ethyl ester to obtain the OTA template, N-(2-hydroxy-3,5-dichlorobenzoyl)-L-phenylalanine (I) with 98% yield. This synthesis reaction is summarized in FIG. 2.

Thus, the present invention provides processes and materials for the synthesis of templates (e.g., OTA templates) that are scalable to large quantities in an economically achievable manner.

II. Monomers and Cross-linking Agents Used for Polymerization of MIPs

Selection of monomers used in the synthesis of MIPs take into account structural features of the template molecule in order to assess which monomer or combination of monomers is most likely to form interactions (e.g., covalent, non-covalent, ionic, hydrogen bonds, hydrophobic interactions, Van der Waals interactions) with the template. In one non-limiting example, key structural features of the OTA template (I) described herein (e.g., N-(2-hydroxy-3,5-dichlorobenzoyl)-L-phenylalanine) include (i) the two acidic functional groups (—OH and —CO$_2$H); (ii) one strongly polar peptide group (—NHCO—); (iii) and several low polarity hydrocarbon fragments of the template structure (e.g., each of which has the potential to form complexes with the monomers and the cross-linker molecules). U.S. patent application Ser. No. 10/181,435, herein incorporated by reference in its entirety, describes MIP functional monomers and methods of computational monomer selection (See, e.g., Baggiani et al., 2002 as previously cited).

Classes of monomers and specific monomers (e.g., utilized in MIP synthesis methods of the invention) include, but are not limited to, the following classes and derivatives thereof: acrylic acid and derivatives (e.g., 2-bromoacrylic acid, acryloyl chloride, N-acryloyl tyrosine, N-acryoyl pyrrolidinone, trans-2-(3-pyridyl)-acrylic acid), acrylates (e.g., alkyl acrylates, allyl acrylates, hydroxypropyl acrylate), methacrylic acid and derivatives (e.g., itaconic acid, 2-(trifluoromethyl) propenoic acid), methacrylates (e.g., methyl methacrylate, hydroxyethyl methacrylate, 2-hydroxyethyl methacrylate, 3-sulfopropyl methacrylate sodium salt, ethylene glycol monomethacrylate), styrenes (e.g., (2, 3 and 4)-aminostyrene, styrene-4-sulfonic acid, 3-nitrostyrene, 4-ethystyrene), vinyls (e.g., vinyl chloroformate, 4-vinylbenzoic acid, 4-vinylbenzaldehyde, vinyl imidazole, 4-vinylphenol, 4-vinylamine, acrolein), vinylpyridines (e.g., (2, 3, and/or 4)-vinylpyridine, 3-butene 1,2-diol), boronic acids (e.g., 4-vinylboronic acid), sulfonic acids (e.g., 4-vinylsulfonic acid, acrylamido-2-methyl-1-propane-sulphonic acid), metal chelators (e.g., styrene iminodiacetic acid), acrylamides and derivatives (e.g., N-methyl acrylamide), methacrylamides and derivatives (e.g., N,N-dimethyl acrylamide, N-(3-amino-prpoyl)methacrylamide), alkenes (e.g., 4-pentenoic acid, 3-chloro-1-phenyl-1-propene) (meth)acrylic acid anhydride and derivatives (e.g., methacrylic anhydride), silicon-containing monomers (e.g., (3-methacryloxypropyl) trimethoxy silane, tetramethyldisiloxane), polyenes (e.g., isoprene, 3-hydroxy-3,7,11-trimethyl-1,6,10-dodecatriene), azides (e.g., 4-azido-2,3,5,6-tetrafluorobenzoic acid), thiols (e.g., allyl mercaptan). Acrylate terminated or otherwise unsaturated urethanes, carbonates and epoxies can also be used in embodiments of the present invention, as can silicon-based monomers.

In preferred embodiments, monomers and the crosslinker used for synthesis of MIPs directed towards a template for OTA (i.e., N-(2-hydroxy-3,5-dichlorobenzoyl)-L-phenylalanine) comprise 2-vinylpyridine, 2-hydroxyethyl methacrylate and/or ethylene glycol dimethacrylate. While the present invention is not limited to any particular mechanism, and an understanding of the mechanism is not necessary to practice the present invention, 2-vinylpyridine forms ionic bonds with the acidic groups of the template, and contains the vinyl bond in a close proximity to the basic nitrogen atom of the pyridine ring. This interaction between the template and the 2-vinylpyridine promotes formation of the polymer in very close vicinity of the template molecule and enables a tight bonding between the MIP and OTA in the MIP (e.g., after template compound is removed and the MIP is allowed to interact with target OTA molecules). While the present invention is not limited to any particular mechanism, and an understanding of the mechanism is not necessary to practice the present invention, the hydroxyl group of 2-hydroxyethyl-methacrylate monomer forms additional hydrogen bonds with highly polar peptide bonds of the template. An additional reagent is ethylene glycol dimethacrylate. While the present invention is not limited to any particular mechanism, and an understanding of the mechanism is not necessary to practice the present invention, ethylene glycol dimethacrylate finds use in some embodiments as a cross-linking agent (see below), as an unsaturated diester that interacts with low polarity groups that are present in the OTA template molecule. In some embodiments, individual types of monomers are utilized individually or in combination with other types of monomers.

If utilized, the crosslinking agent or agents will preferably be one or several polymeric or oligomeric compounds, or a compound that provides for cleavage under specific conditions. Crosslinking agents that lend rigidity to the subject polymeric compounds are known to those skilled in the art, and include, but are not limited to, di-, tri-, tetra- and penta-functional acrylates, methacrylates, acrylamides, vinyls, allyls, and styrenes. Specific examples of cross-linking agents include but are not limited to p-divinylbenzene, ethylene glycol dimethacrylate (abbreviated as EGDMA), tetramethylene dimethacrylate (abbreviated as TDMA), N,N'-methylene bisacrylamide (abbreviated as MDAA), N,N'-1,3-phenylenebis(2-methyl-2-propenamide) (PDBMP), 2,6-bisacryloylamidopyridine, 1,4-diacryloyl piperazine (abbreviated as DAP), 1,4-phenylene diacrylamide, and N,O-bisacryloyl-L-phenylalaminol. Examples of reversible, cleavable crosslinkers include, but are not limited to, N,N'-bis-(acryloyl) cystamine, N,N-diallyltartardiamide, N,N-(1,2-dihydroxyethylene) bisacrylamide, N1-((E)-1-(4-vinylphenyl)methylidene)-4-vinylanilene, allyl disulfide, and bis(2-methacryloyloxyethyl))disulfide. In preferred embodiments, ethylene glycol dimethacrylate is used as a cross-linking agent. Although the preferred cross-linking monomer is ethylene glycol dimethacrylate, embodiments of the present invention are not limited to this agent, and other cross-linking monomers may be used, such as, divinylbenzene and trimethylolpropane trimethacrylate (abbreviated as TRIM).

Any ratio of simple monomers to crosslinking agents can be used that provides a MIP structure of appropriate integrity, e.g., that can be used in the context of the final application (e.g., in food or feed products, in water intended for aquaculture use, in vivo, etc). Those skilled in the art can select suitable ratios of monomers to provide the desired structural integrity, which is intimately related to the nature and structure of the targeted molecule and to the nature and structure of the template used.

In the case of polymeric or oligomeric compounds that are to be utilized in vivo (e.g., as therapeutics or diagnostics, or as consumable sequestration components of animal feed or human foodstuffs), it is important to select monomers that are non-toxic and which exhibit suitable in vivo stability and solubility. Preferred examples include, but are not limited to, acrylamides and methacrylates. Alternatively, the polymer may be treated post-polymerization to enhance the template solubility, e.g., by reaction with suitable organic or inorganic reagents.

Different polymerization methods may be used including free radical, cationic, and anionic polymerization. Polymerization conditions are selected and provided herein that do not adversely affect the active conformation of the compound for which a complementary polymeric compound is to be produced. In particularly preferred embodiments, free radical precipitation polymerization methods are used (see Section III below).

Additionally, polymerization of MIPs is typically begun by the addition of an initiating agent. Initiating agents include but are not limited to azo-bisisobutyronitrile (abbrevioated as AIBN), azo-bisdimethylvaleronitrile (abbreviated as ABDV), dimethylacetal of benzil, benzoylperoxide (abbreviated as BPO), and 4,4'-azo(4-cyanovaleric acid). In preferred embodiments, the initiating agent is azo-bisisobutyronitrile.

In preferred embodiments, monomers, crosslinkers, and/or MIPs have favorable safety and/or environmental properties such as reduced or no toxicity and high water sorption and retention. In preferred embodiments, MIPs can be reusable and economically realizable/producible.

III. Solvents Used for Synthesis of MIPs

The selection of solvent/solvent mixture in which the polymerization reaction is carried out has a profound impact on the scope, selectivity and specificity of the binding affinity of a MIP to its target compound. While the present invention is not limited to any particular mechanism, and an understanding of the mechanism is not necessary to practice the present invention, porosity is facilitated or provided by a porogenic solvent or solvent mixture that exhibits the following properties: it dissolves in the monomer mixture, is inactive to the polymerization reaction and does not dissolve the polymer (MIP) produced. Suitable porogenic solvents include, but are not limited to, aromatic hydrocarbons, such as toluene, xylene, ethylbenzene and diethylbenzene; nonpolar solvents, such as cyclohexane; saturated hydrocarbons, such as hexane, heptane, octane and decane; alcohols, such as isopropyl and isoamyl alcohol; aliphatic halogenated hydrocarbons, such as dichloromethane, dichloroethane and trichloroethane; aliphatic or aromatic esters, such as ethyl acetate, butyl acetate, dimethylphthalate. In preferred embodiments, aromatic hydrocarbon solvents are used. In particularly preferred embodiments, toluene is used alone. In some embodiments, a mixture of toluene with another solvent is used. In some embodiments, toluene is used in combination with cyclohexane. The porogenic solvents can be used individually or in combinations of two or more. The amount of the porogenic solvent added can be varied from about 10% to 500% by mass based on the total amount of the monomers. While the present invention is not limited to any particular mechanism, and an understanding of the mechanism is not necessary to practice the present invention, polar solvents (e.g., water, acetonitrile) disrupt tight complexes between monomers and template, thereby lowering MIP specificity for target molecule binding (e.g., as in toluene, etc.

The solvent or the solvent mixture used as a medium for MIP synthesis also has an impact on the swelling properties of MIP and on the size of pores within the tri-dimensional MIP network. In certain embodiments, polar solvents such as acetonitrile are used as a solvent or co-solvent for MIP polymerization when an increase in MIP swelling and increase of MIP pore size is desired; alternatively, such solvents are avoided when an increase in MIP swelling and MIP pore size is not desired (e.g., when MIP is intended for use as a chromatographic column where swelling may impede flow rate and disturb the elution of analytes and the ability of the HPLC instrument to perform).

Judicious choice of solvent system may directly affect MIP pore size. In non-limiting examples, during synthesis of a MIP directed to a template of OTA, the smallest particles (1-20 μm) were formed in low polarity solvents like cyclohexane and/or toluene, while much larger and less size homogenous (10-170 μm) particles were formed in polar solvents like acetonitrile or water. Furthermore, at high concentrations of monomers, the polymerization reaction yields large MIP clusters which are easily dispersed by grinding, without production of very fine particles as occur during grinding of MIP monoliths (see detailed discussion in Section IV below). Very fine particles may be undesirable in applications where, for example, a MIP is intended for use as a column resin (where fine particles may impede flow rate) or when the presence of fine particles impedes or complicates collection of MIPs during centrifugation or filtration or disturbs the appropriate confinement of the MIP in the case of filtration, which is consequently governed by the pore size of the specific mesh filter that incorporates the MIP, if the filter should preserve the amount of MIP enclosed. Dispersed MIP clusters may be sieved to provide products of defined, homogeneous size. Therefore, the choice of polymerization solvent, monomer concentration, and physical handling methods may be chosen to result in an optimal yield of MIPs with desired pore size and particle size, while avoiding formation of fine particles.

The choice of solvent system dictates the physical form of the MIP that is formed during the polymerization process. For example, some solvent systems (including but not limited to low polarity solvents such as cyclohexane and/or toluene) yield, as described above, solid MIP clusters during a process referred to as precipitation polymerization. Other solvent systems (including but not limited to polar solvents such as polyvinyl alcohol in water) promote a kinetically distinct process referred to as emulsion polymerization (Vivaldo-Lima E., Wood P. E., Hamielec A. E., 1997. Industrial and Engineering Chemistry Research, 36: 939-965). In general, the nature of polymerization affects both the physical form of the MIP network and the ease with which it may be processed further (e.g., the need for grinding; uniformity of particle size; yield; ease of buffer or solvent exchange; stability). Polymerization processes are reviewed in Yan H., and Ho Row K., 2006. International Journal of Molecular Science, 7: 155-178; herein incorporated by reference in its entirety. In preferred embodiments, precipitation polymerization is used. In certain embodiments, precipitation polymerization results in a MIP product that forms as a powder of uniform and easily manageable particle size. In comparison, other polymerization methods including but not limited to bulk polymerization may yield a large monolith of MIP that must be crushed prior to further processing or use, and resulting in irregular particle sizes and consequently lower performance.

IV. Methods to Remove Template from MIP Following MIP Synthesis and Physical Processing of MIPs Techniques used for dissociation of template from newly-synthesized MIP are generally determined by the nature of the template-MIP interaction. For example, when covalent bonds have formed between template and the MIP network, chemical cleavage of the template from MIP is required. In contrast, when interaction between template and the MIP network is non-covalent, solvent extraction may be sufficient to remove the template (See, e.g., Yan H., and Ho Row K., 2006 as previously cited and herein incorporated by reference in its entirety; Sellergren B., 2001. *The non-covalent approach to molecular imprinting*. In: Molecularly Imprinted Polymers Man-made mimics of antibodies and their application in analytical chemistry, (Sellergen B., ed.), Techniques and Instrumentation in Analytical Chemistry, Vol. 23 Elsevier, Amsterdam, the Netherlands, pp. 113-184). Post-synthesis processing of MIPs may also be referred to as MIP activation. In preferred embodiments, a first step of MIP activation involves decanting and then evaporating (recycling) the solvent from MIP material, under slightly reduced pressure (e.g., using a rotary evaporator system). A second step involves grinding of the MIP particles to yield a smaller particle size (e.g., using a mortar and pestle or milling equipment). A third step involves multiple washes of the MIP particles, e.g., with 0.2 w/v % sodium hydroxide. In embodiments in which an OTA MIP is synthesized, the thoroughness of washing may be tracked until a negative test is obtained with $FeCl_3$ solution for detection of template (see Example 2 to Example 4). In some embodiments, a single wash with 1% acetic acid and single wash with water is followed by drying of the final MIP product (e.g., at 80° C. in a drying oven for 6-8 h) until all traces of solvent are removed. Finally, MIP particles may be sieved to provide product of defined particle size. In preferred embodiments, the physical form of the MIP does not require extensive grinding prior to use, e.g., the MIP does not form monolithic blocks that require crushing or grinding for dispersal. In preferred embodiments, the majority of the MIP forms spheres that form a powder upon drying.

In preferred embodiments, washing steps are sufficient to remove at least 95% of the template molecule from the MIP network. In particularly preferred embodiments, washing steps are sufficient to remove at least 99% of the template molecule from the MIP network. In most preferred embodiments, washing steps are sufficient to remove at least 99.9% of the template molecule from the MIP network.

V. Application of MIP Compositions

Compositions and methods of the invention find use in a variety of applications including dietary, therapeutic, prophylactic, food and beverage processing and manufacture, as well as research and quality control applications. For example, in some embodiments, synthetic templates (e.g., generated using methods described herein) are utilized for MIP synthesis. The present invention is not limited to any particular synthetic template and/or MIP synthesized. Indeed, a variety of synthetic templates can be generated and utilized including, but not limited to, an OTA template (e.g., N-(3,5-dichloro-2-hydroxybenzoyl)-L-phenylalanine, See Example 1), template(s) for aflatoxin(s), a trichothecene template (e.g., sesquiterpene alcohol template (e.g., deoxynivalenol (DON) template)), a zearalenone template, a sporidesmin template, a sterigmatocystin template, a fumonisin template, a patulin template, a citrinin template, and/or endophyte related ergot template. In some embodiments, the present invention provides compositions and methods for producing a synthetic template (e.g., for use in MIP OTA synthesis) that comprises exterior functional groups that resemble a mycotoxin (e.g., wherein the template is utilized to generate a MIP in a process of the invention and subsequently removed there from, the MIP displays high affinity for the mycotoxin resembled by the exterior functional groups), wherein the mycotoxin is selected from the group comprising acetoxyscirpenediol, acetyldeoxynivalenol, acetylnivalenol, acetylneosolaniol, acetyl T-2 toxin, extended to all aflatoxins, aflatoxin B1, B2, G1 and G2, aflatrem, altenuic acid, alternariol, austdiol, austamide, austocystin, avenacein +1, beauvericin +2, bentenolide, brevianamide, butenolide, calonectrin, chaetoglobosin, chaetocin, chaetomin, citrinin, citreoviridin, cochliodinol, cytochalasins, cyclopiazonic acid, deacetylcalonectrin, deactylneosolaniol, deoxynivalenol diacetate, deoxynivalenol monoacetate, diacetoxyscirpenol, destruxin B, emestrin, enniatins, extended to all ergot alkaloids toxins and endophytes such as ergine, ergocornine, ergocristine, ergocryptine, ergometrine, ergonine, ergosine, ergotamine, ergovaline, lysergol, lysergic acid, and related epimers, fructigenin +1, fumagilin, fumonisins, fumonisins A1, A2, B1 and B2 and B3, fusarenon-X, fusarochromanone, fusaric acid, fusarin, gliotoxin, HT-2 toxin, hyalodendrin, ipomeanine, islanditoxin, isofumigaclavines A and B, lateritin +1, leptosin, lycomarasmin +1, malformin, maltoryzine, moniliformin, monoacetoxyscirpenol, mycophenolic acid, neosolaniol, nivalenol, NT-1 toxin, NT-2 toxin, extended to all ochratoxins, oosporein, oxalic acid, paspalitrem A and B, patulin, penicillic acid, penitrem, phomopsins, PR-toxin, roridin E, roquefortine A and B, rubratoxin, rubroskyrin, rubrosulphin, rugulosin, sambucynin +1, satratoxins, F,G,H, scirpentriol, sirodesmin, slaframine, sporidesmin, sterigmatocystin, swainsonine, T-1 toxin, T-2 toxin, tenuazoic acid, triacetoxyscirpendiol extended to all trichothecenes, trichodermin, trichothecin, trichoverrins, trichoverrols, tryptoquivalene, verrucarin, verruculogen, verticillins, viopurpurin, viomellein, viriditoxin, wortmannin, xanthocillin, yavanicin +1, zearalenols, zearalanones, zearalenone, α, β, zearalanone, α, β, zeranol and subfamilies and/or derivatives of the same, and/or conjugates. In certain embodiments, the target compound is OTA, sporidesmin, or ergot alkaloids.

Similarly, a variety of MIPs can be generated and utilized including, but not limited to, a MIP generated utilizing any one of the above mentioned synthetic templates or any other organic molecule as a template (e.g., nutrient such as vitamins, drugs, antibiotics, contaminants, hormones, enzymes, proteins, etc.).

MIPs described herein find use in a variety of applications. For example, in some embodiments, MIPs are utilized for purification of liquids. For example, in some embodiments, MIPs are utilized to selectively remove target compounds (e.g., one or more mycotoxins) from a liquid. The present invention is not limited by the target compounds (e.g., one or more mycotoxins) removed from liquid. Indeed, a variety of target compounds may be removed including, but not limited to, mycotoxins described herein. Similarly, the present invention is not limited by the type of liquid from which a target compound is removed. Indeed, a variety of different liquid solutions can have one or more target compounds (e.g., mycotoxins) removed there from (e.g., by administering one or more different types of MIPs to the solution) including, but not limited to, beverages (e.g., consumed by humans (e.g., juice, wine (e.g., white wine, red wine, etc.), water, beer, tea, coffee, etc.)), water (e.g., used in aquaculture, drinking water, etc.), liquids utilized in the production of foodstuffs (e.g., human, animal foodstuffs), biological fluids (e.g., blood, rumen fluid, stomach fluid, etc.), etc.

For example, in some embodiments, compositions and methods described herein provide MIPs that selectively remove target compounds (e.g., mycotoxins) from a liquid. The liquid can be a beverage, water, biological sample, potable water supply, blood, rumen fluid, or other type of liquid that contains target compounds. Additionally, target compounds can be removed from other types of fluids. In some embodiments, MIPs described herein are contacted with (e.g., mixed with) a liquid for a sufficient amount of time that allows the MIP to interact with and bind to a target compound (e.g., mycotoxin). Although an understanding of the mechanism is not necessary to practice the present invention and the present invention is not limited to any particular mechanism, in some embodiments, after the liquid is allowed to interact with the MIP, complexing/binding cavities contained in the MIP (e.g., cavities remaining after the template molecule is removed from the MIP) bind target compound upon contact, effectively removing the target compound from the liquid. The liquid can then be further processed, packaged, or made ready for consumption (e.g., for human consumption, for animal consumption, or for animal habitats). In some embodiments, MIPs generated and/or provided herein possess a rigid structure that withstands physical and chemical forces associated with the removal/sequestration process. For example, in a preferred embodiment, a MIP provided herein binds selectively to a target compound, thereby removing the target compound from a substance (e.g., liquid, solid surface, biological fluid (e.g., blood, rumen fluid, etc.), necessary to sustain life (e.g., air or aquaculture medium), etc.), and maintains association with the target compound as the MIP-target compound complex is collected and/or removed from the substance (e.g., pumping liquid through a filter, pouring liquid through a filter, dipping a filter into a liquid, coating the MIP on the surface of a container, centrifugations, coating the MIP on the surface of a filter, animal feces excretion, etc.).

In one embodiment, a method of removing target compounds from a liquid is highly selective. For example, a liquid may contain a multitude of target compounds wherein the MIP selectively removes only one specific target compound (e.g., mycotoxin), where "one" refers to the type of target compound and not the number of target compounds removed. In some embodiments, a plurality of MIPs (e.g., a plurality of different populations of MIPs (e.g., wherein one population of MIPs is specific for one type of mycotoxin (e.g., ochratoxin) and a second population of MIPs is specific for a second type of mycotoxin (e.g., aflatoxin) are administered to a liquid and allowed to interact for a sufficient amount of time to selectively remove a plurality of different types of target compounds (e.g., mycotoxins) from the liquid. The present invention is not limited by the number of different types of MIPs that are administered to a liquid comprising a plurality of different types of target compounds (e.g., mycotoxins). In some embodiments, a liquid comprises 2, 3, 4, 5, 6, 7, 8, 9, 10, 11, 12 or more different types of target compounds (e.g., mycotoxins), to which a composition comprising 2, 3, 4, 5, 6, 7, 8, 9, 10, 11, 12, or more different types of MIPs with specificity for one of the plurality of target compounds are administered to the liquid under conditions such that the MIPs interact with and sequester the target compounds. In some embodiments, a MIP displays specific affinity for a single target molecule/compound. In some embodiments, a MIP displays specific affinity for a group of molecules having a common chemical or physical property. In some embodiments, a MIP possesses a plurality of different complexing/binding cavities for different target compounds such that the MIP is able to selectively bind multiple target compounds, following the use of a plurality of target molecule/compound when processing the MIP.

In some embodiments, the present invention provides a method of removing target compounds from a liquid comprising a plurality of different types of target compounds (e.g., mycotoxins or other organic molecule target molecule/compound (e.g., nutrient such as vitamins, drugs, antibiotics, contaminants, hormones, enzymes, proteins, etc.)). In some embodiments, the method includes a group of different types of MIPs designed to bind different target compounds. For example, in some embodiments, a sample of a liquid is provided wherein an assay is performed to identify the presence of one or more target compounds in the liquid sample. The presence of specific mycotoxins can be detected in order to determine which mycotoxins are present. Upon identification of the one or more types of target compounds present in the liquid sample (e.g., wherein the liquid sample is representative of the characteristics of the liquid from which the sample was taken), one or more MIPs are generated (e.g., according to methods described herein) and/or combined, and then the one or more MIPs are administered to the liquid solution to remove target compounds. In some embodiments, identification of the one or more types of target compounds comprises use of columns and/or filters comprising one or more MIPs specific for target compounds. In some embodiments, once a MIP is utilized for removal of target compound from a sample (e.g., a liquid sample), the target compound is removed from the MIP and the MIP is reused. In some embodiments, the MIP is disposed of in an appropriate manner. For example, target compounds can be removed from a MIP (e.g., in order to make the MIP reusable) via washing with a suitable solvent and/or solution, that can be chosen from the solvents used in the methods to dissociate MIPs from the template following the synthesis reactions, and physical processing of MIPs (e.g., including but not limited to, acetonitrile, toluene, methanol, sodium hydroxide, acetic acid, etc.), or the like. The recycled MIPs are then returned to use.

Methods of removing target compounds from a liquid can produce high recovery yields because of the selective nature of MIPs. In some embodiments, a removal method recovers from about 25% to about 99% of the target compound present in a liquid. In some embodiments, a removal method recovers from about 35% to about 99% of the target compound present in a liquid. In some embodiments, a removal method recovers from about 50% to about 99% of the target compound present in a liquid. In some embodiments, a removal method recovers from about 75% to about 99% of the target compound present in a liquid. In other embodiments, a removal method lowers the resulting target compound concentration of the liquid to a level on the parts per billion (ppb) (e.g., to a concentration that is appropriate for human and/or animal consumption). Methods of removal can be tailored to provide specific concentration levels as found in current and proposed regulatory schemes known to those skilled in the art. In some embodiment, methods of removal are used on liquids with specific pH levels. For example, compositions and methods of the invention can be utilized with liquids having a pH between about 1 and 13.

In some embodiments, MIPs are utilized to remove target compounds from a surface. For example, certain embodiments of the present invention provide methods for decreasing the presence of target compounds (e.g., mycotoxins) on a surface comprising contacting the surface with a composition comprising a MIP. In specific embodiments, the contacting is performed for a time sufficient for the MIP to bind to and/or sequester target compounds. In other embodiments, the present invention provides a method of decontaminating an environmental surface harboring target compounds. In one such embodiment, the target compound is associated with an environmental surface and the method comprises contacting the environmental surface with an amount of a composition (e.g., comprising a MIP) sufficient for decontaminating the surface. While it may be so desired, decontamination need not result in total elimination of the target compound. In some embodiments, the compositions (e.g., comprising a MIP) and methods further comprise dyes, paints, and other marking and identification compounds so as to ensure that a treated surface has been sufficiently treated with a compositions of the present invention.

In some embodiments, MIP's are utilized to prevent a target compound from coming into contact with a surface or other compound (e.g., soil). For example, certain embodiments of the present invention contemplate methods for making compositions whereby MIP's are combined with other materials (e.g., plastic or starch type product) and applied to vegetation (e.g., growing agricultural vegetation) to protect the vegetation from surface compounds (e.g., mycotoxin) during growth and further preventing the compounds from contaminating other compounds (e.g., soil).

In certain embodiments, a surface (e.g., external or internal surface) of a subject (e.g., human or animal) is treated (e.g., externally or internally) with a composition of the present invention. In other embodiments, the contacting is via oral, nasal, buccal, rectal, vaginal or topical administration. When the present compositions are administered as pharmaceuticals, it is contemplated that the compositions further comprise pharmaceutically acceptable adjutants, excipients, stabilizers, diluents, and the like. In still further embodiments, the present invention provides compositions further comprising additional pharmaceutically acceptable bioactive molecules (e.g., antibodies, antibiotics, means for nucleic acid transfection, vitamins, minerals, co-factors, factors capable of binding to and/or sequestering mycotoxins (e.g., yeast cell wall extracts (e.g., yeast cell wall extracts combined with a clay material, and/or yeast cell wall extract containing clay and/or clay particles integrated and/or interlaced into the yeast cell wall), etc.). In some embodiments, a subject is administered a composition of the invention (e.g., comprising MIPs) in order to therapeutically treat a disease or condition (e.g., athlete's foot). In other embodiments, a subject is administered a composition of the invention (e.g., comprising MIPs) in order to prophylactically treat (e.g., prevent the onset of signs or symptoms of) a disease or condition (e.g., athlete's foot). In some embodiments, compositions (e.g., comprising MIPs) and methods are applied to any type of area or surface. For example, in some embodiments, the area comprises a solid surface (e.g., a medical device), a solution, the surface of an organism (e.g., an external or internal portion of a human), or a food product.

The present invention is not limited by the amount of one or more MIPs administered to (e.g., mixed with) a liquid or solid (e.g., for the removal of target compounds). In some embodiments, about 0.10 mg, 0.50 mg, 1.0 mg, 2.0 mg, 5.0 mg, 10.0 mg. 20.0 mg, 50.0 mg, 100.0 mg, 500.0 mg or more of a MIP is administered per liter of liquid or solid.

In some embodiments, a MIP of the present invention is used for a toxin elimination method such as hemoperfusion. Hemoperfusion is a treatment technique in which large volumes of a subject's blood are passed over an adsorbent substance (e.g., MIP) in order to remove toxic substances from the blood.

Normally, the sorbents most commonly used in hemoperfusion are resins and various forms of activated carbon or charcoal. However, binding specificity of these materials are relatively poor and sometimes they adsorb important blood factors as well as target molecules. Accordingly, in some embodiments, the present invention provides for the use of a MIP of the invention as more specific and high affinity sorbents for target molecules.

Hemoperfusion works by pumping the blood drawn through the arterial catheter into a column or cartridge containing the sorbent material (e.g., in some embodiments, the present invention provides that the sorbent material utilized is a MIP described herein). As the blood passes over the carbon or resin particles in the column, the toxic molecules or particles are drawn to the surfaces of the sorbent particles and trapped within the column. The blood flows out the other end of the column and is returned to the subject through the tubing attached to the venous catheter. Hemoperfusion is able to clear toxins from a larger volume of blood than hemodialysis or other filtration methods; for example, it can process over 300 mL of blood per minute.

A MIP of the present invention may be used for hemoperfusion. In some embodiments, MIPs of the invention are utilized to remove one or more mycotoxins from the blood of a subject using hemoperfusion.

Dosage regimens may be adjusted to provide the optimum desired response (e.g., a therapeutic or prophylactic response). For example, a single bolus containing MIP's may be administered to an animal, several divided doses may be administered over time or the dose may be proportionally reduced or increased as indicated by the exigencies of the therapeutic situation. It is advantageous to formulate parenteral compositions in dosage unit form for ease of administration and uniformity of dosage. The dosages of the MIPs of the present invention are generally dependent on (a) the unique characteristics of the active compound and the particular therapeutic or prophylactic effect to be achieved, and (b) the limitations inherent in the art of compounding such an active compound for the treatment of sensitivity to mycotoxins in individuals. The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

The MIPs of the invention can be incorporated into pharmaceutical compositions suitable for administration to a subject. For example, the pharmaceutical composition may comprise MIPs and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the MIPs.

In certain embodiments, the MIPs of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, pellets, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, MIPs of the invention are co-formulated with and/or co-administered with one or more additional therapeutic agents.

The pharmaceutical compositions of the invention may include a "therapeutically effective amount" or a "prophylactically effective amount" of the MIPs of the invention. A "therapeutically effective amount" refers to an amount effective, at dosages and for periods of time necessary, to achieve the desired therapeutic result. A therapeutically effective amount may vary according to factors such as the disease state, age, sex, and weight of the individual, and the ability of the imprinted nanoparticle to elicit a desired response in the individual. A therapeutically effective amount is also one in which any toxic or detrimental effects of the imprinted nanoparticle are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

In some embodiments, when admixed with organic matter (e.g., feedstuffs), and/or liquid (e.g., water, wine or other beverage) and/or fed directly to a subject, compositions of the present invention decrease the absorption or uptake of mycotoxins by the subject (e.g., thereby alleviating reduced performance, increasing health and/or reducing the incidence of mycotoxin-associated diseases or pathological responses in the subject) and reducing and/or preventing deposition of mycotoxins or their metabolites in meat, fish, eggs, milk and the other products destined to enter human food chain.

In some embodiments, the present invention is used to generate separation devices (e.g., solid-phase extraction (abbreviated as SPE)) that are used to remove solid or semi-solid compounds from a mixture of impurities based on their physical and chemical properties that is different from the conventional separation devices available (e.g., normal phase, reverse phase, or ion exchange-solid-phase extraction). In some embodiments, separation devices can be incorporated in a cartridge serving at extracting and consequently purifying the specific corresponding template and template analogs of the MIP produced.

In some embodiments, the present invention can serve for the packing of chromatographic column used with liquid chromatography and enabling the specific elution of corresponding template and template analogs of the MIP used. The MIP columns produced enables a more specific interaction than the available other techniques and materials known in the art (e.g., normal phase, ion exchange, reverse phase silica columns comprising various size of hydrophobic alkyl chains (—$(CH_2)_n$—$CH_3$ with n equal to 4, 8, 18, but not limited to) that interact with peptides and small molecules) but more specifically directed to the corresponding template and template analogs of the MIP produced. In some embodiment, a plurality of different types of MIPs each dedicated to a specific mycotoxin or group of mycotoxins can be used for the packing of the column.

In some embodiments, the present invention provides materials for separating, and quantifying mycotoxins. The present invention can then be utilized for traceability measurement of the feed/food material, or liquid source for the purpose of measuring the mycotoxins present in sample and its comparison to a commonly accepted referenced compound (e.g., mycotoxin standard material eluted using HPLC hyphenated to UV-, fluorescent detector or mass spectrometry detectors, etc.)

In some embodiments, traceability of the mycotoxin level can be accomplished using single type of MIP or a plurality of different types of MIPs, each tailored to a specific mycotoxin or group of mycotoxins, and applied to the detection in sample materials comprising of a feed or food sample (e.g., samples of grains (e.g., maize, wheat, etc.), fruits (e.g., apple, pears, grapes, etc.), coffee, tea, cocoa, etc.).

In some embodiments, traceability of the mycotoxin level using single MIP or a plurality of different types of MIPs each tailored to target a specific mycotoxin or group of mycotoxins, is applied to analytical investigation (e.g., HPLC) to determine if mycotoxins are present in the sample and if so, which mycotoxin(s) are present and at what levels. In some embodiments the analytical tools used for detecting mycotoxins (e.g., HPLC) can be used to predict danger of mycotoxin contamination in feed. In other embodiments the analytical tools used for detecting mycotoxins can be used to determine which MIP's or combination of MIP's are needed for application to the material from which a sample was taken in order to reduce or eliminate the mycotoxin(s) present.

In some embodiments, traceability of the mycotoxin level using single MIP or a plurality of different types of MIPs each dedicated to a specific mycotoxin or group of mycotoxin, is applied to the detection of the mycotoxin content of liquids used in animal production systems or used as beverages for animal and human consumption (e.g., water, milk, juices, wine, beer, etc.).

In some embodiments, traceability in terms of mycotoxin content can be applied to feed/food processing (meat processing, fresh produce processing) to test for the presence of mycotoxins during the entire production flow to determine where an issue of contamination arises, and a recall is required. Barcodes and other tracking media, all movement of product and steps within the production process should be referenced accordingly to allow the traceability of the sample analyzed.

In some embodiments, traceability of the mycotoxin level using single MIP or a plurality of different types of MIPs each dedicated to a specific mycotoxin or group of mycotoxins, is applied to the detection of the mycotoxin content of blood. For example, the present invention can be used in transfusion practice, to facilitate the continuous audit trail accounting for the whereabouts of a blood product and its current status in terms of processing, testing, storage, etc. at all points from initial collection from a donor right through to either transfusion to a recipient or disposal through the traceability of the mycotoxin level.

In some embodiments, the present invention utilizes MIPs described herein in combination with one or more methods and/or materials described herein for use in compositions and/or methods for the reduction, removal and/or elimination of mycotoxins (e.g., physical, mixing, chemical, microbiological methods described herein (e.g., to adsorb and/or sequester toxins)). For example, in some embodiments, a MIP described herein is utilized with one or more physical, mixing, chemical, or microbiological methods to sequester mycotoxins. A variety of physical means can be used to reduce mycotoxins presence such as mechanical separation (See, e.g., Dickens J. W., and Whitaker T. B., 1975. Peanut Science, 2: 45-50), density segregation (See, e.g., Huff W. E., and Hagler W. M., 1982. Cereal Chemistry, 59: 152-153), grain cleaning by washing with water or sodium carbonate to reduce contamination of maize (e.g., with Fusarium toxins), sorting out contaminated grains (e.g., via physical separation or fluorescence to detect the presence of mycotoxins), thermal inactivation (See, e.g., Lee L. S., 1989. Journal of American Oil Chemistry Society, 66: 1398-1413), UV irradiation, X-rays or microwave irradiation (See, e.g., CAST, 2003. *Mycotoxins: Risk inplant, animal, and human systems*. In: Task Force Report 139 (Niyo K. ed.), Council for Agricultural Science and Technology, Ames, Iowa, USA: pp. 1-199), and solvent extraction of toxins (See, e.g., Scott P. M., 1998. Review of Veterinary Medicine, 149: 543-548). A variety of chemical agents such as acids, bases (e.g., ammonia, caustic soda), oxidants (e.g., hydrogen peroxide, ozone), reducing agents (e.g., bisulphites), chlorinating agents and formaldehyde, have been used to degrade mycotoxins in contaminated feeds, particularly aflatoxins (See, e.g., Hagler W. M, Jr., 1991. In Mycotoxins, Cancer and Health. (Bray G. and Ryan D. eds.) Lousiana State University Press, Baton Rouge, L N, USA; Phillips T. D., Clement B. A., and Park D. L., 1994. *Approaches to reduction of aflatoxin in foods and feeds*. In: The toxicology of aflatoxins: Human health, veterinary agriculture significance (Eaton L. D. and Groopman J. D. eds.), Academic Press, New York, N.Y., USA: pp. 383-406;). Filters (e.g., filtration columns) and similar devices can likewise be utilized to remove mycotoxins.

The invention also provides systems and methods of providing various aspects of a product (e.g., products and/or components thereof of the invention and/or service utilizing the invention). The invention also provides systems and methods of providing company products to a party outside of the company, for example, a system and method for providing a customer or a product distributor a product of the company such as one or more MIPs (e.g., specific mycotoxin-targeted MIPs). For example, in some embodiments the present invention provides a product management system which can be separate from or combined with a traceability system. For example, samples of materials can be analyzed to determine if mycotoxins are present or absent in the material; if mycotoxins are present, the specific mycotoxins can be identified. This information can be used for traceability (e.g., to demonstrate the absence of all or certain mycotoxins). This information can also be used to provide a system for MIP product management whereby specific combinations of MIP's can be created and combined together to specifically target the mycotoxins present in the sample material.

In some embodiments, the company receives input (e.g., in the form of an order, information, or materials (e.g., biological sample (e.g., liquid sample suspected of comprising target compounds)) from a party outside of the company (e.g., a distributor and/or customer) to an order department; and provides output (e.g., in the form of a product delivered from shipping department (e.g., to a distributor and/or customer) or in the form of data report (e.g., traceability as laboratory analysis service)). In some embodiments, the product management system is organized to optimize receipt of orders and delivery (e.g., in a cost efficient manner) of products (e.g., compositions comprising one or more MIPs (e.g., mycotoxins-specific MIPS)) to a party outside of the company; and to obtain payment for such product from the party. In some embodiments, the product management system is organized to bar-code the samples or materials submitted for analysis and delivery (e.g., in a cost efficient manner) of datasheet reports (e.g., levels of several mycotoxin that were analyzed through the use of MIP-SPE or HPLC-columns made of MIPs (e.g., mycotoxins-specific MIPS)) to a party outside of the company; and to obtain payment for such service from the party.

In some embodiments, the company comprises manufacturing and administration. Compositions of the present invention can be produced in manufacturing and/or by a third party, and can be stored separately therein such as in materials storage and/or other component storage (e.g., product storage) and/or can be further assembled (e.g., combined (e.g., one or more MIPs can be combined with one or more other types of MIPs and/or with other components (e.g., carriers and/or other bioactive components described herein))) and stored (e.g., in device and/or product storage). In some embodiments, administration includes order department (e.g., that receives input in the form of an order for a product from customer and/or distributor). Order department can then provide output in the form of instructions to shipping department to fill the order (i.e., to forward products as requested to customer or distributor). In some embodiments, the shipping department, in addition to filling an order for the product or for the service, can also provide information/data to billing department. In some embodiments, other component of company may include customer service department (e.g., that can receive input from customer and/or provide output in the form of feedback or information to customer and/or can receive input or provide output to any other component of company). For example customer service department may also receive input from customer in the form of requested technical information, for example, for confirming that products and methods of the invention can be applied to the particular need of customer, and can provide output to customer in the form of a response to the requested technical information.

Thus, in some embodiments, components of company are suitably configured to communicate with each other to facilitate the transfer of materials and parts, devices, other components, products, datasheets and information within and outside of company. For example, a physical path can be utilized to transfer products from product storage to shipping department upon receiving suitable input from order department or from sample storage to analytical department upon the reception of rush analysis request. Order department, in comparison, can be linked electronically with other components within company, for example, by a communication network (e.g., a network (e.g., internet and/or intranet)), and can be further configured to receive input, for example, from customer by a telephone network, by mail or other carrier service, or via the internet.

In some embodiments, a product management system further comprises one or more data collection systems.

In some embodiments, company can utilize a number of software applications to provide components of company with information and/or to provide a party outside of company access to one or more components of company (e.g., access to order department and/or customer service department and/or data collection/storage). Such software applications may comprise a communication network such as the Internet, a local area network, or an intranet. For example, in an internet-based application, customer can access a suitable website and/or a web server that cooperates with order department such that customer can provide input in the form of an order to order department. In response, order department can communicate with customer to confirm that the order has been received, and can further communicate with shipping department, providing input that products of the invention (e.g., compositions comprising one or more different types of MIPs (e.g., mycotoxins-specific MIPs)) should be shipped to customer or to the analytical department, providing input that the analyses using the products of the invention (e.g., compositions comprising one or more different types of MIPs (e.g., mycotoxins-specific MIPs) packed as separative devices) should be performed. Thus, in this manner, the business of company can proceed in an efficient manner.

Thus, in some embodiments, in a networked arrangement, various subcomponents of a company (e.g., storage, analytical, billing department and shipping department) can communicate with one another by way of respective computer systems. In some embodiments, the present invention provides methods for providing various aspects of a product (e.g., products and/or components thereof of the invention), as well as information regarding various aspects of a product of the present invention (e.g., performance data, usage statistics, etc.), to parties (e.g., customers/users, distributors, third parties (e.g., government agencies (e.g., National Institutes of Health and/or the Centers for Disease Control), etc). In some embodiments, a product is removed from product storage, for example, by shipping department, and sent to a requesting party such as customer or distributor. Typically, such shipping occurs in response to the party placing an order, which is then processed (e.g., forwarded to appropriate party) within the organization and results in the ordered product being sent to the party or service being provided to the party. Data regarding shipment of the product or the datasheets of analytical service to the party can be transmitted further within the organization, for example, from shipping or analytical department to billing department, which, in turn, can transmit a bill to the party, either with the product or datasheet, or at a time after the product or datasheet has been sent The present invention also provides methods of providing technical service to parties using a product and/or components thereof of the invention. While such a function may be performed by individuals involved in product research and development, inquiries related to technical service can generally be handled, routed, and/or directed by an administrative department of the organization (e.g., customer service department). Technical service (e.g., solving problems related to use of the product or individual components of the product) communications may require exchange of information between a user (e.g., customer) and customer service department.

As mentioned above, any number of variations of a process of providing products (e.g., a products and/or components thereof described herein) and/or service s to a user are possible and within the scope of the invention. Accordingly, the invention includes methods (e.g., business methods) that involve (1) the production of products (e.g., a product and/or components thereof described herein); (2) receiving orders for these products; (3) sending the products to parties placing such orders; (4) sending bills to parties obliged to pay for products sent to such; and/or (5) receiving payment for products sent to parties. For example, methods are provided that comprise two or more of the following steps: (a) obtaining parts, materials, and/or components from a supplier; (b) preparing one or more first products (e.g., one or more components described herein (e.g., a MIP template described herein, and/or one or more different types of MIPs generated utilizing the MIP template)); (c) storing the one or more first products of step (b); (d) combining the one or more first products of step (b) with one or more other components to form one or more second products (e.g., a composition comprising two or more different types of MIPs); (e) storing the one or more first products of step (b) or one or more second products of step (d); (f) obtaining an order for first product of step (b) or a second product of step (d); (g) shipping either the first product of step (b) or the second product of step (d) to the party that placed the order of step (f); (h) tracking data regarding the amount of money owed by the party to which the product is shipped in step (g); (i) sending a bill to the party to which the product is shipped in step (g); (j) obtaining payment for the product shipped in step (g) (generally, but not necessarily, the payment is made by the party to which the product was shipped in step (g)); and (k) exchanging technical information between the organization and a party in possession of a product shipped in step (d) (typically, the party to which the product was shipped in step (g)).

A purchaser may wish to purchase one or a plurality of different types of MIPs. In some embodiments, a composition comprising a plurality of different types of MIPs is customized for the purchaser (e.g., based on information regarding the presence of one or more types of target compounds to be eliminated/sequestered). An advantage of this is that a customer may be able to customize a particular product to their needs (e.g., purchase a composition comprising a plurality of different types of MIPs specific for each target compound, rather than separately purchasing compositions comprising only a single MIP, and then utilizing each composition in combination with others).

The invention further provides methods associated with the design of custom products. These methods include, for example, (1) taking an order from a customer for product with specific subcomponents and/or methodology for operating the same, (2) preparation of the product with specific subcomponents and/or methodology for operating the same, (3) and providing (e.g., shipping) the product of (b) to the customer.

EXPERIMENTAL

The following examples are provided in order to demonstrate and further illustrate certain preferred embodiments and aspects of the present invention and are not to be construed as limiting the scope thereof.

Example 1

Ochratoxin A Template Synthesis

Preparation of 2-acetoxy-3,5-dichlorobenzoic acid. A 1 L, round-bottom, three neck flask equipped with: a mechanical stirrer, a thermometer and a 125 mL dropping funnel with pressure equilibration was placed in a water bath maintained at 65° C. The following reagents were subsequently charged to the flask with an efficient stirring: 250 mL of dry toluene, 2.5 mL of concentrated sulfuric acid and 207 g of well ground, solid 3,5-dichlorosalicylic acid, which forms a mobile suspension. When the temperature of this constantly stirred mixture reached 60° C. (with the water bath temperature maintained at 65° C.) a drop-wise addition of 108 g (100 mL) of acetic anhydride was initiated and completed within 30 min. During the acetic anhydride addition the temperature of the reaction mixture was not allowed to exceed 75° C. After completing the addition, the mixture was stirred and heated to 70° C. for another 4 h. After this time, the agitation was stopped and the mixture cooled over night to room temperature. The white crystals that separated from the mixture were filtered off, washed with 2×10 mL of ice-cold toluene and vacuum dried at 50° C. to yield 206 g (82.7% yield) of 2-acetoxy-3,5-dichlorobenzoic acid. An additional 30.6 g (12.3%% yield) of the product was recovered by: concentrating the filtrate to ½ of the original volume, cooling the solution in an ice-water bath, filtering off the crystalline product and vacuum drying it at 50° C.

In situ preparation of 2-acetoxy-3,5-dichlorobenzoic acid chloride and its use in preparation of N-(2-acetoxy-3,5-dichlorobenzoyl)-L-phenylalanine ethyl ester (Because of personnel safety the process was carried out under a fume hood).

The production system was made of a 3 L reactor equipped with an efficient mechanical stirrer (Ace Glass Inc, Louisville, Ky., cat#13650-12/23) a 250 mL dropping funnel, a reflux condenser with $CaCl_2$ drying tube with the outlet attached to the acidic vapors absorber, a dry nitrogen gas inlet and a thermometer placed in a water bath of 22° C. One liter of dry toluene, 5 mL of dimethylformamide and 103 g of 2-acetoxy-3,5-dichlorobenzoic acid were charged into the reactor under agitation. A drop by drop addition into the reaction mixture of 217 mL (1.05 equiv.) of 2 M oxalyl chloride solution in methylene dichloride was done under stirring over 2.5 h. A stream of a toxic gasses mixture: HCl, CO and $CO_2$, which was produced in the reaction was absorbed in 1 L of 10% sodium hydroxide solution placed in a trap cooled with tap water. After completing the addition of oxalyl chloride accompanied by complete dissolution of solids, a strong stream of dry nitrogen was passed through the solution for 1 h to remove most of acidic gasses (HCl, $CO_2$) that stayed dissolved in the reaction mixture. After this time the content of the flask was cooled below 15° C. in an ice-water bath, and 95 g (1.0 equiv.) of solid L-phenylalanine ethyl ester hydrochloride was added into the mixture. A new 500 mL dropping funnel was installed in place of the 250 mL funnel and filled with a solution of 145 mL of triethylamine (2.55 equiv.) in 350 mL of toluene. The triethylamine solution was then added over a 2 hr time period into the ice-water bath cooled and stirred reaction mixture. During the time of addition, the temperature of the mixture was maintained below 25° C. This temperature was maintained for 4 h after the completion of the triethylamine addition and then the triethylamine hydrochloride was filtered off and the white cake washed with two 100 mL portions of toluene. The filtrate was then transferred into a 3 L separatory funnel and washed with two 500 mL portions of water and one 500 mL portion of brine. The toluene layer was then concentrated to a volume of 500 mL and left over night in a refrigerator for crystallization. The white crystals were collected on the filter and washed with one 100 mL of ice-cold toluene, yielding 108.7 g (62%% yield) of ethyl ester of N-(2-acetoxy-3,5-dichlorobenzoyl)-L-phenylalanine.

$^1$H NMR (deutereted chloroform (abbreviated as $CDCl_3$), ppm): 7.78 δ, J 2.8, 1H, 7.55 δ, J 2.4, 1H, 7.30-7.27 m, 3H, 7.11 broad δ, J 8.0, 1H, 7.08 δq, J 8.0 and 1.6, 1H, 4.99 q, J 6.0, 1H, 4.24 q, J 7.0, 2H, 3.29 dd, J 5.6 and 14.4, 1H, 3.21 dd, J 9.2 and 14.0, 1H, 2.11 s, 3H, 1.31 t, J 7.2, 3H.

Preparation of N-(3,5-dichloro-2-hydroxybenzoyl)-L-phenylalanine (OTA template). One hundred and eight grams of ethyl ester of N-(2-acetoxy-3,5-dichlorobenzoyl)-L-phenylalanine were dissolved in 1 L of anhydrous ethyl alcohol and placed in a 2 L round bottomed flask equipped with a magnetic stirring bar and placed in water bath at ambient temperature. Into this mixture a solution of 33.33 g of sodium hydroxide in 37.2 mL of water was added in a single portion and the mixture stirred at ambient temperature for 17 h (overnight). A volume of 68.6 mL of concentrated hydrochloric acid was added under stirring, which was maintained for an additional of 2 h. The precipitated sodium chloride was filtered off and the filtrate evaporated to dryness at 60° C. under 30 T of pressure. The residue of 88.9 g (98% yield) solidified after cooling in form of a colorless glassy product, which was well soluble in toluene or acetonitrile, thereby producing an OTA template (e.g., for use in MIP-OTA production). MS: $M^+$ 354 and 356 $^1$H NMR (CDCl$_3$, ppm): 12.2 very broad s, 1H, 7.49 d, J 2.4, 1H, 7.35-7.28 m, 3H, 7.20 d, J 2.0, 1H, 7.18-7.16 m, 2H, 6.80 br d, J 6.4, 1H, 6.4 very broad s, 1H, 5.07 dd, 5.2 and 5.2, 1H, 3.34 dd, J 14.0 and 5.2, 1H, 3.27 dd, J 13.6 and 5.2, 1H.

Example 2

MIP-OTA Synthesis in Toluene-Cyclohexane Mixture

Five hundred milliliters of toluene, 35.42 g (0.1M) of OTA template, 16.18 mL (0.15 M) of 2-vinylpyridine, 12.13 mL (0.1 M) of 2-hydroxyethylmethacrylate, 235.75 mL (1.25 M) of ethylene glycol dimethacrylate and 2.46 g (15 mM) of AIBN were placed in a 3 L four necks flask equipped with a: mechanical stirrer, reflux condenser, thermometer and nitrogen inlet/outlet. The resulting clear solution was stirred for 1 h at room temperature and a constant stream of nitrogen passed through the vessel (e.g., to remove oxygen that can inhibit polymerization). The flask was then heated to 60° C. and the mixture vigorously stirred. Polymerization occurred as long as the temperature of the solution increased to ~55° C. (e.g., observed by an increase in the viscosity of the solution). Fifteen minutes after polymerization began, 600 mL of (1:1) cyclohexane/toluene mixture was added in a single portion to promote polymer sphere separation from the solution. Vigorous agitation of the mixture was maintained and an additional 500 mL of toluene added 30 min later to improve the overall mixing of the still growing volume of solid MIP suspension in a relatively low volume of solvent. A temperature of 60° C. and agitation was maintained for an additional 5 h after which the agitation was turned off to let MIP spheres sediment. The supernatant was decanted and the pellet transferred into a 2 L rotary evaporator flask to remove the remnant solvents from the MIP spheres, at 40° C. and under a reduced pressure of 30 T. The dried spheres were grinded to approximately 140 mesh and washed 5 times, by stirring with 1.5 L of 0.2 w/v % sodium hydroxide solution for 30 min and decantation. The final portion of the MIP-OTA spheres was mixed with 1.5 L of 0.5 v/v % acetic acid, which was also decanted and 1.5 L of DI water. The resultant template-free wet MIP-OTA spheres (~1.0 L volume) were dried in a laboratory oven at 80° C. for 4 h, using four glass trays. The white powder-like MIP-OTA weighed 248 g (93% yield). Various samples identified in Table 1 below were synthesized utilizing this method.

For this and subsequent synthesis procedures, polymerization inhibitors were removed from monomers and cross-linker by vacuum distillation, before being used in polymerization, and the solvents used in polymerization were of ACS purity. The concentration of the template in subsequent washes was obtained by comparing the intensity of the red-orange color of the $Fe^{3+}$ complex of the template at $\lambda_{max}$ 385 nm with the calibration curve constructed for template concentrations between 10 μg/mL and 1 mg/mL.

TABLE 1

Identification of the samples synthesized in toluene-cyclohexane mixture

| Sample ID | Toluene-cyclohexane (mL) | Final washing | Morphology |
| --- | --- | --- | --- |
| 523-29/30 | 45/15 | Ethanol | Spheres, white powder |
| 523-31 | 65/15 | Ethanol | Spheres, white powder |
| 523-34 | 65/35 | Ethanol/NaOH | Spheres, white powder |
| 523-35 | 55/22 | Ethanol/NEt$_3$/H$_2$O | White powder, clusters |
| 523-36 | 90/30 | NaOH/H$_2$O | White clusters |

Example 3

OTA MIP Synthesis in Acetonitrile

Five hundred milliliters of acetonitrile, 17.71 g (50 mM) of OTA template, 8.1 mL (75 mM) of 2-vinylpyridine, 6.1 mL (50 mM) of 2-hydroxyethylmethacrylate, 117.9 mL (625 mM) of ethylene glycol dimethacrylate and 1.23 g (15 mM) of AIBN were placed in a 3 L four necks flask equipped with a: mechanical stirrer, a 500 mL dropping funnel with pressure equilibration, a thermometer and nitrogen inlet/outlet and heated with an electric heating mantel. The resulting clear solution was stirred for 1 h at room temperature and a constant stream of nitrogen passed through the vessel (e.g., to remove oxygen that can inhibit polymerization). Afterwards, the flask was heated to 60° C. and the mixture vigorously stirred. Polymerization ensued as long as the temperature of the solution increased to ~55° C. (e.g., observed by increased viscosity of the solution). Thirty minutes after polymerization started (e.g., when gel-formation is observable), 1.5 L of acetonitrile (pre-heated to 55° C. and washed with nitrogen to remove oxygen) was added rapidly, in three portions from a 500 mL dropping funnel to avoid block polymer formation and to promote the polymer spheres separation from the solution. Vigorous agitation and heating of the mixture was maintained for the next 17 h (overnight). Afterwards, heating and agitation was turned off and the MIP spheres allowed to sediment. The supernatant was decanted and the pellet transferred into a 2 L rotary evaporator flask and the rest of the solvent removed from the MIP spheres at 40° C. and under reduced pressure of 30 T. The dried spheres were grinded to approximately 140 mesh and washed 5 times, by stirring with 1.5 L of 0.2 w/v % sodium hydroxide solution for 30 min and decantation. The final portion of the MIP-OTA spheres was mixed with 1.5 L of 0.5 v/v % acetic acid, which was also decanted and 1.5 L of DI water. The resultant template-free wet MIP-OTA spheres (~1.2 L volume) were dried in a laboratory oven at 80° C. for 6 h, using 4 glass trays. The white powder-like MIP-OTA weighed 115 g (86.2% yield). Various samples identified in Table 2 below were synthesized utilizing this method.

TABLE 2

Identification of the samples synthesized in acetonitrile

| Sample ID | Acetonitrile (mL) | Final washing* | Morphology |
| --- | --- | --- | --- |
| 523-48 | 100 (+ toluene 50 mL) | NaOH | Spheres/clusters, yellow |
| 523-49 | 50 (+ water 150 mL) | NaOH | Spheres, yellow/orange |
| 523-59 | 225 mL | NaOH | Spheres, white |
| 523-60 | 190 mL | NaOH | Spheres, white |

*after 4x 0.2% NaOH washing, 1x 1% AcOH wash followed with 1x H$_2$O wash.

Example 4

Large Scale MIP-OTA Preparation in Toluene

The preparation was carried in a 3 L reactor with a four necks lid, equipped with a mechanical stirrer with two propellers installed at the bottom and at halfway up, an electric heating mantel, a thermometer, a 1.5 L dropping funnel with air equilibration and nitrogen gas inlet, and a reflux condenser equipped with a bubble-meter to control nitrogen flow. The following reagents were charged into the reactor: 54.54 g (154 mM) of N-(3,5-dichloro-2-hydroxybenzoyl)-L-phenylalanine (OTA template), 25 mL (231 mM) of 2-vinylpyridine, 18.7 mL (154.0 mM) of ethylene glycol monomethacrylate, 363 g (1.925 M) of ethylene glycol dimethacrylate, 770 mL of toluene and 5.0 g (30.8 mM) of AIBN. An additional 1.5 L of toluene was placed in a dropping funnel. The reaction mixture was vigorously stirred and the dissolved gas removed by passing a strong stream of nitrogen at ambient temperature for 45 min and at first through the toluene that had been placed in the dropping funnel, and later through the void volume of the reactor. A weak nitrogen flow was maintained during the time of polymerization. Polymerization was initiated by heating the reaction mixture up to 55° C. After 15 min, the viscosity of the mixture increased and stirring became less efficient. At this point, an additional volume of toluene (of ambient temperature) was added from the dropping funnel. The addition was set to run fast enough to prevent the overheating of the mixture due to the exothermal properties of the reaction and to keep the viscosity of the reaction mixture low enough to allow efficient agitation during the time of formation and separation of the polymer spheres. The temperature of 60-70° C. and stirring were maintained for the next 5 h and then the mixture was left without stirring at ambient temperature until the next day. Then, 1.75 L of the toluene layer was decanted from the MIP particles and toluene wet MIP particles grounded and transferred to a 2.0 L rotary-evaporator flask. Most of the toluene (~0.45 L) that was trapped inside the MIP particles was distilled off from the MIP spheres under slightly reduced pressure and at a temperature below 70° C. At the end of toluene removal the powder-like product that had been formed displayed a tendency to produce dust. At this point, the evaporation was stopped and MIP particles were washed with 2 portions of ethanol of 500 mL each. Around 0.75 L of ethanol was then decanted from the solids and evaporated to yield 30 g (55%) of regenerated OTA template and 700 mL of regenerated ethanol. The white fine solids were then washed with 4 times 0.5 L portions of 0.2 w/v % NaOH followed by a single wash with 500 mL of 1 v/v % acetic acid and a single 500 mL portion of DI Water. The resultant 'wet' OTA-MIP was then dried for 24 h in a laboratory oven at 80° C. A mass of 411.4 g (96.6% yield) of white powder-like product was obtained and fractionated using standard sieves. This methodology was utilized to synthesize the various samples identified in Table 3. Details of the size repartition are provided in Table 4.

TABLE 3

Identification of the samples synthesized in toluene or polyvinyl alcohol (abbreviated as PVA)

| Sample ID | Toluene or PVA(mL) | Final washing | Morphology |
|---|---|---|---|
| 514-37/39 | 150 mL Toluene | NaOH* | Spheres/clusters, white |
| 523-40 | 5 mL PVA + 100 mL water | NaOH* | Spheres/clusters, white |
| 514-41 | 5 mL PVA + 50 mL water | NaOH* | Spheres/clusters, green |
| 514-42/44 | 388 + 776 mL toluene | NaOH* | Spheres/clusters, white |

*4x wash with 0.2% NaOH was followed with 1x wash with 1% AcOH and 1x water.

TABLE 4

Size repartition of the MIP-OTA produced.

| Fraction size | Fraction weight (g) | w % of MIP-OTA |
|---|---|---|
| >106 μm | 212.81 | 51.8 |
| 45 μm-106 μm | 127.72 | 31.1 |
| 20 μm-45 μm | 56.97 | 13.9 |
| <20 μm | 13.28 | 3.2 |

Example 5

Low Temperature and UV Initiated MIP-OTA and NIP Polymerization/Synthesis

Photochemical reaction set. Quartz, photochemical UV immersion well (Ace Glass, Catalogue # 7856-10) equipped in 450 Watt UV Lamp (ACE Glass, Catalogue #7825-34) and 450 Watt Cased Power Supply (ACE Glass, Catalogue #7830-58) is attached to a circulation chiller WKL 230 LAUDA (supplied by Brinkmann Instuments, Inc.), and cooling water of 4° C. is run through the well mantle at the time when the UV lamp is on.

Polymerization (Table 5) The monomers, template, initiator (IABN) and a crosslinker are placed in a translucent, polyethylene bottle (Nalgene®style 2105) and a stream of Argon is passed through the mixture for 15 min to remove all of the oxygen, which is known to inhibit free radical polymerization. Than the bottle is closed and attached to the immersion well, at the level of the UV lamp center, and immersed, together with the photochemical reaction set, into an ice-water bath. Cooling water is run through the lamp mantle, when the light is turned on, and the reaction mixture irradiation is maintained for four hours (UV safety glasses are required at the time when the UV lamp is on). Additional ice is supplied to, and excess of water is drained from the bath during the course of the UV polymerization, to maintain cooling bath temperature at 4° C. After completing polymerization the bottle is open, the polymer is crushed and grinded into small pieces which are washed: once with ethanol, ten times with 0.2% sodium hydroxide, one time with 1% acetic acid and three times with ethanol, to remove the template from the polymer and secure maximum activity of MIP which is finally dried in a laboratory oven to remove ethanol residues. The yields of MIP-OTA were of 56.7% and 49% respectively for #555-54A and 555-54B.

TABLE 5

Identification of the MIP-OTA samples synthesized using low temperature and UV initiation

| MIP-OTA | Styrene (mM) | 2-Vinyl-Pyridine (mM) | Ethyleneglycol Monomethacrylate (mM) | Ethyleneglycol Dimethacrylate (mM) | IABN (mM) | OTA Template (mM) |
|---|---|---|---|---|---|---|
| 555-54A | 10.73 | — | 7.16 | 89.5 | 1.07 | 7.16 |
| 555-54B | — | 10.73 | 7.16 | 89.5 | 1.07 | 7.16 |

Example 6

MIPs' Sequestration Capabilities Toward Mycotoxins—Applied to OTA

MIP polymers produced either in toluene-cyclohexane, acetonitrile or toluene were tested toward OTA (Sigma-Aldrich, St. Louis, Mo., USA) mycotoxin for the removal of the OTA mycotoxin from liquid or semi-liquid media via chemical interactions. The MIP produced was used herein to depict the differences in affinity of sequestration of the OTA mycotoxin and to evaluate the specificity of the material. An amount of 12.5 mg of MIP was placed into an Amicon ultracentrifuge filter device (5,000 Da). The preparation was made together with a blank sample containing no MIP material and a positive control containing only the OTA toxin to be tested. The sequestration test was performed in citrate buffer 50 mM adjusted to pH 4.0. All samples were incubated during 90 min on an orbital rotary shaker (Brunswick, Champaign, Ill., USA) at 150 rpm maintained at a temperature of 37° C. Three final concentrations of OTA were tested with the system, 50, 100, 250 parts per billion (ppb) in a final volume of 12.5 mL. After incubation the microcentrifuge tubes were centrifuged at 10,000 rpm for 10 min. The supernatant was collected into amber and silanized HPLC vials, preventing any interaction of the mycotoxin with the vial, and calculated from HPLC (Alliance, Waters Corp., Milford, Mass., USA) coupled to fluorometric and diode-array detectors signal (e.g., to detect amounts of mycotoxin and mycotoxin sequestered) according to standard methods (See, e.g., Entwisle A. C., Williams A. C., Mann P. J., Slack P. T., Gilbert J., 1995. *Liquid chromatography method with immunoaffinity column cleanup for determination of ochratoxin A in barley: Collaborative study*. Journal of AOAC, 83: 1377-1383).

Results (See Table 5) indicated that both MIP prepared with the OTA-template and without the template (NIP) at a concentration of 1.00 g/L had very high affinity for the OTA mycotoxin molecule at pH 4.0. According to the preparation method, the MIP generated after precipitation polymerization (identified as # 523-31 synthesized in toluene; # 523-34, -35, -36 synthesized in toluene-cyclohexane mixture; and # 523-48 synthesized in toluene-acetonitrile mixture) had an sequestration efficacy above 98.8% whereas the MIP generated after emulsion polymerization (identified as # 523-40 and -41 synthesized in water and polyvinyl alcohol; and 49 synthesized in acetonitrile) has a lower affinity below 63%. The NIP molecule is also able to interact with 98.8% sequestration efficacy. At this stage, the precipitation polymerization group exhibited no statistical differences between the NIPs and the MIPs whereas the emulsion polymerization group exhibited significant differences between MIP and NIP and also between MIPs.

Two successive washing steps under 15% ethanol/sodium hydroxide, acetic acid 1% solution were used to evaluate the ability of the two MIPs groups to preserve the interaction and to account for the strength of the sequestration (See Table 6). The emulsion polymerization group showed a robust release of the OTA from the MIP as well as a release of the remnant template co-eluting with the OTA mycotoxin accounting for the negative percentage adsorbed. Accordingly, the present invention provides that the emulsion polymerization methodology was not suitable at creating efficient adsorbent to OTA molecules. The present invention also provides that the precipitation polymerization group had a significantly high affinity toward OTA allowing a maximum desorption of only 26.3% of the OTA molecule for the MIP synthesized in a mixture of toluene-acetonitrile without any interference with any remnant template.

TABLE 6

Sequestration activity of the MIPs and NIPs synthesized in toluene, acetonitrile and toluene-cyclohexane mixture for ochratoxin A and stability of the interaction after two successive washes with 15% ethanol/sodium hydroxide.

| | Average still adsorbed (%) | | | Average desorbed (%) | | |
|---|---|---|---|---|---|---|
| Sample ID | Initial | 1st wash | 2nd wash | Initial | 1st wash | 2nd wash |
| NIP 523-31# | 98.84 | 92.52 | 86.66 | 1.162 | 7.478 | 13.342 |
| MIP 523-34# | 98.95 | 93.05 | 89.50 | 1.048 | 6.955 | 10.500 |
| MIP 523-35# | 99.04 | 90.60 | 86.09 | 0.963 | 9.397 | 13.915 |
| MIP 523-36# | 99.00 | 86.76 | 82.83 | 1.000 | 13.238 | 17.175 |
| MIP 523-48# | 99.73 | 85.76 | 73.71 | 0.273 | 14.242 | 26.293 | precipitation polymerization

Example 7

Titration of the Amount of MIP for the Sequestration of Ochratoxin a

A titration experiment was conducted to investigate inclusion rates of MIP, from 0.01 g/L to 1.00 g/L (or 0.001 to 0.1% of inclusion rate). The preparation was made together with a blank sample containing no MIP material and a positive control containing only the OTA toxin to be tested. The sequestration test was performed in citrate buffer 50 mM adjusted to pH 4.0. All samples were incubated during 90 min on an orbital rotary shaker (Brunswick, Champaign, Ill., USA) at 150 rpm maintained at a temperature of 37° C. Three final concentrations of OTA were tested with the system, 50, 100, 250 ppb in a final volume of 12.5 mL. After incubation the microcentrifuge tubes were centrifuged at 10,000 rpm for 10 min. The supernatant was collected into amber and silanized HPLC vials, preventing any interaction of the mycotoxin with the vial, and calculated from HPLC (Alliance, Waters Corp., Milford, Mass., USA) coupled to fluorometric and diode-array detectors signal (e.g., to detect amounts of mycotoxin and mycotoxin sequestered) according to standard methods (See, e.g., Entwisle et al., 2000 as cited previously).

Figure 3:
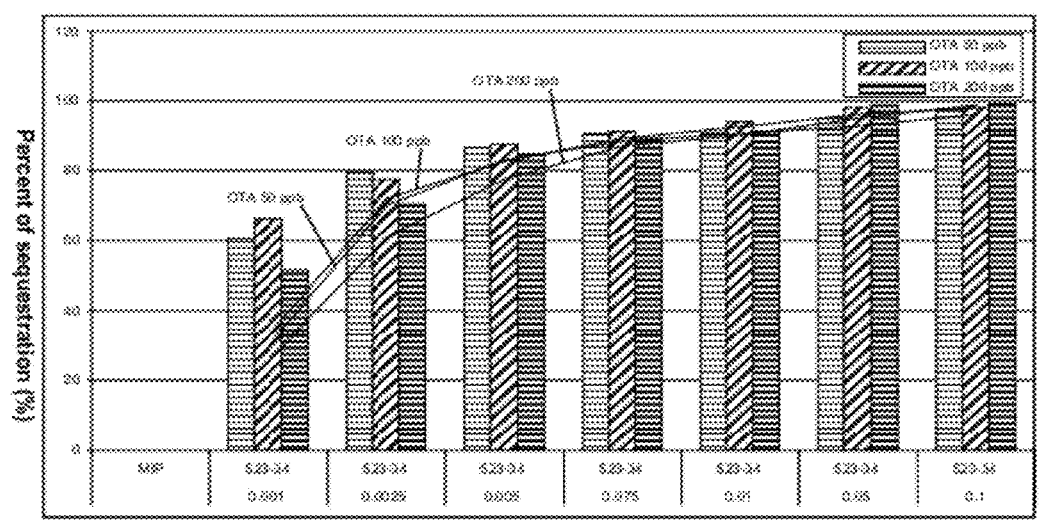
FIG. 3 shows MIP-OTA sequestration efficacy for OTA at several rates of inclusion.

As shown in FIG. 3, at 0.05 g/L the optimum efficacy was above 80% of sequestration value and reached an average of 86.4±1.5% of sequestration. The incidence of the level of inclusion of the MIP compounds was evaluated by examining the sequestration activity of 0.010, 0.025, 0.050, 0.075, 0.100, 0.50, and 1.00 g/L of the MIP #523-34 (synthesized in toluene-cyclohexane mixture) and #523-60 (synthesized in acetonitrile) on 50, 100, 200 ppb of OTA in acidic buffer condition (pH 4.0). The MIP size was set between 45 and 106 µm of particles diameter since this fraction gave the best sequestering result and represented the highest proportion of size particles in the total MIP product synthesized.

Each MIP, #523-34 and #523-60, was able to adsorb 91.53±10.86 and 81.75±23.67% of OTA, respectively as an average of the total sequestration independently from the level of inclusion. A deflection point was found in the sequestration curve for levels of MIP inclusion of 0.05 and 0.10 g/L respectively for #523-34 and #523-60 samples. The sequestration affinity averages for inclusion of 0.05 to 1.00 and 0.10 to 1.00 g/L for #523-34 were 96.31±2.23 and 97.39±0.70%, respectively. The sequestration affinity averages for inclusion levels between 0.05 and 1.00 g/L and between 0.10 and 1.00 g/L for #523-60 were 94.51±6.54 and 97.76±0.91%, respectively. The present invention thus provides that the synthesized MIP in a mixture of toluene-cyclohexane was favorable to a higher affinity rate for OTA sequestration at 0.01 g/L of inclusion with 72.42±2.58% of affinity rate whereas the sample produced with acetonitrile was less effective with an affinity rate of 47.40±6.08 and 84.77±1.96 respectively at 0.01 and 0.05 g/L of inclusion of product.

Example 8

Figure 4:
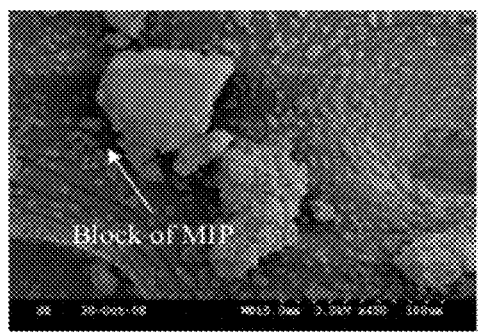
FIG. 4 shows MIP-OTA observed on a Hitachi S-4300 scanning electron microscope at ×15,000 of magnification and at 3.0 keV.
Figure 4:
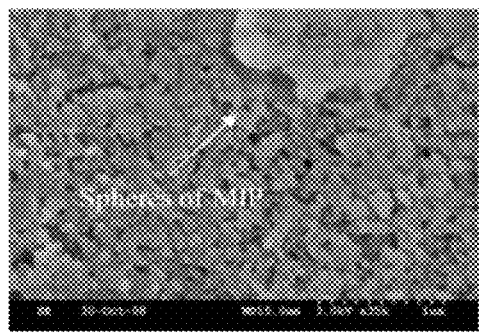

Affinity of Different MIP and NIP and Specificity Characterization Toward Ochratoxin a Experiments were performed during development of embodiments of the invention in order to evaluate the affinity of different NIPs/MIPs synthesized either in acetonitrile or toluene as solvent used for polymerization. The samples #523-31 (toluene) and #523-59 (acetonitrile) were synthesized without any template of OTA (defined as a Non Imprinted Polymer); the samples #523-34 (mixture of toluene-cyclohexane) and #523-60 (acetonitrile) were polymerized around the OTA analog template. The samples were then subjected to sieving using different cut-off size sieves. The sizes of particle range tested were as described in Example 4. The MIP production predominantly produced size particles between about 45 and 106 µm of diameter (as shown in FIG. 4). The preparation was made together with a blank sample containing no MIP material and a positive control containing only the OTA toxin to be tested. The sequestration test was performed in citrate buffer 50 mM adjusted to pH 4.0. All samples were incubated for 90 min on an orbital rotary shaker (Brunswick, Champaign, Ill., USA) at 150 rpm maintained at a temperature of 37° C. Three final concentrations of OTA were tested with the system, 50, 100, 250 ppb in a final volume of 12.5 mL. After incubation the microcentrifuge tubes were centrifuged at 10,000 rpm for 10 min. The supernatant was collected in amber and silanized HPLC vials, preventing any interaction of the mycotoxin with the vial, and calculated from HPLC (Alliance, Waters Corp., Milford, Mass., USA) coupled to fluorometric and diode-array detectors signal (e.g., to detect amounts of mycotoxin and mycotoxin sequestered).

Comparison of the OTA affinity showed only limited difference evaluated on a single sequestration run without successive washing steps on the 3 different concentrations of toxin (50, 100, 250 ppb). Only the sample #523-59 made of NIP without sieving exhibited lower sequestration capabilities at every pH concentration of OTA. Lower sequestration values were also found for the MIP sample #523-34 for 50 ppb concentration values of OTA especially for sizes between 20 and 45 and in a lesser extend 45 to 106 µm of diameter. Thus, in some embodiments, the present invention provides that the size of MIP particles produced according to methods of the present invention have little impact on the total adsorbent affinity for OTA, with an affinity fluctuating in the worst cases between 78 to 99% of sequestration rates. NIPs are less effective in their sequestering properties than MIPs accounting for the specificity of the MIPs to interact with the OTA mycotoxin.

Example 9

Trapping of Spiked OTA in Wine Using MIP and Direct Filtration of Spiked Ochratoxin a in Wine Using MIP Solid Phase Extraction (SPE)-like Filtering Device A standard extraction procedure on a sample of white wine (Chardonnay 2005—California) using an immunoaffinity column was tested. The extraction was made on a pure sample of wine as well as on spiked samples of wine with 5, 10, 20 ppb of pure crystalline OTA. The original concentration average of the wine was 1.676±0.269 ppb of OTA (e.g., as determined following a standard extraction procedure). Recovery of the 5 ppb spiked sample was 100% and around 77.7% for 10 ppb.

The preparation was made together with a blank sample containing no MIP material and a positive control containing only the OTA toxin to be tested. The sequestration test was performed in citrate buffer 50 mM adjusted to pH 4.0. All samples were incubated for 90 min on an orbital rotary shaker (Brunswick, Champaign, Ill., USA) at 150 rpm maintained at a temperature of 37° C. Three final concentrations of OTA were tested with the system, 50, 100, 250 ppb in a final volume of 12.5 mL. After incubation the microcentrifuge tubes were centrifuged at 10,000 rpm for 10 min. The supernatant was collected in amber and silanized HPLC vials, preventing any interaction of the mycotoxin with the vial, and calculated from HPLC (Alliance, Waters Corp., Milford, Mass., USA) coupled to fluorometric and diode-array detectors signal (e.g., to detect amounts of mycotoxin and mycotoxin sequestered).

Figure 5:
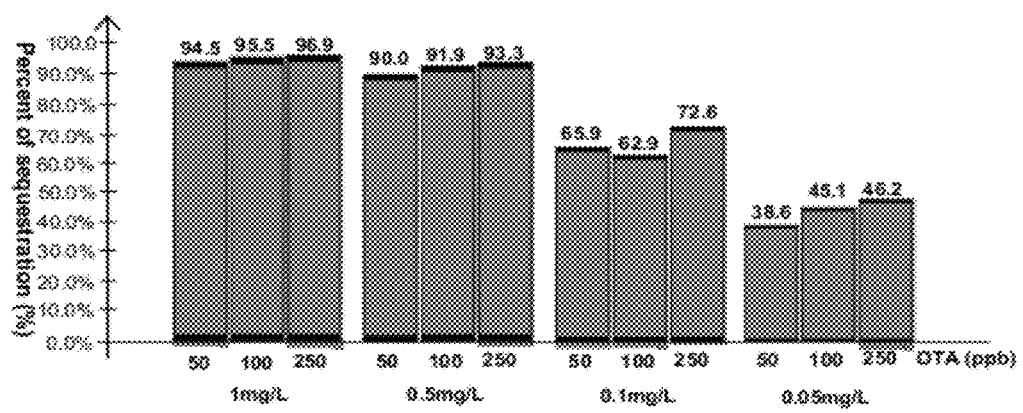
FIG. 5 shows the sequestration affinity of MIPs (synthesized in toluene-cyclohexane mixture) for 5 different levels of inclusion toward 3 different concentrations of OTA.

The sequestration of OTA from wine was evaluated using a standard procedure for sequestration of mycotoxin on the original best performing MIP #523-34 (phenol-cyclohexane mixture. Sequestration varied on average from 43.29±4.08 to 67.15±4.94 to 91.75±1.59 to 95.612±1.201% for a level of inclusion of 0.05, 0.10, 0.50, and 1.00 g/L, respectively. The titration of the MIP determined an optimum affinity when used at a level of inclusion of 0.5 and 1.0 mg/mL (See FIG. 5).

Thus, in some embodiments, the present invention provides compositions and methods of using the same for trapping/adsorbing mycotoxins (e.g., OTA) from wine (e.g., MIP particles that are utilized (e.g., under shaking conditions) to effectively bind to and adsorb mycotoxins from the wine).

For example, in some embodiments, the present invention provides MIPs (e.g., generated according to a method described herein) for trapping and/or adsorbing mycotoxins (e.g., one or a plurality of different types of mycotoxins (e.g., present in liquid media or extraction solution from complex matrix (e.g., feed, food, vegetal, animal, etc.)).

Solid Phase Extraction-like (SPE-like) filtering devices were generated for an equivalent of 0.1 g/L of inclusion of the MIP. Silanized glass vials were needed to ensure the stability of OTA in aqueous solvents and to prevent any aspecific interaction between OTA and the glass vials. The method of silanization was applied to nylon and PTFE/PE filters and tubes based on methods generally used in the art (See, e.g., Entwisle et al., 2000 as cited previously). The vials and filters were prepared by filling them or immersing them with silanizing reagent (SURFASIL). After 1 minute, they were rinsed once with toluene then twice with methanol followed by three times with water and dried. Silanization was performed and generated a dramatic reduction of the interaction of the material with OTA molecule as performed in the field. For example, less than 5% of interference was observed (e.g., in contrast to about 16 to 26% interference without prior silanization of the materials when PE/PTFE filters are used). Nylon was not suitable for silanization. All the polypropylene tubes were replaced with silanized glass tubes.

SPE-like filtering devices were generated to trap OTA from wine after a direct filtration of the sample through the column. The efficacy of the MIP was tested for OTA clearance from wine (Chardonnay 2005—California) spiked with 5 and 10 ppb of OTA. The results demonstrated for 5 and 10 ppb of spiked OTA, a 55.41±5.542 and 56.937±5.739% instant reduction of the OTA content of the wine, respectively. Accordingly, in some embodiments, the present invention provides mycotoxin-specific MIPs (e.g., generated according to methods described herein) that are utilized with a SPE or SPE-like filtering device for removing mycotoxins from liquid (e.g., wine) comprising mycotoxins.

Example 10

Trapping of Ochratoxin a Using Heat Initiated and Low Temperature UV Initiated MIP Solid Phase Extraction (SPE)-like Filtering Device and Selectivity Evaluation Toward Key Constituents of Wine Solid Phase Extraction-like (SPE-like) filtering devices were generated for an equivalent of 0.1 g/L of inclusion of the MIP. Silanized glass vials were needed to ensure the stability of OTA in aqueous solvents and to prevent any a specific interaction between OTA and the glass vials. The method of silanization was applied to nylon and PTFE/PE filters and tubes based on methods generally used in the art (See, e.g., Entwisle et al., 2000 as cited previously). The vials and filters were prepared by filling them or immersing them with silanizing reagent (SURFASIL). After 1 minute, they were rinsed once with toluene then twice with methanol followed by three times with water and dried. Silanization was performed and generated a dramatic reduction of the interaction of the material with OTA molecule as performed in the field. For example, less than 5% of interference was observed (e.g., in contrast to about 16 to 26% interference without prior silanization of the materials when PE/PTFE filters are used). Nylon was not suitable for silanization. All the polypropylene tubes were replaced with silanized glass tubes.

The stock solutions of twelve compounds including polyphenols: caffeic acid (Caf A), catechin hydrate (CH), epicatechin (ECH), ferulic acid (Fer), trans-3-hydroxycinnamic acid (3-HCA), 2-hydroxycinnamic acid (2-HCA), malvidin-3-galactoside chloride (Mal), myricetin (Myr), quercetin dehydrate (QH), trans-resveratrol (Res), rutin trihydrate (Rut) and indole-3-acetic acid (IAA) (Sigma, St Louis, Mo., USA) were prepared by dissolving in methanol (HPLC grade) and adding water and 85% o-phosphoric acid to lower the pH to approximately 3.0. The supernatant was collected in amber and silanized HPLC vials, preventing any interaction of the analyte with the vial, and calculated from HPLC (Alliance, Waters Corp., Milford, Mass., USA) coupled to fluorimetric and diode-array detectors signal (e.g., to detect amounts of mycotoxin and mycotoxin sequestered). A C18 reversed-phase HPLC Spherisorb ODS column 5 µm, 4.6 µm×250 mm (Waters Corp., Milford, Mass., USA) thermostated at 30° C. was used. Excitation and emission wavelengths were set to 225 nm and 365 nm, respectively. The UV-photo diode array detector was set to full scan mode from 210 to 799 nm wavelengths. The mobile phases consisted of water/phosphoric acid (99.5%:0.5%; v/v) and (B) acetonitrile (HPLC grade)/water/phosphoric acid (50%/49.5%/0.5%; v/v/v).

All MIPs showed good adsorption of OTA in buffer solution, all over 80% adsorption. MIP 555-52 showed the best adsorption, nearly 100%. Interestingly, OTA stayed adsorbed during the buffer wash of all MIPs, but desorbed during the methanol wash specifically from the heat-initiated MIP #555-52 and #523-34 and significantly at the highest OTA concentration. The OTA stayed adsorbed to the low temperature and UV-initiated MIP #555-54A and #555-54B in the methanol wash better than to the heat-initiated MIPs, with over 50% adsorption on average to the UV-initiated MIPs maintained through the methanol wash (See FIG. 6).

Figure 6:
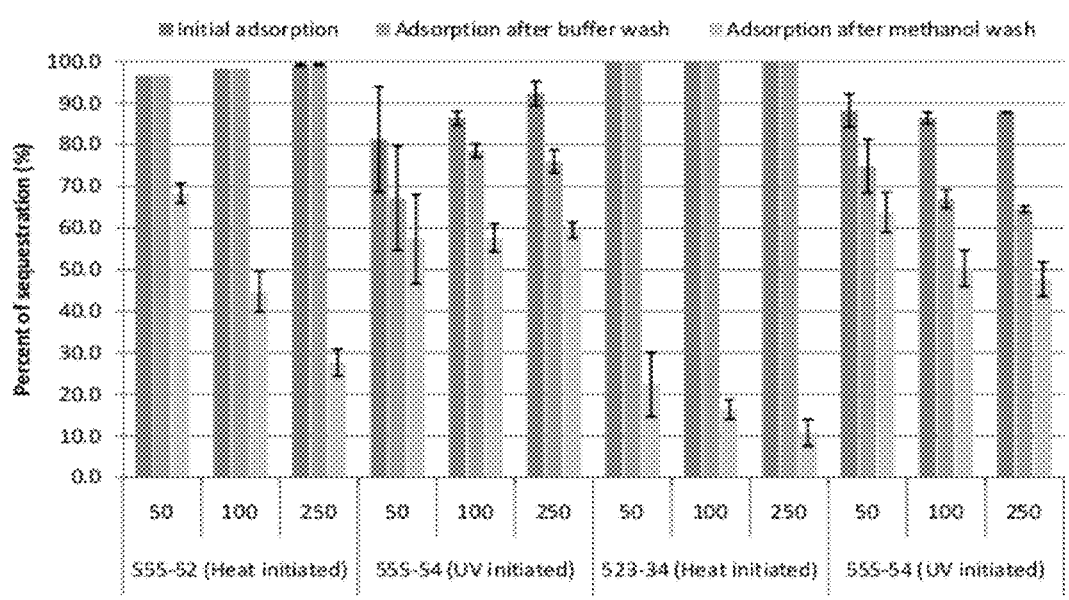
FIG. 6 shows the sequestration activity for OTA by MIPs made of styrene and 2-vinylpyridine as functional monomers and polymerized with either heat-initiation or low temperature and UV-initiation. Values of the initial adsorption and remnant adsorption after citrate buffer wash (pH 4.0) and after 100% methanol wash are reported.

Health benefits of antioxidant polyphenol compounds in wine are well documented. In the strategy of filtering mycotoxin in liquid (e.g., wine) such as OTA, it is also primordial to evaluate the impact of the sequestrants material on some of the beneficial compounds such as polyphenols. In some embodiments and as documented herein (See e.g., Example 6 to Example 9) heat-initiated polymerization producing MIP #555-52 and #523-34 were able to interact effectively with OTA mycotoxin present in a liquid media, with adsorption levels above 95% whereas low temperature and UV-initiated polymerization producing MIP #555-54 and #555-54X gave adsorptive efficacy ranking between 80 and 92% of sequestration efficacy (FIG. 6).

Figure 7:
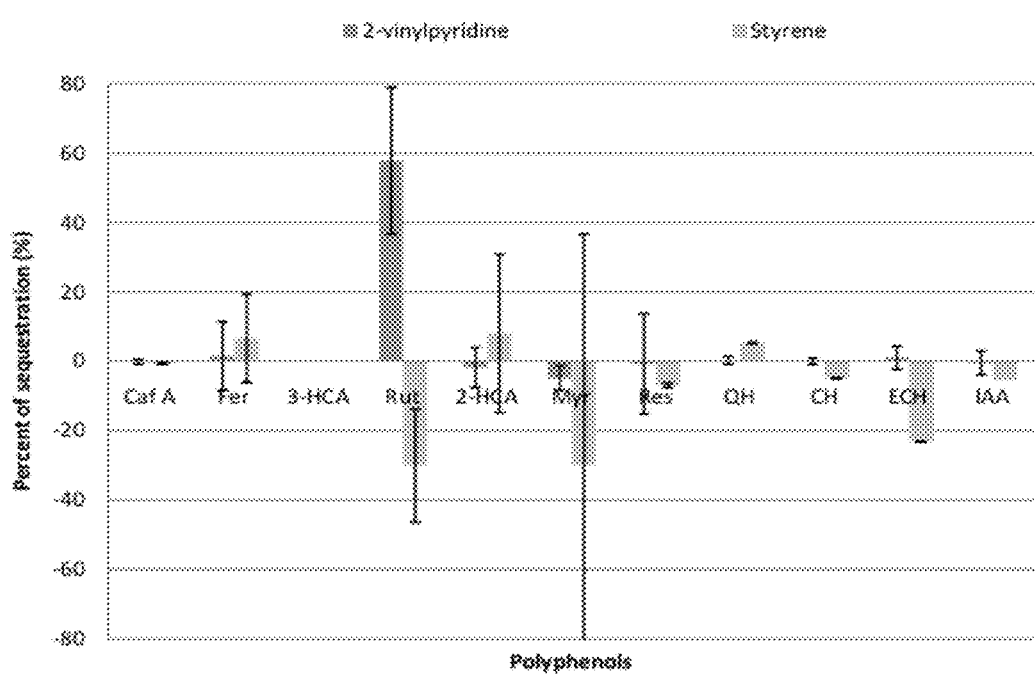
FIG. 7 shows the sequestration activity for polyphenols and 3-indol acetic acid by MIPs made of styrene and 2-vinylpyridine as functional monomers and polymerized with low temperature and UV-initiation. Values of the initial adsorption are reported.

In some embodiments, the low temperature and UV-initiated MIP compositions of the invention display d specificity for the OTA when evaluated with a mixture of different polyphenols, an anthocyanin, and indole-3-acetic acid. In this case, MIP #555-54A and #555-54B displayed high adsorption of OTA (above 80%) and prevented at the same time the adsorption of the polyphenols or indole-3-acetic acid (e.g., that provide the organoleptic and anti-oxidant characteristics (e.g., of wine)). In the study of the UV-initiated MIPs, the incubation time was eliminated and wine samples and washings were pushed through the MIP or filter immediately. Very little adsorption was observed (FIG. 7). Thus, in some embodiments, the invention provides a MIP that displays specificity for a mycotoxin (e.g., OTA) while concurrently displaying little to no binding to (e.g., adsorption of) beneficial compounds (e.g., polyphenols and/or indole-3-acetic acid). The quantification of the myricetin, resveratrol and rutin were prone to uncertainty due to their presence at very low concentration close to the limit of detection and limit of quantification of the HPLC analytical instrument giving as a consequence large standard deviations and negative values. In the present embodiment, the UV-initiated MIPs were thus efficient in the trapping of OTA and were not impairing the polyphenol content of a wine liquid medium demonstrating the specificity of the MIP material generated.

Example 11

Coating of MIP on Fiberglass Mesh for Application as a Filtering Device

Figure 8:
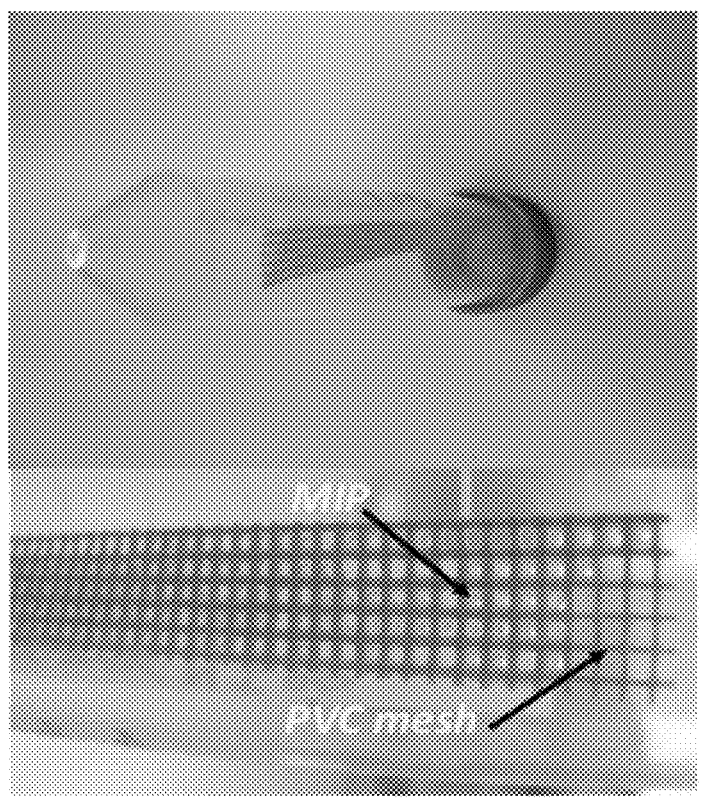
FIG. 8 shows photos of fiberglass mesh coated with MIP-OTA and used in a 50 mL falcon tube for OTA sequestration in wine.
Figure 9:
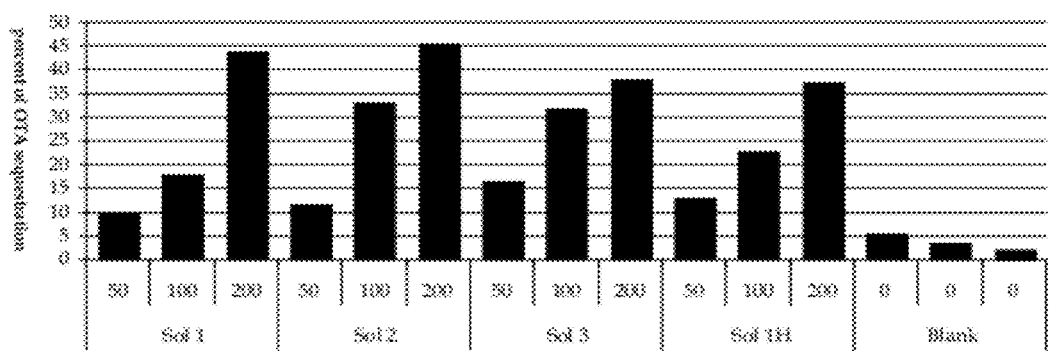
FIG. 9 shows the results of sequestration testing of three levels of MIP-OTA coated on fiberglass mesh using four different polymerization conditions and tested with white wine comprising spiked concentrations of 50, 100, 200 ppb of OTA.
Figure 10:
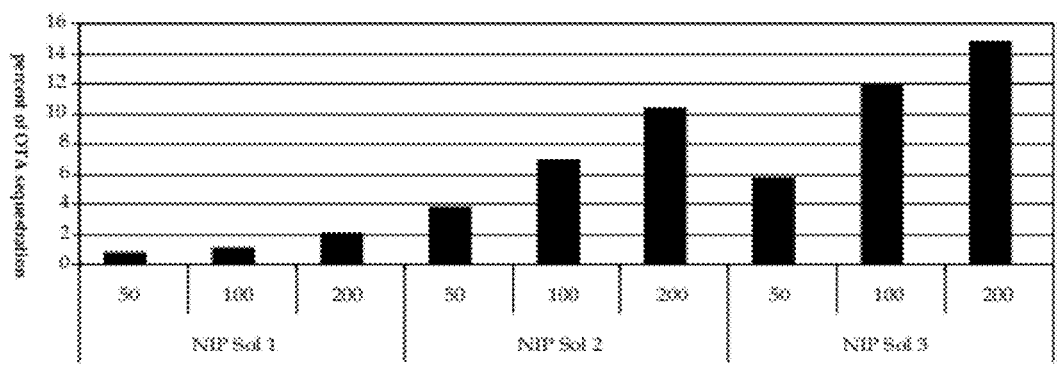
FIG. 10 shows the results of the sequestration testing of three levels of NIP coated on fiberglass mesh using 3 three polymerization conditions and tested in white wine for spiked concentrations of 50, 100, 200 ppb of OTA.
Figure 11:
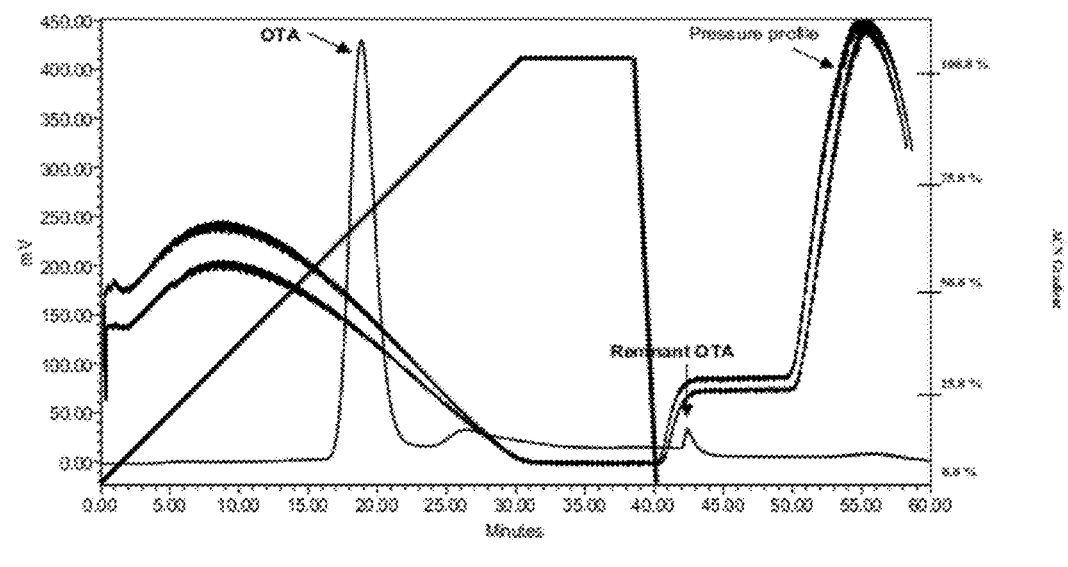
FIG. 11 shows a chromatographic profile of standard solutions of OTA recorded with a fluorescent detector and gradient selection utilized to optimize the time of retention of the mycotoxin.

Experiments were conducted during development of embodiments of the invention to test coating of fiberglass mesh with MIP-OTA (See FIG. 8). Multiple concentrations of OTA were used to determine the affinity of each preparation. The different MIPs generated are summarized in Table 7 below. Three mesh screens were coated with MIP's with varying concentrations of cross linking reagent, which affects brittleness. (Monomer solutions 1, 2, 3 and 1H). Mesh that was prepared from coated MIPs was cut based on weight before and after the coating of MIP to give 50, 100 and 200 mg of MIP evaluated by differential weighting. Sequestration assays were conducted with MIP coated mesh submerged in a 20 mL falcon tube, with determination of sequestration characteristics to OTA in wine media after 90 min incubation using a rotary shaker. One mL from the tubes containing the wine solution spiked with three different concentrations of OTA was measured before and after incubation with the MIP-OTA mesh filters. The sample was collected in amber and silanized HPLC vials, preventing any interaction of the mycotoxin with the vial, and calculated with HPLC (Alliance, Waters Corp., Milford, Mass., USA) coupled to fluorometric and diode-array detectors signal (e.g., to detect amounts of mycotoxin and mycotoxin sequestered).

TABLE 7

Description of the polymerization conditions for the coating of MIP on fiberglass mesh.

| | | Monomer Solution | | | |
|---|---|---|---|---|---|
| Parameters | Function | 1 | 2 | 3 | 1H |
| Ochratoxin A analog (mg) | template | 1000 | 500 | 250 | 1000 |
| 2-Vinyl pyridine (μl) | Base to form salt with OTA | 1000 | 500 | 250 | 1000 |
| Ethylene glycol Dimethacrylate (mL) | Cross linker | 5 | 5 | 5 | 5 |
| 2-Hydroxy ethyl methacrylate (μl) | Binding molecule | 800 | 400 | 200 | 800 |
| Azobisisobutyro-nitrile (mg) | Initiator of polymerization | 66 | 55 | 50 | 66 |
| Curing (oven) | For Drying of mesh | 65° C. | 65° C. | 65° C. | 80-90° C. |
| Solvent | Dissolve solids | none | none | none | 500 μl toluene |

Results indicated that maximum sequestration against OTA was dependent on the level of inclusion of the MIP. The sequestration maximum was obtained with 500 mg of template, 250 mg vinyl-pyridine and 200 mg of hydroxylethyl methacrylate that produced a MIP that adsorbed up to 46.5% of OTA of the 100 ppb concentration in wine (See FIG. 9). Conversely, the same experiment carried out with identically processed NIP polymer coated on fiberglass showed less than 15% (down to 1%) of sequestration efficacy depending on the preparation procedure (See FIG. 10) thereby exemplifying the specificity of the MIP-OTA material for OTA.

Example 12

Chromatographic Retention Capacity of MIP's

MIP #523-34 (synthesized with toluene-cyclohexane mixture) was used as static phase of a 4.6×150 mm HPLC column after packing the material using sonication in a water-bath and then applying a continuous overnight flow rate of 5.0 mL/min of acetonitrile run through the column (MIP using an HPLC Waters Alliance binary pump (Waters Corp, Milford, Mass., USA)). The column pressure was determined to be about 400 psi and was comparable to other HPLC conditions described elsewhere (See, e.g., Baggiani et al., 2002 as previously cited; Jodlbauer J., Maier N. M., and Lindner W. Journal of Chromatography A, 945: 45-63; Maier N. M., Buttinger G., Welhartizki S., Gavioli E., Lindner W., 2004. Journal of Chromatography B, 804: 103-11). The column was stabilized under acetonitrile flow rate at 1.0 mL/min over 48 h and extensively washed with methanol 99% and tetraethylamine 1% to remove remaining OTA template from the column. Characterization of frontal HPLC-PDA-FID analysis of OTA using the MIP column was performed.

The survival of the column was evaluated under different mobile phase conditions and under different gradient settings run through the column maintained at a constant temperature of 30° C. Several gradients were tested including 100% water and transitioning to 100% acetonitrile or 100% methanol and vice versa; and also using tetraethylamine 1% in methanol to methanol 100% for 60 min. The column survived without any modification in the static phase after an increase of pressure up to 1600 psi accounting for survival of the column at high pressures. Injection of acetone was used to evaluate the void volume of the column with an elution of the analyte over a period of 2 min. OTA elution was evaluated using the same conditions used for a regular ODS C18 elution profile (85% acetonitrile). The retention of OTA was evaluated at 5 min with the MIP column under isocratic gradient. To increase the retention time of OTA, a gradient was implemented that allowed the retention of OTA to increase to 19.5 min.

The final conditions selected are presented in FIG. 11 and the gradient condition detailed in associated table. Two peaks were observed, the principal peak of OTA eluting between 17 and 22 min (at 63% of acetonitrile) and a second peak associated with a remnant highly bound OTA fraction released by the addition of tetraethylamine 1% to the column.

Example 13

Sporidesmin Template Synthesis

Preparation of N-tert-butoxycarbonyl-2,3-dimethoxyaniline from 2,3-dimethoxybenzoic acid. Three hundred milliliters of anhydrous tert-butyl alcohol, 50.0 g (274 mM) 2,3-dimethoxybenzoic acid and 28.33 g (280 mM, 39 mL) anhydrous triethylethylamine are charged into a 1 L, round bottom, two necks flask, equipped with a 120 mL dropping funnel with pressure equilibration and gas bubble-meter, heavy magnetic stirring bar and a thermometer. The content of the flask is magnetically stirred and heated to 80° C. in an oil bath. An amount of 77.04 g (280 mM, 60.5 mL) of diphenyl phosphorazidate is added drop-by-drop into the mixture with a slow enough rate to control gasses production evolution. Heating to 80° C. and magnetic stirring was maintained overnight. The volatile components of the mixture were then rotary evaporated under 30 T vacuum and at a temperature below 55° C. The oily product was transferred into a 1 L separatory funnel and dissolved in a mixture of 500 mL cyclohexane and 200 mL of ethyl acetate. The solution was washed three times with 200 mL DI water and once with 200 mL of saturated aqueous sodium chloride and dried over anhydrous sodium sulphate for 15 min, filtered and concentrated in rotary evaporator under 30 T vacuum at 80° C. N-tert-butoxycarbonyl-2,3-dimethoxyaniline 67.88 g (98% yield) were obtained as colorless oil.

TLC, $SiO_2$, $CH_2Cl_2$:cyclohexane (abbreviated as c-Hex) (1:2); $R_f$=0.66 detection UV, hot 5% $KMnO_4$ bright yellow.

FT-IR film ($cm^{-1}$): 3319, 2941, 1669, 1601, 1529, 1477, 1459, 1416, 1369 1296, 1258, 1090, 998, 978, 780, 737.

$^1$H NMR, (400 MHz), $CDCl_3$, δ (ppm): 1.53 s, 9H, 3.86 s, 3H, 3.862 s, 3H; 6.593 dd, J=8.4&1.6 Hz, 1H, 7.004 t, J=8.4&8.0, 1H, 7.135 br s, 1H, 7.725 d, J=8.0 Hz.

Preparation of 2,3-dimethoxyaniline from N-tert-butoxycarbonyl-2,3-dimethoxyaniline. A volume of 580 mL of methanol, 67.88 g (268 mM) of N-tert-butoxycarbonyl-2,3-dimethoxyaniline and 66.45 mL of 12.1 M HCl were charged to a 1 L flask equipped with a magnetic stirring bar and placed in a water bath of 50° C. Heating and stirring was maintained for 2 h and then left with stirring overnight at ambient temperature. Then, after cooling of the solution in an ice bath, a volume of 130.5 mL of 6.16 M sodium hydroxide was added with stirring.

Methanol was evaporated from the mixture using a rotary evaporator at a temperature below 40° C. and under vacuum pressure of 30 T. The semi solid residue was diluted with 180 mL of toluene and filtered. The precipitate was washed two more times with 180 mL portions of toluene and the filtrates were transferred into a 1 L separatory funnel. The upper layer was collected and dried with sodium sulphate, concentrated and vacuum distilled. A mass of 34.6 g of 2,3-dimethoxyaniline (94.0% yield) was collected at 105-107° C. at 8 T in form of colorless, crystallizing oil.

TLC, $SiO_2$, c-Hex:Tetrahydrofuran (abbreviated as THF) (6:1); $R_f$=0.35 detection UV, 5% $KMnO_4$ heat/brown-green.

FT-IR film ($cm^{-1}$): 3463, 3368, 2939, 1609, 1497, 1475, 1319, 1262, 1226, 1129, 1085, 1050, 999, 773, 729, 694.

$^1$H NMR, (400 MHz), $CDCl_3$, δ (ppm): 3.75 br s, 2H, 3.83 s, 3H, 3.84 s 3H, 6.34 d, J=8.1 Hz, 1H, 6.38 d, J=8.1 Hz, 1H, 6.84 t, J=8.1 Hz, 1H.

Synthesis of ethyl 3-hydroxy-6,7-dimethoxy-2-indolone-3-carboxylate from 2,3-dimethoxyaniline and diethylketomalonate. A solution of 69.33 g (398.1 mM) of diethylketomalonate in 250 mL of toluene is placed in a 1 L round bottomed flask equipped in a dropping funnel with air equilibration and a magnetic stirring rod placed in an ice-water bath. A solution of 56.769 g (370.6 mM) of 2,3-dimethoxyaniline in 200 mL of toluene is charged into the dropping funnel. The stirring is started and 2,3-dimethoxyaniline solution is slowly added into the flask, with continuous cooling and magnetic stirring of the reaction mixture. The addition was completed in 4 hrs time and the mixture was allowed to warm up to room temperature and left with stirring overnight for a total of 22 h. Then, the mixture was heated to 80° C. for 2 hrs and followed by an increase of the temperature of the mixture to 100° C. A volume of 25 mL of the distillate was collected. A volume of 25 mL of the distillate was collected, including 4 mL of water and 21 mL of toluene. A TLC $SiO_2$ (PhMe:THF/6:1, UV, hot $KMnO_4$ indicated the presence of: diethylketomalonate $R_f$ 0.86; 2,3-dimethoxyanilide of monoethylketomalonate $R_f$ 0.66; 2,3-dimethoxyaniline $R_f$ 0.43; diethylketomalonate monohydrate $R_f$ 0.30 and the desired product, ethyl 3-hydroxy-6,7-dimethoxy-2-indolone-3-carboxylate $R_f$ 0.20. Heating to 100° C. was continued for 24 hrs after which a white precipitate was formed in the flask. The content of the flask was then stirred and heated at 80-90° C. for the next 48 h. After this time it was cooled to room temperature and the precipitate was filtered off and washed with 50 mL of toluene. After drying, 16.1 g of ethyl 3-hydroxy-6,7-dimethoxy-2-indolone-3-carboxylate (24.0% yield) were obtained. The filtrate was concentrated in a rotary evaporator and subjected to LC on $SiO_2$ using c-Hex:THF mixture with THF content from 7.5 to 20%. Additional 12.2 g (18.2% yields) of fairly pure product were collected.

Mp 150-151° C.

TLC, $SiO_2$, Toluene (abbreviated as PhMe):THF (6:1), $R_f$=0.12 detection UV, 5% $KMnO_4$ heat/canary-yellow.

FT-IR film ($cm^{-1}$): 3293, 2937, 1728, 1726, 1636, 1505, 1466, 1336, 1236, 1234, 1164, 1084, 1016, 1192, 729.

$^1$H NMR, (400 MHz), $CDCl_3$, δ (ppm): 1.191 t, J=7.2 Hz, 3H, 3.892 s, 3H, 3.898 s, 3H; 4.152-4.319 m, 16 lines, dqx2, all J=7.2 Hz with the quartets centers at: 4.179, 4.205, 4.265, 4.292, 2H, 4.346 br s, 1H, 6.575 d, J=8.4 Hz, 1H, 6.961 dd, J=8.4&0.4 Hz, 1H, 7.744 br s, 1H.

Synthesis of 6,7-dimethoxyisatine from ethyl 3-hydroxy-6,7-dimethoxy-2-indolone-3-carboxylate. A solution of 10.67 g (40.2 mM) of ethyl 3-hydroxy-6,7-dimethoxy-2-indolone-3-carboxylate in 100 mL of ethanol was stirred in water bath of ambient temperature. Into this mixture a solution of 4.828 g (120.7 mM) of sodium hydroxide in 25 mL of water was added drop by drop. A stream of air, free of $CO_2$, was passed by the reaction mixture which was vigorously stirred. Air passing and stirring of the mixture at ambient temperature was maintained overnight. The recovered mixture was intense red-brown. The solution was neutralized by the addition of 5 mL of concentrated hydrochloric acid. The white precipitate of inorganic salts that formed was filtered off and the filtrate was concentrated in a rotary evaporator to 20 mL volume and left for crystallization in refrigerator. The orange-yellow crystals were collected and air dried. An amount of 2.24 g (26.9% yield) of pure 6,7-dimethoxyisatine was obtained. An additional 0.54 g (6.5% yield) of the product was separated from the filtrate by liquid chromatography using $SiO_2$ and PhMe:THF (4:1) mixture.

Mp 209-210° C.

TLC, $SiO_2$, PhMe:THF (6:1), $R_f$=0.18 yellow spot, detection UV, 5% $KMnO_4$ heat/canary-yellow.

FT-IR film ($cm^{-1}$): 3218, 1747, 1707, 1623, 1507, 1452, 1442, 1337, 1286, 1240, 1184, 1082, 1041, 973, 949, 794, 685, 702, 662.

$^1$H NMR, (400 MHz), $CDCl_3$, δ(ppm): 3.91 s 3H, 3.98 s 3H, 6.60 d, J=8.4 Hz, 1H, 7.42 d, J=8.4 Hz, 1H, 7.74 br s, 1H.

Synthesis of 6,7-dimethoxy-1-methylisatine from 6,7-dimethoxyisatine. A solution of 2.255 g (20.1 mM) of potassium tert-butanolate in 20 mL of anhydrous THF was added from a syringe by rubber septum, with magnetic stirring and cooling in an ice-water bath, into a 50 mL round bottom flask containing a solution of 2.78 g (13.4 mM) of 6,7-dimethoxyisatine in 15 mL of anhydrous THF. Into this mixture 3.8 mL (8.65 g, 60 mM) of methyl iodide were added by means of a syringe and the mixture with heavy precipitate that formed immediately was stirred overnight at 35° C. TLC ($SiO_2$, PhMe:THF (6:1)) confirmed full conversion of the substrate (6,7-dimethoxyisatine) $R_{f=0.18}$ into the 6,7-dimethoxy-1-methylisatine $R_{f=0.34}$. The precipitate was filtered off and washed with three 20 mL portions of anhydrous THF. The combined filtrates were evaporated to dryness and the product was collected as a bright red colored fraction from flash chromatography. $SiO_2$ and a mixture of PhMe:THF (9:1) was used. After evaporation to dryness of the red colored eluent, 2.517 g (84.8% yield) of bright yellow crystals were collected.

Mp 190-191° C.

TLC, $SiO_2$, PhMe:THF (6:1), $R_f$=0.34 orange-red spot, detection UV, 5% $KMnO_4$ heat/canary-yellow.

FT-IR film (cm$^{-1}$): 2955, 1724, 1614, 1497, 1450, 1373, 1264, 1205, 1168, 1131, 1086, 1044, 1028, 979, 975, 828, 800, 775, 654.

$^1$H NMR, (400 MHz), $CDCl_3$, δ (ppm): 3.490 s, 3H, 3.877 s, 3H, 3.982 s, 3H, 6.575 d, J=8.4 Hz, 1H, 7.416 d, J=8.4 Hz, 1H.

Synthesis of 5-chloro-6,7-dimethoxy-1-methylisatine. An amount of 2.517 g (11.38 mM) of 6,7-dimethoxy-1-methylisatine and 1.823 g (13.65 mM) of N-chlorosuccinimide and 30 mL of DMF were placed in a 100 mL round bottom flask equipped with a magnetic stirring bar and a 10 mL dropping funnel with air equilibration and placed in an ice-water bath. A 10 mL solution of 1.125 mL (13.6 mM) of concentrated hydrochloric acid in DMF was charged into the dropping funnel and added drop by drop into a stirred and cooled reaction mixture. After addition was completed, the solution was mixed at ambient temperature for additional 2 h. Then the solvents were rotary evaporated under 8 T vacuum and at 50° C. and the residue was subjected to flash chromatography on $SiO_2$ using PhMe:THF (19:1) mixture. An eluent containing a brick-red band of the product was collected and rotary evaporated to dryness yielding 1.83 g (62.9% yield) of brick-red crystals of 5-chloro-6,7-dimethoxy-1-methylisatine.

Mp 140-142° C.

TLC, $SiO_2$, PhMe:THF (6:1), $R_f$=0.51 red spot, detection UV, 5% $KMnO_4$ heat/canary-yellow.

UV/VIS (nm) c.-0.143 mg/mL in Ethanol: 318, e 2.75, 433, e 0.70.

FT-IR film (cm$^{-1}$): 2951, 1726, 1602, 1457, 1442, 1423, 1404, 1359, 1292, 1263, 1232, 1093, 1046, 1005, 979, 941, 897, 881, 797, 766, 668.

$^1$H NMR, (400 MHz), $CDCl_3$, δ (ppm): 3.475 s, 3H, 3.935 s, 3H, 4.027 s, 3H; 7434 s, 1H.

Figure 13:
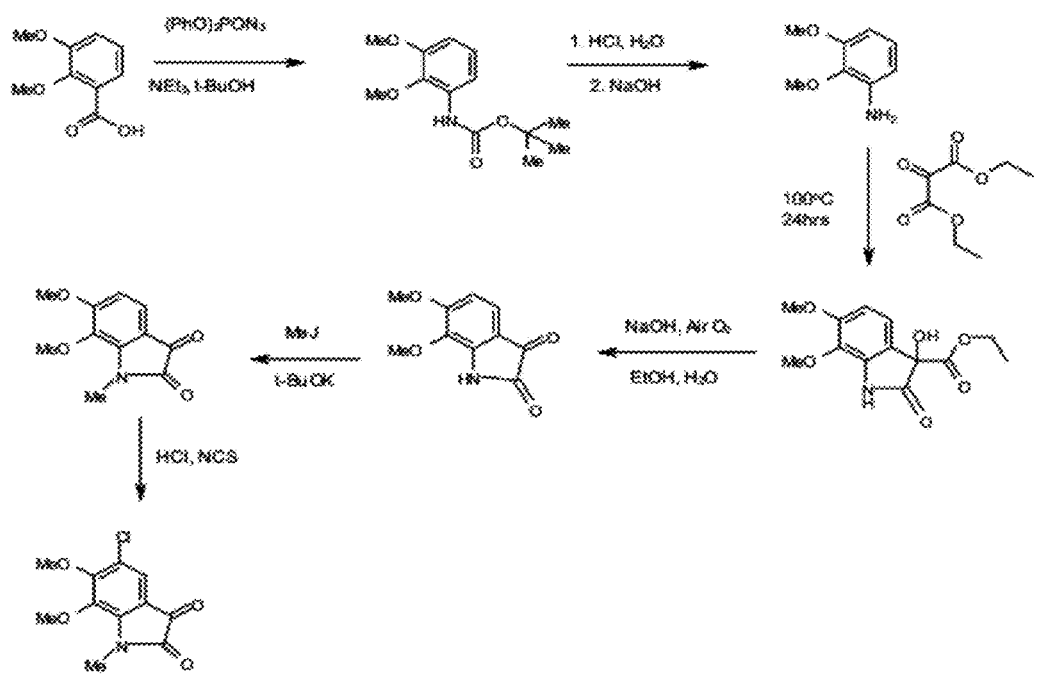
FIG. 13 shows the sporidesmin template pathway synthesis.

The molecular structure of sporidesmin and the of 5-chloro-6,7-dimethoxy-1-methylisatine template can be found in FIG. 12. The synthetic pathway is summarized in FIG. 13.

Example 14

Sporidesmin MIP and NIP Synthesis (with Methacrylic Acid)

A solution of 1.8 g (7.04 mM) of 5-chloro-6,7-dimethoxy-1-methylisatine, 1.194 mL (1.212 g, 14.08 mM) of methacrylic acid, 3.415 mL (3.664 g, 28.16 mM) of 2-hydroxyethylmethacrylate, 39.83 mL (41.86 g, 211.2 mM) of ethylene glycol dimethacrylate and 1.0 g (6.09 mM) of AIBN in 100 mL of toluene is placed in a 500 mL, four neck round bottom flask equipped with a 120 mL dropping funnel with gas equilibration, a mechanical stirrer, a reflux condenser with bubble-meter and a thermometer. A volume of 120 mL of toluene is placed in the dropping funnel, the stirrer is started and nitrogen is passed through the toluene (in the dropping funnel) and over the surface of the mixture in the flask and released outside through the bubble-meter. After 30 min of stirring and blowing nitrogen, the rate of gas flow is limited to single bubbles and the temperature in the flask is increased to 65° C. by immersing the flask in a water bath of 70° C. Within 15 min polymerization starts and the solution becomes more and more viscous. When it is difficult to maintain a vigorous agitation, the toluene from the dropping funnel is added as fast as possible, to dilute the mixture. Vigorous agitation and heating is maintained for 4 h. During this time small spheres of the MIP are formed. The mixture is left without stirring or heating overnight. In the morning MIP spheres are filtered off and washed 13 times with 150 mL of ethanol each. The orange red colored filtrates are collected, rotary concentrated. The 5-chloro-6,7-dimethoxy-1-methylisatine (sporidesmin template) is recovered by flash chromatography using PhMe:THF (98:2) and collecting brick-red band of the template. Rotary evaporation yielded 1.572 g (87.3% recovery) of very pure, crystalline 5-chloro-6,7-dimethoxy-1-methylisatine. The spheres of MIP are air dried overnight at ambient temperature and one additional hour at 80° C. in a laboratory oven.

A quantity of 45.362 g of sporidesmin MIP (methacrylic acid) were obtained in form of small egg-shell white spheres and identified as MIP #519-98.

Sporidesmin NIP (methacrylic acid) 45.883 g in form of snow-white spheres, was obtained by following the same procedure however no sporidesmin template have been added to the reaction mixture and only three ethanol washes (150 mL each) were performed. The polymer was identified as MIP #555-99.

Both MIP and NIP were easy to filter and wash on sintered glass filter.

Example 15

Sporidesmin MIP and NIP Synthesis (with 2-vinylpyridine)

A solution of 1.5 g (5.86 mM) of 5-chloro-6,7-dimethoxy-1-methylisatine, 1.260 mL (1.232 g, 11.72 mM) of 2-vinylpyridine, 2.845 mL (3.053 g, 23.46 mM) of 2-hydroxyethylmethacrylate, 33.191 mL (34.833 g, 176 mM) of ethylene glycol dimethacrylate and 0.833 g (5.07 mM) of AIBN in 80 mL of toluene is placed in a 500 mL, four neck round bottom flask equipped with a 100 mL dropping funnel with gas equilibration, a mechanical stirrer, a reflux condenser with bubble-meter and a thermometer. A volume of 120 mL of toluene is placed in the dropping funnel, the stirrer is started and nitrogen is passed through the toluene (in the dropping funnel) and over the surface of the mixture in the flask and released outside through the bubble-meter. After 30 min of stirring and blowing nitrogen the rate of gas flow is limited to single bubbles and the temperature in the flask is increased to 65° C. by immersing the flask in a water bath of 70° C. Within 15 min polymerization starts and the solution becomes more and more viscous. When it is difficult to maintain a vigorous agitation, the toluene from the dropping funnel is added as fast as possible, to dilute the mixture. Vigorous agitation and heating is maintained for 4 h. During this time small spheres of the MIP are formed. The mixture is left without stirring or heating overnight. Then, MIP spheres are filtered off and washed 13 times with 150 mL of ethanol each. All filtrates from washing MIP's are collected and rotary evaporated to dryness. The red colored residue is dissolved in 20 mL of toluene and applied to the top of a liquid chromatography column (24 mm×50 cm) filled with 200 mL $SiO_2$ in toluene. The red band is washed with PhMe:THF (5:1). Rotary evaporation yielded 1.489 g (99.2% recovery) of crystalline 5-chloro-6,7-dimethoxy-1-methylisatine. The spheres of MIP are air dried overnight at ambient temperature and for two more hours at 80° C. in a laboratory oven. An amount of 37.936 g of sporidesmin MIP (2-vinylpyridine) were obtained in form of small egg-shell white spheres and identified as MIP #519-101.

Sporidesmin NIP (2-vinylpyridine). An amount of 39.2 g in form of snow-white spheres, was obtained following the same procedure, however no sporidesmin template have been added to the reaction mixture and only three ethanol washes (150 mL each) were performed. The polymer was identified as MIP #555-102.

Example 16

UV Initiated, Low Temperature Polymerization/Synthesis of Sporidesmin MIP's

Photochemical reaction set. Quartz, photochemical UV immersion well (Ace Glass, Catalogue # 7856-10) equipped in 450 Watt UV Lamp (ACE Glass, Catalogue# 7825-34) and 450 Watt Cased Power Supply (ACE Glass, Catalogue#7830-58) is attached to a circulation chiller WKL 230 LAUDA (supplied by Brinkmann Instuments, Inc.), and cooling water of 4° C. is run through the well mantle at the time when the UV lamp is on.

Polymerization process. A mixture of monomers: methacrylic acid 1.2 g (13.95 mM) and ethylene glycol monomethacrylate 3.631 g (13.95 mM), sporidesmin template 1.783 g (6.97 mM), initiator (IABN) 0.991 g (6.03 mM) and a crosslinker, ethylene glycol dimethacrylate 41.444 g (209.1 mM) are placed in a translucent, polyethylene bottle (Nalgene®style 2105) and a stream of Argon is passed through the mixture for 15 min to remove all of the oxygen, which is known to inhibit free radical polymerization. The bottle is then closed and attached to the immersion well, at the level of the UV lamp center, and immersed, together with the photochemical reaction set, into an ice-water bath. Cooling water is run through the lamp mantle, when the light is turned on, and the reaction mixture irradiation is maintained for three and half hours (UV safety glasses are required at the time when the UV lamp is on). Additional ice is supplied to, and excess of water is drained from the bath during the course of the UV polymerization, to maintain cooling bath temperature at 4° C. After completing polymerization the bottle is open, the polymer is crushed and grinded into small pieces which are washed: three times with ethanol, two times with 1:1 water-ethanol mixture, six times with 3:1 water-ethanol mixture and one more time with ethanol, to remove the template from the polymer and secure maximum activity of MIP which is finally dried in a laboratory oven, to remove ethanol residues yielding 41.1 g (89% yield) of the product.

Example 17

MIPs' Sequestration Capabilities Toward Mycotoxins—Applied to Sporidesmin Analogs MIP and NIP polymers produced by heat initiated precipitation polymerization either using methacrylic acid or 2-vynilpyridine monomers in toluene (See e.g., Example 14 and Example 15) were tested toward 5-chloro-6,7-dimethoxy-1-methylisatine template (See e.g., Example 13) and gliotoxin, an analog to the sporidesmin molecule containing the similar disulphide-bridged piperazinedione ring system (Sigma-Aldrich, St. Louis, Mo., USA) for the removal of the template and gliotoxin mycotoxins from liquid or semi-liquid media via chemical interactions. The MIPs and NIPs produced were used herein to depict the differences in affinity of sequestration. A sequestration experiment was conducted by weighing 400 mg of MIP/NIP material into amber Schott bottles and addition of 100 mL of a working solution of the analyte investigated to obtain a inclusion rate of 0.4 g/L of the sequestrants in the medium. The preparation was made together with a blank sample containing no MIP material and a positive control containing either the 5-chloro-6,7-dimethoxy-1-methylisatine template or gliotoxin. The sequestration test was performed in citrate buffer 50 mM adjusted to pH 4.0. All samples were incubated during 90 min on an orbital rotary shaker (Brunswick, Champaign, Ill., USA) at 150 rpm maintained at a temperature of 37° C. Five final concentrations of 5-chloro-6,7-dimethoxy-1-methylisatine template or gliotoxin were tested with the system—500; 1,000; 1,500; 2,000; 2,500 parts per billion (ppb) or 1,000; 2,000; 3,000; 4,000; 5,000. After incubation the preparations were centrifuged at 10,000 rpm for 10 min. The supernatant was collected into amber and silanized HPLC vials, preventing any interaction of the mycotoxin or template with the vial, and calculated from HPLC (Alliance, Waters Corp., Milford, Mass., USA) coupled to photo diode-array detector signal (e.g., to detect amounts of mycotoxin and mycotoxin sequestered) according to standard methods. The HPLC analysis for gliotoxin was performed using a mixture of acetonitrile/acetic acid/trifluoroacetic acid (34.9:65:0.1, v/v) as mobile phase. The HPLC method for the detection of the 5-chloro-6,7-dimethoxy-1-methylisatine template was selected according to the standard elution parameters for sporidesmin analysis consisting of a mixture of acetonitrile/water/methanol (45:45:10, v/v). Detection was performed on the U.V. photodiode array with full wavelength scanning (268.1 nm gave the optimal signal for gliotoxin; 258.8 nm gave the optimal signal for the template).

Results showed that MIP #519-98 and #519-101 and NIP #519-99 and #519-10X were able to interact with more than 90.8% of the gliotoxin tested between 500 to 2,500 ppb for a 0.4% level of inclusion of the adsorbents at pH 4.0 (See Table 8). The adsorption of the 5-chloro-6,7-dimethoxy-1-methylisatine template was also investigated given an affinity of more than 94.9% for MIP #519-98 and #519-101 and NIP #519-99 and #519-10X for template concentrations between 1,000 to 5,000 ppb of the template molecule present in the medium at pH 4.0 for a 0.4% level of inclusion of the adsorbents (Table 8). Thus, in some embodiments, the present invention provides that the synthesized MIPs in toluene were both favorable to the adsorption of sporidesmin analogs (e.g., gliotoxin and 5-chloro-6,7-dimethoxy-1-methylisatine template) with a slight advantage for the MIP #519-101 synthesized using monomers of 2-vynilpyridine when added at an inclusion rate of 4 g/L under pH 4.0 with affinities for sequestration up to 97.82±4.25% of affinity rate and 95.85±1.25% respectively for gliotoxin and 5-chloro-6,7-dimethoxy-1-methylisatine template. Difference between the MIP and the NIP was minimal for any of the formulation prepared.

TABLE 8

Mean adsorption affinity expressed in percent for 2 MIPs and 2NIPs toward 5-chloro-6,7-dimethoxy-1-methylisatine template and gliotoxin evaluated at pH 4.0 and 0.4% level of inclusion of the adsorbent.

| Sample I.D. | Mean adsorption | |
| --- | --- | --- |
| | Gliotoxin (%) | Template (%) |
| MIP 519-98 | 90.84 ± 1.47 | 94.94 ± 2.21 |
| NIP 555-99 | 91.04 ± 1.51 | 95.35 ± 0.72 |

TABLE 8-continued

Mean adsorption affinity expressed in percent for 2 MIPs and 2NIPs toward 5-chloro-6,7-dimethoxy-1-methylisatine template and gliotoxin evaluated at pH 4.0 and 0.4% level of inclusion of the adsorbent.

| Sample I.D. | Mean adsorption | |
|---|---|---|
| | Gliotoxin (%) | Template (%) |
| MIP 519-101 | 97.82 ± 4.25 | 95.85 ± 1.25 |
| NIP 519-10X | 97.14 ± 4.02 | 95.86 ± 1.02 |

Example 18

Titration of the Amount of MIP for the Sequestration of Analogs of Sporidesmin

A titration experiment was conducted to investigate inclusion rates of MIP, from 0.1 g/L to 1.00 g/L (or 0.01 to 0.1% of inclusion rate). The preparation was made together with a blank sample containing no MIP material and a positive control containing only the 5-chloro-6,7-dimethoxy-1-methylisatine template or gliotoxin to be tested. The sequestration test was performed in citrate buffer 50 mM adjusted to pH 4.0. All samples were incubated during 90 min on an orbital rotary shaker (Brunswick, Champaign, Ill., USA) at 150 rpm maintained at a temperature of 37° C. Five final concentrations of 5-chloro-6,7-dimethoxy-1-methylisatine template or gliotoxin were tested with the system, 1,000; 2,000; 3,000; 4,000; 5,000 ppb in a final volume of 100 mL. After incubation the microcentrifuge tubes were centrifuged at 10,000 rpm for 10 min. The supernatant was collected into amber and silanized HPLC vials, preventing any interaction of the analyte with the vial, and calculated from HPLC (Alliance, Waters Corp., Milford, Mass., USA) coupled to diode-array detectors signal according to standard methods (See e.g., Example 17).

TABLE 9

Mean adsorption affinity expressed in percent for 2 MIPs and 3NIPs toward 5-chloro-6,7-dimethoxy-1-methylisatine template evaluated at pH 4.0 and 4 levels of inclusion of the adsorbent.

| | | Adsorption (%) | | | | | |
|---|---|---|---|---|---|---|---|
| | | Template concentration (ppb) | | | | | |
| Sample I.D. | % inclusion | 1,000 | 2,000 | 3,000 | 4,000 | 5,000 | Mean |
| MIP 519-98 | 0.010 | 48.90 | 57.93 | 48.17 | 37.86 | 38.63 | 46.30 |
| | 0.025 | 61.50 | 69.25 | 61.98 | 65.94 | 50.74 | 61.88 |
| | 0.050 | 80.37 | 87.95 | 73.97 | 76.41 | 69.28 | 77.59 |
| | 0.100 | 94.10 | 91.35 | 89.72 | 86.74 | 84.73 | 89.33 |
| NIP 519-99 | 0.010 | 59.83 | 53.83 | 41.80 | 42.17 | 38.40 | 47.21 |
| | 0.025 | 76.70 | 67.50 | 61.71 | 58.60 | 57.51 | 64.40 |
| | 0.050 | 89.63 | 83.18 | 73.08 | 75.46 | 77.25 | 79.72 |
| | 0.100 | 91.50 | 90.97 | 87.99 | 88.86 | 87.23 | 89.31 |
| MIP 519-101 | 0.010 | 48.60 | 37.95 | 39.12 | 38.29 | 34.72 | 39.74 |
| | 0.025 | 72.73 | 62.12 | 60.53 | 51.69 | 54.58 | 60.33 |
| | 0.050 | 76.93 | 73.40 | 73.94 | 70.98 | 70.17 | 73.09 |
| | 0.100 | 90.83 | 87.50 | 87.66 | 89.16 | 84.41 | 87.91 |
| NIP 519-10X | 0.010 | 41.33 | 42.88 | 36.18 | 25.54 | 26.58 | 34.70 |
| | 0.025 | 58.67 | 57.45 | 53.56 | 47.35 | 46.85 | 52.77 |
| | 0.050 | 75.20 | 68.38 | 68.26 | 65.43 | 63.66 | 68.19 |
| | 0.100 | 83.57 | 84.02 | 82.04 | 78.64 | 75.09 | 80.67 |
| NIP 519-47X | 0.010 | 16.57 | 7.48 | 10.59 | 17.05 | 10.39 | 12.42 |
| | 0.025 | 13.20 | 10.25 | 7.61 | 13.26 | 18.61 | 12.59 |
| | 0.050 | 4.17 | 12.40 | 11.92 | 12.12 | 13.76 | 10.87 |
| | 0.100 | 10.13 | 10.52 | 11.59 | 17.88 | 24.72 | 14.97 |

Figure 14:
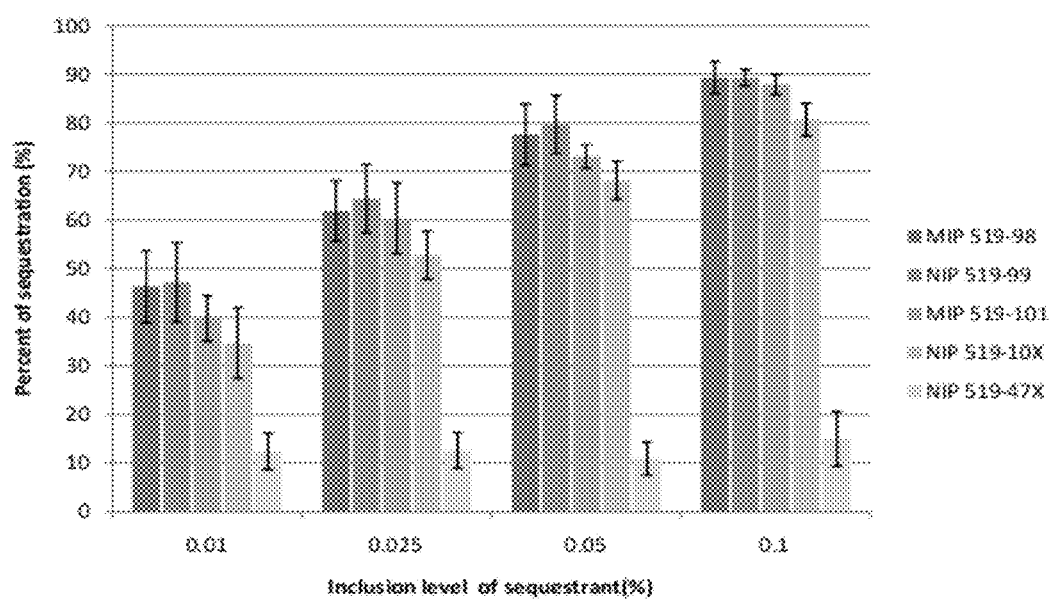
FIG. 14 shows the sequestration efficacy for the 5-chloro-6,7-dimethoxy-1-methylisatine template by the MIP-sporidesmin and NIP at several rates of inclusion.

As shown in FIG. 14, Table 9 and Table 10, in some embodiments, e.g., at 0.05 g/L of inclusion level of the adsorbent, the present invention showed an optimum efficacy above 70% of sequestration value and reached almost 90% of sequestration at 0.10 g/L. Thus, in some embodiments, the present invention provides that MIPs/NIP synthesized with methacrylic acid are more favorable over the MIP/NIP synthesized using 2-vinylpyridine for the adsorption of a sporidesmin analog (e.g., gliotoxin and 5-chloro-6,7-dimethoxy-1-methylisatine template (e.g., when added at an inclusion rate between 0.01 and 0.1 g/L under pH 4.0)). Differences between the MIP and the NIP were however minimal for any of the formulation prepared except for the NIP synthesized at low temperature and UV initiated polymerization with adsorption values increasing with the inclusion level of the adsorbent from 10 to 15%.

TABLE 10

In vitro isothermal adsorption characteristics of NIP and MIP at four different inclusion rates to Sporidesmin template in citrate buffer media of pH4.

| Inclusion (%) | NIP #519-99 | MIP #519-98 | NIP #519-10X | MIP #519-101 | NIP #519-47X |
|---|---|---|---|---|---|
| 0.010 | 47.207 ± 9.159 | 46.302 ± 8.297 | 34.703 ± 7.837 | 39.737 ± 5.229 | 12.416 ± 4.197 |
| 0.025 | 64.404 ± 7.894 | 61.882 ± 6.983 | 52.774 ± 5.517 | 60.331 ± 8.136 | 12.585 ± 4.101 |
| 0.050 | 79.720 ± 6.683 | 77.594 ± 7.047 | 68.186 ± 4.396 | 73.087 ± 2.671 | 10.873 ± 3.817 |
| 0.100 | 89.309 ± 1.858 | 89.329 ± 3.702 | 80.671 ± 3.767 | 87.912 ± 2.375 | 14.967 ± 6.288 |

Example 19

Affinity of Different MIP and NIP and Specificity Characterization Toward Sporidesmin Analogs Experiments were performed during development of embodiments of the invention in order to evaluate the affinity of different NIPs/MIPs synthesized in toluene as solvent used for heat initiated precipitation polymerization. The MIP produced were used herein to depict the differences in affinity of sequestration of the sporidesmin analogs (e.g., gliotoxin and 5-chloro-6,7-dimethoxy-1-methylisatine template) and to evaluate the specificity of the material. An amount of 30 mg of MIP was placed into a SEP-PAK column fitted with silanized polyethylene solid phase extraction frits. Silanized glass vials were utilized to ensure the stability of the analyte in aqueous solvents and to prevent any aspecific interaction between the analyte and the glass vials. The method of silanization was applied to nylon and PTFE/PE filters and tubes based on methods generally used in the art. The preparation was made together with a blank sample containing no MIP material and a positive control containing either the 5-chloro-6,7-dimethoxy-1-methylisatine template or gliotoxin. Solid Phase Extraction-like (SPE-like) filtering devices were generated for an equivalent of 0.1 g/L of inclusion of the MIP by filtering through 30 mg of material 1 mL of a solution of 5-chloro-6,7-dimethoxy-1-methylisatine template or gliotoxin. The vials and filters were prepared by filling them or immersing them with silanizing reagent (SURFASIL, See e.g., Example 9). The SPE-like filtering devices were loaded with a 1 mL solution of either 5-chloro-6,7-dimethoxy-1-methylisatine template or gliotoxin used at a single concentration of 2,000 ppb. Along with the samples, a control working solution was maintained. Samples and controls were both incubated at 37° C. for 2 min with intermittent shaking. After the incubation period, the samples were pushed through the syringe and were collected in 15 mL centrifuged tubes and centrifugation at 10,0000 g during 10 min. The supernatant were collected into amber and silanized HPLC vials and analyzed. To evaluate the specificity of the desorption for the targeted molecule, six washing steps were performed on the material containing the MIP polymers. Each of the washes were collected in 15 mL centrifuge tubes and centrifugation at 10,0000 g during 10 min before analysis via HPLC. Six washes were performed with increasing concentration of organic solvent, which included a first wash with 50 mM citrate buffer wash and five consecutive washes with 20, 40, 60, 80, 100% methanol in water (v/v), respectively. The experiment used the previously heat initiated precipitated polymerized MIP #519-98 and #519-101 and NIP #519-99 and #519-10X (powder forms) together with crystalline forms of MIP and NIP identified as #519-47 and #519-47X that were generated under low temperature and UV polymerization (See e.g., Example 5). The supernatant was collected into amber and silanized HPLC vials, preventing any interaction of the mycotoxin or template with the vial, and calculated from HPLC (Alliance, Waters Corp., Milford, Mass., USA) coupled to photo diode-array detector signal (e.g., to detect amounts of mycotoxin and mycotoxin sequestered) according to standard methods. The HPLC analysis for gliotoxin was performed using a mixture of acetonitrile/acetic acid/trifluoroacetic acid (34.9:65:0.1, v/v) as mobile phase. The HPLC method for the detection of the 5-chloro-6,7-dimethoxy-1-methylisatine template was selected according to the standard elution parameters for sporidesmin analysis consisting of a mixture of acetonitrile/water/methanol (45:45:10, v/v). Detection was performed on the U.V. photodiode array with full wavelength scanning (268.1 nm gave the optimal signal for gliotoxin; 258.8 nm gave the optimal signal for the template).

Figure 15:
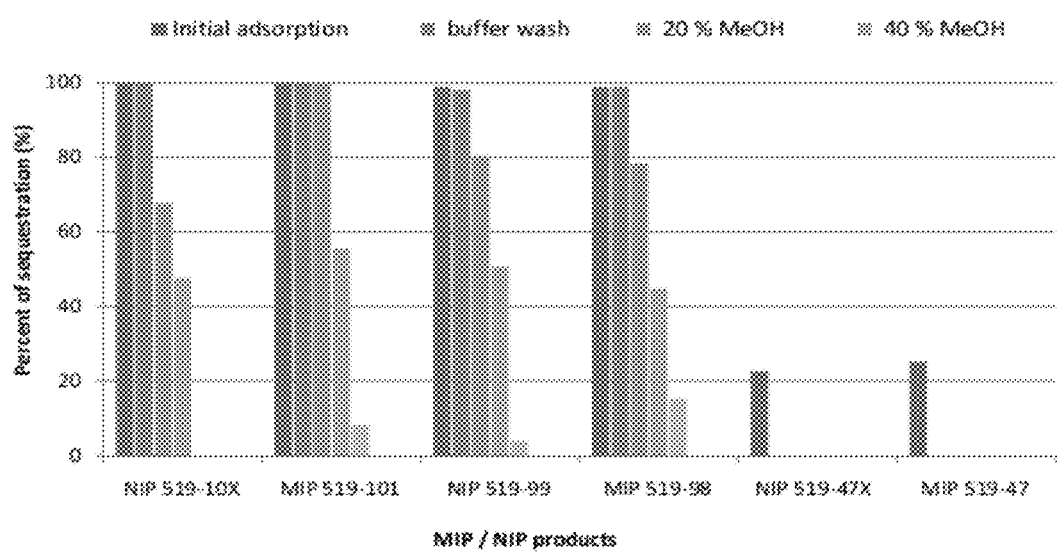
FIG. 15 shows the sequestration activity for gliotoxin of the MIPs and NIPs synthesized with heat initiated or low temperature/UV initiated polymerization and stability/specificity of the interaction after six successive washes performed with increasing level of methanol.

Results indicated (See FIG. 15 and Table 11) that MIPs #519-101 and #519-98 had lower desorption values when washed with 40% of methanol compared to their respective NIP #519-10X and #519-99 for the adsorption of gliotoxin. Washes containing more than 60% of methanol were however able to remove almost the entire amount of gliotoxin sequestered. In some embodiment, the MIP #519-101 synthesized using monomers of 2-vynilpyridine had higher specificity than the corresponding NIP #519-10X and the NIP #519-99, MIP #519-98, NIP #519-47X and MIP 519-47 when a wash using 20% of methanol was applied to the system. The polymers 519-47X and 519-47 were not able to adsorb more than 25% of the gliotoxin. The application of a buffer wash was able to remove any adsorbed gliotoxin.

Figure 16:
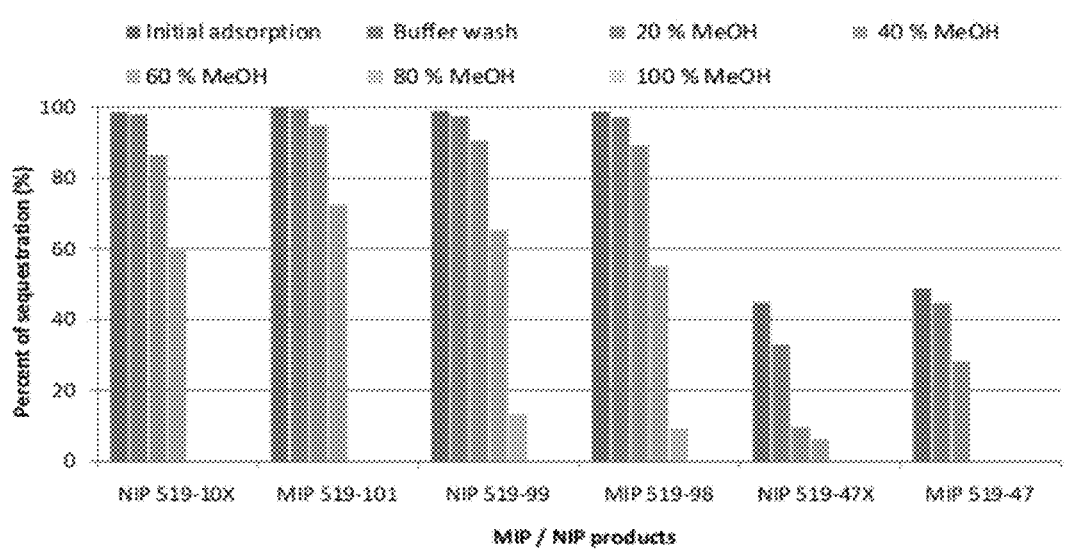
FIG. 16 shows the sequestration activity for 5-chloro-6,7-dimethoxy-1-methylisatine template of the MIPs and NIPs synthesized with heat initiated or low temperature/UV initiated polymerization and stability/specificity of the interaction after six successive washes performed with increasing level of methanol.

Results indicated (See FIG. 16 and Table 11) that MIPs #519-101 had lower desorption values when washed with 20 and 40% of methanol compared to its respective NIP #519-10X. The specificity of MIP #519-98 and NIP #519-99 were however comparable with no difference in specificity for the adsorption of 5-chloro-6,7-dimethoxy-1-methylisatine template. Washes containing more than 60% of methanol were however able to remove almost the entire amount of 5-chloro-6,7-dimethoxy-1-methylisatine template sequestered. In some embodiment and as found with gliotoxin, the MIP #519-101 synthesized using monomers of 2-vynilpyridine had higher specificity than the corresponding NIP #519-10X and the NIP #519-99, MIP #519-98, NIP #519-47X and MIP 519-47 when a wash using 20 and 40% of methanol was applied to the system. The polymers 519-47X and 519-47 exhibited difference in the specificity of sequestration in favor of the MIP compound. However, despite the adsorption of the 5-chloro-6,7-dimethoxy-1-methylisatine template being inferior to 50%, it presented a better affinity than that found with gliotoxin showing a better specificity of the MIP for the 5-chloro-6,7-dimethoxy-1-methylisatine template.

TABLE 11

Adsorption properties of 3 MIPs, 3NIPs, toward the 5-chloro-6,7-dimethoxy-1-methylisatine template and gliotoxin at pH 4.0 in a SPE configuration at 0.1% level of inclusion of the adsorbent and survival to titrated methanol washes with a mixture of citrate buffer (solution A) and methanol (solution B).

| Adsorbent | Mean percent adsorption | | | | | | |
|---|---|---|---|---|---|---|---|
| Conditions | Initial | A: 100% B: 0% | A: 80% B: 20% | A: 60% B: 40% | A: 40% B: 60% | A: 20% B: 80% | A: 0% B: 100% |
| Gliotoxin (% adsorption) | | | | | | | |
| NIP 519-10X | 99.3 ± 0.6 | 99.3 ± 0.0 | 67.7 ± 1.9 | 47.7 ± 1.4 | −0.3 ± 2.0 | 0.8 ± 1.6 | −0.8 ± 1.2 |
| MIP 519-101 | 99.9 ± 0.3 | 99.9 ± 0.0 | 99.9 ± 0.0 | 55.5 ± 0.1 | 8.3 ± 2.0 | −4.6 ± 3.1 | −5.1 ± 8.7 |
| NIP 519-99 | 99.0 ± 0.4 | 98.2 ± 0.4 | 80.5 ± 1.0 | 50.7 ± 2.8 | 4.0 ± 2.5 | −8.4 ± 6.1 | −7.6 ± 9.6 |
| MIP 519-98 | 99.1 ± 0.4 | 99.0 ± 0.3 | 78.5 ± 0.4 | 44.9 ± 2.2 | 15.4 ± 1.2 | −9.6 ± 14.8 | −6.1 ± 7.7 |
| NIP 555-47X | 22.7 ± 1.2 | −1.7 ± 1.5 | −10.6 ± 0.4 | −13.6 ± 6.5 | −28.4 ± 2.7 | −24.1 ± 11.4 | −33.4 ± 5.7 |
| MIP 519-47 | 25.1 ± 2.6 | −2.4 ± 10.5 | −18.5 ± 13.2 | −20.7 ± 3.05 | −28.2 ± 2.4 | −28.2 ± 11.1 | −36.5 ± 8.2 |
| 5-chloro-6,7-dimethoxy-1-methylisatine template (% adsorption) | | | | | | | |
| NIP 519-10X | 98.5 ± 0.8 | 98.0 ± 1.0 | 86.5 ± 0.2 | 59.5 ± 1.1 | −1.8 ± 1.0 | −39.4 ± 0.7 | −19.5 ± 1.8 |
| MIP 519-101 | 99.9 ± 0.1 | 99.4 ± 0.6 | 94.8 ± 0.1 | 72.4 ± 0.1 | −0.2 ± 1.3 | −2.2 ± 1.5 | −15.3 ± 1.5 |
| NIP 555-99 | 99.0 ± 0.6 | 97.5 ± 0.1 | 90.5 ± 0.2 | 65.2 ± 0.8 | 13.1 ± 1.4 | −1.85 ± 1.0 | −9.8 ± 1.4 |
| MIP 519-98 | 98.8 ± 0.2 | 97.2 ± 0.3 | 89.2 ± 0.7 | 55.1 ± 0.6 | 9.35 ± 1.3 | −7.9 ± 0.4 | −8.0 ± 3.3 |
| NIP 555-47X | 44.8 ± 5.6 | 33.0 ± 0.8 | 9.7 ± 3.9 | 6.2 ± 0.9 | −29.7 ± 0.1 | −17.5 ± 1.4 | −19.3 ± 3.2 |
| MIP 519-47 | 48.7 ± 7.0 | 44.7 ± 0.6 | 28.2 ± 0.6 | −17.1 ± 0.8 | −20.1 ± 2.1 | −21.3 ± 13.6 | −24.1 ± 3.4 |

Example 20

MIPs' Sequestration Capabilities Toward Mycotoxins—Applied to Sporidesmin

MIP polymer produced using 2-vynilpyridine monomers in toluene (See e.g., Example 15) was tested toward sporidesmin (AgResearch Limited, Ruakura Research Centre, Hamilton, New Zealand) for the removal of the sporidesmin (A 93%; B, D, E 2 to 17%) mycotoxins from liquid or semi-liquid media via chemical interactions. The MIP produced was used to characterize the affinity of sequestration and to evaluate the specificity of the material. A sequestration experiment was conducted by weighing 50 and 400 mg of MIP material into Schott bottles and addition of 100 mL of a working solution of sporidesmin mixture given 0.5 and 4.0 g/L of inclusion rate of the adsorbent in the medium. The preparation was made together with a blank sample containing no MIP material and a positive control containing the sporidesmins only. The sequestration test was performed in succinate buffer 50 mM adjusted to pH 6.0 to meet the physiological conditions of the rumen gastric compartment. All samples were incubated during 90 min on an orbital rotary shaker at 150 rpm maintained at a temperature of 37° C. Three final concentrations of sporidesmins were tested with the system, 500; 1,000; 2,000 ppb. After incubation the preparations were centrifuged at 10,000 rpm for 10 min. The supernatant was collected into HPLC vials, and calculated from HPLC coupled to UV detector signal (e.g., to detect amounts of mycotoxin and mycotoxin sequestered) according to standard methods. The HPLC method for the detection of sporidesmins used a mixture of acetonitrile/water/methanol (45:45:10, v/v) to perform the elution of the analytes and a C18 column (4.6 mm×25 cm). Detection was performed on the U.V. detector (280 nm gave the optimal signal for sporidesmins).

The MIP #519-98 product adsorbed 80.5 to 85.7% for an inclusion rate of 0.5 g/L and more than 98.5% when used at an inclusion rate of 4 g/L of sporidesmin present at 500; 1,000 and 2,000 ppb (See e.g., Table 12). Variation between repetitions accounted for less than 1% of the adsorption. A slight saturation effect could be observed at 0.5 g/L of inclusion rate with a decrease of the adsorption value obtained throughout the sporidesmin range investigated.

TABLE 12

MIP #519-98 adsorption efficacy at 0.5 and 4.0 g/L of inclusion rate toward 3 concentrations of sporidesmin.

| Inclusion | Mean Percent of Adsorption (%) for sporidesmin concentrations of: | | |
|---|---|---|---|
| rate (%) | 500 ppb | 1,000 ppb | 2,000 ppb |
| 0.05 | 85.65 ± 0.87 | 84.03 ± 0.70 | 80.51 ± 1.37 |
| 0.40 | 99.13 ± 0.00 | 98.85 ± 0.00 | 98.54 ± 0.09 |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A composition comprising a molecularly imprinted polymer synthesized using a mycotoxin template selected from the group consisting of N-(2-hydroxy-3,5-dichlorobenzoyl)-L-phenylalanine, 5-chloro-6,7-dimethoxy-1-methylisatine, ethyl 3-hydroxy-6,7-dimethoxy-2-indolone-3-carboxylate, 6,7-dimethoxyisatine, and 6,7-dimethoxy-1-methylisatine.

2. The composition of claim 1, wherein the mycotoxin template is N-(2-hydroxy-3,5-dichlorobenzoyl)-L-phenylalanine.

3. The composition of claim 1, wherein the mycotoxin template is 5-chloro-6,7-dimethoxy-1-methylisatine.

4. The composition of claim 1, wherein the molecularly imprinted polymer is made by providing N-(2-hydroxy-3,5- dichlorobenzoyl)-L-phenylalanine template and one or more monomers and one or more crosslinkers; and contacting the mycotoxin template with the one or more monomers and the one or more crosslinkers under conditions that permit polymerization of the one or more monomers and the one or more crosslinkers in the presence of the template.

5. The composition of claim 4, wherein the one or more monomers are selected from the group consisting of 2-vinylpyridine, 2-hydroxyethylmethacrylate and methacrylic acid.

6. The composition of claim 4, wherein the one or more crosslinkers comprise ethylene glycol dimethacrylate.

7. The composition of claim 1, wherein the molecularly imprinted polymer is made by providing N-(2-hydroxy-3,5-dichlorobenzoyl)-L-phenylalanine template and one or more monomers and one or more crosslinkers; and contacting the mycotoxin template with the one or more monomers and the one or more crosslinkers under conditions that permit polymerization of the one or more monomers and the one or more crosslinkers in the presence of the template.

8. The composition of claim 7, wherein the one or more monomers are selected from the group consisting of 2-vinylpyridine, 2-hydroxyethylmethacrylate and methacrylic acid.

9. The composition of claim 7, wherein the one or more crosslinkers comprise ethylene glycol dimethacrylate.

\* \* \* \* \*